United States Patent
Zinselmeier et al.

(10) Patent No.: US 8,017,834 B2
(45) Date of Patent: Sep. 13, 2011

(54) ENHANCED SILK EXSERTION UNDER STRESS

(75) Inventors: Christopher Zinselmeier, Grimes, IA (US); Timothy G Helentjaris, Tucson, AZ (US)

(73) Assignee: Pioneer Hi-Bred International, Inc., Johnson, IA (US)

( * ) Notice: Subject to any disclaimer, the term of this patent is extended or adjusted under 35 U.S.C. 154(b) by 535 days.

(21) Appl. No.: 12/101,378

(22) Filed: Apr. 11, 2008

(65) Prior Publication Data

US 2008/0307545 A1  Dec. 11, 2008

Related U.S. Application Data

(62) Division of application No. 10/409,701, filed on Apr. 8, 2003, now Pat. No. 7,358,419.

(60) Provisional application No. 60/370,796, filed on Apr. 8, 2002.

(51) Int. Cl.
*C12N 15/82* (2006.01)

(52) U.S. Cl. ..................................... 800/287; 800/290

(58) Field of Classification Search ..................... None
See application file for complete search history.

(56) References Cited

U.S. PATENT DOCUMENTS 6,060,644 A   5/2000  Schnable et al.
6,515,204 B1 *  2/2003  Ouellet et al. ................ 800/287

FOREIGN PATENT DOCUMENTS

WO   WO 00/63401   * 10/2000

OTHER PUBLICATIONS

Cazetta, Jairo O., et al.; "Sucrose and Nitrogen Supplies Regulate Growth of Maize Kernels": Annals of Botany (1999) 84:747-754.
Estruch, J.J., et al.; "Floral Development and Expression of Floral Homeotic Genes Are Influenced by Cytokinins"; The Plant Journal (1993) 4(2):379-384.

* cited by examiner

*Primary Examiner* — Cynthia Collins

(57) ABSTRACT

The invention provides methods for enhancing maize silk exsertion under stress conditions and compositions relating to such methods, including nucleic acids and proteins. The invention further provides recombinant expression cassettes, host cells, and transgenic plants.

5 Claims, No Drawings

ENHANCED SILK EXSERTION UNDER STRESS

REFERENCE TO RELATED APPLICATIONS

This application is a divisional of co-pending U.S. patent application Ser. No. 10/409,701 filed Apr. 8, 2003 which claims the benefit of, and incorporates by reference, Provisional Patent Application 60/370,796, filed Apr. 8, 2002.

TECHNICAL FIELD

The present invention relates generally to plant molecular biology. More specifically, it relates to nucleic acids and methods for modulating their expression in plants.

BACKGROUND OF THE INVENTION

Throughout their lives, plants are routinely subjected to a variety of stresses which act to impede or alter growth and development processes. Stress to the growth and development of agricultural plants has a negative economic impact in the form of reduced yields, increased expenditures to ameliorate the effects of stress, or both. Given the world's increasing human population and the diminishing land area available for agriculture, improving agricultural productivity is of paramount importance. Thus, there is a need for crop plants that are better able to tolerate stresses and maintain productivity under unfavorable conditions.

While traditional plant breeding approaches will continue to be important for improving agricultural plants, the new strategies that are likely to have the most significant impact on crop improvement will involve genetic engineering. A thorough understanding of the molecular and cellular mechanisms used by plants to avoid or tolerate stresses will aid in the development of new strategies to improve the stress tolerance of agricultural plants.

Stresses to plants may be caused by both biotic and abiotic agents. For example, biotic causes of stress include infection with a pathogen, insect feeding, parasitism by another plant such as mistletoe, and grazing by animals. Abiotic stresses include, for example, excessive or insufficient available water, insufficient light intensity, temperature extremes, synthetic chemicals such as herbicides, and excessive wind. Yet plants survive and often flourish, even under unfavorable conditions, using a variety of internal and external mechanisms for avoiding or tolerating stress. Plants' physiological responses to stress reflect changes in gene expression.

Grain yield in *Zea mays* is dependent upon the number of ovaries which are initiated, are fertilized, and develop to maturity. Reduced grain production may result from, inter alia, a decrease in the number of kernel initials, restricted or untimely silk exsertion, and/or kernel abortion during grain development.

Maize silks comprise the stigmatic tissues of the flower, intercepting air-borne pollen and supporting pollen tube growth to result in fertilization. Silk receptivity to pollen is limited in duration and is affected by environmental factors. For example, under drought conditions, silk exsertion is delayed or restricted and thus may not occur at the proper time relative to pollen shed. (See, for example, Herrero and Johnson, (1981) *Crop Science* 21:105-110) Importantly, the process of fertilization determines kernel number and thus sets an irreversible upper limit on grain yield.

What is needed in the art is a means to stabilize yield of maize across environments by ensuring ample and timely silk exsertion. This can be accomplished through transgenic modifications to create a plant with constant or increased rates of silk exsertion, even under stress, relative to an unmodified plant.

Modification of gene expression affecting silk growth and development requires use of promoters expressed exclusively or preferentially in silk tissues; for example, see, U.S. Pat. No. 6,515,204. Also needed are coding regions capable of enhancing silk growth and development. The present invention meets these and other objectives.

SUMMARY OF THE INVENTION

Generally, it is an object of the present invention to provide methods of transforming plants with genetic constructs comprising novel combinations of appropriate promoter sequences and coding sequences to result in transformed plants with improved silk development under conditions of stress, relative to an untransformed plant under stress. Further objects of the present invention are to provide said transgenic plants exhibiting improved silk development under stress, and to provide said genetic constructs.

For example, cell division may be limiting to silk development under stress. Transformation with cytokinin biosynthetic genes would help to continue driving cell division in spite of stress to the plant. *Arabidopsis* plants transformed with ipt from *Agrobacterium tumefaciens* demonstrated increased flooding tolerance correlated with increased expression of ipt. (VanToai, et al., Abstract P518, Plant and Animal Genome VII Conference, San Diego, Calif., Jan. 17-21, 1999) Seed-specific expression of the *Agrobacterium tumefaciens* tzs gene in transgenic tobacco resulted in increased seed weight and number. (Roeckel, et al., (1998) *Physiologia Plantarum* 102:243-249) Dietrich, et al., (*Plant Physiol. Biochem.* 33(3):327-336, 1995) showed that maximum cell division activity within developing maize endosperm coincided with the peak in total kernel cytokinin concentration. Thus, increasing cytokinin levels in the developing silk could serve to increase or maintain cell division and silk exsertion under stress conditions.

Alternatively or additionally, cell cycle genes, such as cyclin D, would help to continue driving cell division and thus maintain silk development in spite of stress to the plant. Cockcroft, et al., (*Nature* 405:575-579, 2000) found that tobacco plants transformed with CycD2 under control of a constitutive promoter had elevated overall growth rates. Riou-Khamlichi, et al., (*Science* 283:1541-1544, 1999) reported that CycD3 could induce cell division when constitutively expressed in transgenic *Arabidopsis* callus. Thus, increased expression of cell cycle genes specifically in silk tissue could promote cell division and silk growth.

Alternatively or additionally, transformation resulting in increased, directed expression of sucrose symporters could increase the carbon supply to developing silks. Symporters act to accumulate sucrose from the apoplast and transport it across cell boundaries, such as into phloem sieve elements or companion cells. Symporters may also transport monosaccharides, and their activity could be important in silk development, providing hexoses to elongating cells to maintain osmotic pressure and provide precursors for macromolecular synthesis. For a review, see, Williams, et al., (2000) *Trends in Plant Science* 5(7):283-290. There is evidence for tissue specificity and for transcriptional regulation of expression of sucrose symporters (Williams, supra, at pp. 287 and 289). Further, biotic and abiotic stresses can affect the expression of sucrose symporters. See, for example, Noiraud, et al., (2000) *Plant Physiology* 122:1447-1455. Thus, constructs directing increased or sustained expression of sucrose symporters in female reproductive tissues at critical developmental stages could be useful in maintaining growth and function of the silks. Leggewie, et al., (U.S. Pat. No. 6,025,544) teach transformation with sucrose transporter sequences for earlier and/or more prolific flowering. The present invention, in contrast, provides transformation with sucrose transporter sequences to result in sustained or improved silk development under conditions of stress, especially drought, density and/or heat stress.

Alternatively or additionally, transformation resulting in targeted upregulation of invertases could increase the carbon supply to developing silks. Invertases convert sucrose into its component monosaccharides, glucose and fructose. Soluble invertase activity creating an increased solute concentration within a cell would serve to draw water into the cell and cause it to expand. In maize, a soluble invertase, Ivr2, has been shown to be specifically induced under water stress, and the resulting increase in hexose accumulation was speculated to increase osmotic pressure which could provide drought resistance. (Kim, et al., (2000) *Plant Physiology* 124:71-84). Overexpression of Ivr2 in silk tissues could therefore drive desirable cell expansion under conditions of water stress.

Alternatively or additionally, increased expression of a sodium antiporter within silk tissues could result in improved silk development under drought stress. Overexpression in *Brassica napus* of AtNHX1, encoding a vacuolar sodium antiporter from *Arabidopsis*, produces plants with reduced sensitivity to salt. Sodium ions are moved into the vacuole, increasing the solute concentration, which results in water being drawn into the cell. (Zhang, et al., (2001) *PNAS* 98(22): 12832-12836) Overexpression of AtNHX1 or a gene encoding a protein of similar function within maize silk tissues could therefore drive increased water rentention and desirable cell expansion under conditions of water stress. Such gene may be from maize.

Alternatively or additionally, adequate osmotic potential for cell expansion could result from directed overexpression of a vacuolar pyrophosphatase. Gaxiola, et al., have reported that overexpression of the *Arabidopsis* AVP1 gene, which encodes a vacuolar pyrophosphatase, resulted in marked drought tolerance, apparently through increased vacuolar accumulation of solute causing enhanced cellular water retention. (*PNAS* 98(20):11444-11449, 2001). Overexpression of AVP1 or a gene encoding a protein of similar function within maize silk tissues could therefore drive increased water retention and desirable cell expansion under conditions of water stress.

Alternatively or additionally, expansins could help to drive silk cell expansion. Expansins are extracellular proteins which catalyze cell-wall enlargement by breaking non-covalent bonds between cell-wall polysaccharides. Increased expression of expansin genes has been correlated with rapid stem growth in submerged rice (Cho and Kende, (1997) *Plant Cell* 9:1661-1671) and with root growth of maize seedlings under drought stress (Wu, et al., (1996) *Plant Physiol.* 111: 765-772). Directed expression of expansins could aid in cell enlargement, thus increasing silk length, particularly under stress conditions.

Alternatively or additionally, directed expression of aquaporins could aid in silk cell expansion. Aquaporins, designated TIPs (Tonoplast Intrinsic Proteins) or MIPs (plasma-Membrane Intrinsic Proteins), are channel proteins which facilitate water movement across vacuolar or plasma membranes. The maize aquaporin gene ZmTIP1 is expressed at high levels in expanding cells, consistent with the hypothesis that TIPs allow rapid uptake of water. (Chaumont, et al., (1998) *Plant Physiol.* 117:1143-1152) Upregulated and directed expression of aquaporins, including those endogenous to maize and particularly those expressed in maize silk tissue, could support rapid silk cell expansion and thus promote silk tissue growth. See, also, U.S. Pat. Nos. 6,313,375 and 6,313,376, hereby incorporated by reference.

Alternatively or additionally, targeted expression of genes encoding enzymes involved in raffinose synthase may provide tolerance of drought, salinity, and/or cold. Taji, et al., (*Plant Journal* 29(4):417-426, 2002) have reported that "stress-inducible galactinol synthase plays a key role in the accumulation of galactinol and raffinose under abiotic stress conditions" and that "galactinol and raffinose may function as osmoprotectants in drought-stress tolerance of plants." Therefore, constructs directing overexpression of galactinol synthase or raffinose synthase in silk tissue could lead to improved silk exsertion under abiotic stress.

It is a further object of the invention to provide promoter sequences active exclusively or preferentially in silks and methods of use of the promoter sequences. In other aspects the present invention relates to: 1) recombinant expression cassettes, comprising a nucleic acid of the present invention operably linked to a promoter, 2) a host cell into which has been introduced the recombinant expression cassette, and 3) a transgenic plant comprising the recombinant expression cassette. The host cell and plant are optionally from maize.

It is a further object of the present invention to provide a method of improved control of expression of an endogenous or exogenous product in a transformed plant or its progeny.

It is a further object of the present invention to provide a method for effecting useful changes in the phenotype of a transformed plant or its progeny.

It is a further object of the present invention to provide a method for modulating the development of a transformed plant or its progeny.

In a further aspect, the present invention relates to a method for modulating gene expression in a stably transformed plant comprising the steps of (a) transforming a plant cell with a recombinant expression cassette of the present invention; (b) growing the plant cell under appropriate growing conditions and (c) regenerating a stably transformed plant from the plant cell wherein said linked nucleotide sequence is expressed.

DETAILED DESCRIPTION OF THE INVENTION

Overview

A. Nucleic Acids and Proteins of the Present Invention

Unless otherwise stated, the polynucleotide and polypeptide sequences identified in SEQ ID NOS: 1-26 represent exemplary polynucleotides and polypeptides useful in the present invention. Table 1 provides identification of SEQ ID NOS: 1-26.

| Gene Name | Polynucleotide SEQ ID NO. | Polypeptide SEQ ID NO. |
| --- | --- | --- |
| Silk-preferred promoter ("gl2") | 1, 26 | — |
| Isopentenyl transferase | 2 | 3 |
| Cyclin D | 4 | 5 |
| Cyclin-dependent kinase | 6 | 7 |
| α-expansin | 8 | 9 |
| β-expansin | 10 | 11 |
| Aquaporin | 12 | 13 |
| Aquaporin | 14 | 15 |
| Aquaporin | 16 | 17 |
| Sucrose symporter | 18 | 19 |
| Soluble invertase | 20 | 21 |
| Sodium antiporter | 22 | 23 |
| Vacuolar pyrophosphatase | 24 | 25 |

B. Exemplary Utility of the Present Invention

The present invention provides utility in such exemplary applications as engineering *Zea mays* plants to exhibit improved silk exsertion, relative to a non-transformed plant, under conditions of environmental stress, such as drought, high plant density, or excessive heat.

Improved silk exsertion may comprise elements of timeliness and quality, for example, more rapid exsertion, greater silk length, and more complete and/or more uniform silk emergence from the ear shoot. Such improvements in silk exsertion may result from, for example, increased rates of cell division in silk tissue, increased expansion of cells composing silks, and altered rates of flow of water and solutes within or into silk tissue.

Definitions

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges recited within the specification are inclusive of the numbers defining the range and include each integer within the defined range. Amino acids may be referred to herein by either their commonly known three-letter symbols or by the one-letter symbols recommended by the IUPAC-IUBMB Nomenclature Commission. Nucleotides, likewise, may be referred to by their commonly accepted single-letter codes. Unless otherwise provided for, software, electrical, and electronics terms as used herein are as defined in The New IEEE Standard Dictionary of Electrical and Electronics Terms (5$^{th}$ edition, 1993). The terms defined below are more fully defined by reference to the specification as a whole. Section headings provided throughout the specification are not limitations to the various objects and embodiments of the present invention.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., *Diagnostic Molecular Microbiology: Principles and Applications*, Persing, et al., Ed., American Society for Microbiology, Washington, D.C. (1993). The product of amplification is termed an amplicon.

As used herein, "antisense orientation" includes reference to a duplex polynucleotide sequence that is operably linked to a promoter in an orientation where the antisense strand is transcribed. The antisense strand is sufficiently complementary to an endogenous transcription product such that translation of the endogenous transcription product is often inhibited.

By "encoding" or "encoded", with respect to a specified nucleic acid, is meant comprising the information for translation into the specified protein. A nucleic acid encoding a protein may comprise intervening sequences (e.g., introns) within translated regions of the nucleic acid, or may lack such intervening sequences (e.g., as in cDNA). The information by which a protein is encoded is specified by the use of codons. Typically, the amino acid sequence is encoded by the nucleic acid using the "universal" genetic code. However, variants of the universal code, such as are present in some plant, animal, and fungal mitochondria, the bacterium *Mycoplasma capricolum*, or the ciliate *Macronucleus*, may be used when the nucleic acid is expressed therein.

When the nucleic acid is prepared or altered synthetically, advantage can be taken of known codon preferences of the intended host organism. For example, although nucleic acid sequences of the present invention may be expressed in both monocotyledonous and dicotyledonous plant species, sequences can be modified to account for the specific codon preferences and GC content preferences of monocotyledons or dicotyledons as these preferences have been shown to differ (Murray, et al., (1989) *Nucl. Acids Res.* 17: 477-498). Thus, the maize-preferred codon for a particular amino acid may be derived from known gene sequences from maize. Maize codon usage for 28 genes from maize plants is listed in Table 4 of Murray, et al., supra.

As used herein "full-length sequence" in reference to a specified polynucleotide or its encoded protein means having the entire amino acid sequence of a native (non-synthetic), endogenous, biologically (e.g., structurally or catalytically) active form of the specified protein. Methods to determine whether a sequence is full-length are well known in the art, including such exemplary techniques as northern or western blots, primer extension, S1 protection, and ribonuclease protection. See, e.g., *Plant Molecular Biology: A Laboratory Manual*, Clark, Ed., Springer-Verlag, Berlin (1997). Comparison to known full-length homologous (orthologous and/or paralogous) sequences can also be used to identify full-length sequences of the present invention. Additionally, consensus sequences typically present at the 5' and 3' untranslated regions of mRNA aid in the identification of a polynucleotide as full-length. For example, the consensus sequence ANNNNAUGG, where the underlined codon represents the N-terminal methionine, aids in determining whether the polynucleotide has a complete 5' end. Consensus sequences at the 3' end, such as polyadenylation sequences, aid in determining whether the polynucleotide has a complete 3' end.

As used herein, "heterologous" in reference to a nucleic acid is a nucleic acid that originates from a foreign species, or, if from the same species, is substantially modified from its native form in composition and/or genomic locus by human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by human intervention.

By "host cell" is meant a cell which contains a vector and supports the replication and/or expression of the vector. Host cells may be prokaryotic cells such as *E. coli*, or eukaryotic cells such as yeast, insect, amphibian, or mammalian cells. Preferably, host cells are monocotyledonous or dicotyledonous plant cells. A particularly preferred monocotyledonous host cell is a maize host cell.

The term "introduced" includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA). The term includes such nucleic acid introduction means as "transfection", "transformation" and "transduction".

The term "isolated" refers to material, such as a nucleic acid or a protein, which is substantially free from components that normally accompany or interact with it in its naturally-occurring environment. The isolated material optionally comprises material not found with the material in its natural environment, or if the material is in its natural environment, the material has been synthetically (non-naturally) altered by human intervention to a composition and/or placed at a location in the cell (e.g., genome or subcellular organelle) not native to the isolated material. The alteration to yield the synthetic material can be performed on the material within or removed from its natural state. For example, a naturally-occurring nucleic acid becomes an isolated nucleic acid if it is altered, or if it is transcribed from DNA which has been altered, by means of human intervention performed within the cell from which it originates. See, e.g., Compounds and Methods for Site Directed Mutagenesis in Eukaryotic Cells, Kmiec, U.S. Pat. No. 5,565,350; In Vivo Homologous Sequence Targeting in Eukaryotic Cells; Zarling, et al., PCT/US93/03868. Likewise, a naturally-occurring nucleic acid (e.g., a promoter) becomes isolated if it is introduced by non-naturally-occurring means to a locus of the genome not native to that nucleic acid.

As used herein, "nucleic acid" includes reference to a deoxyribonucleotide or ribonucleotide polymer, or chimeras thereof, in either single- or double-stranded form, and unless otherwise limited, encompasses known analogues having the essential nature of natural nucleotides in that they hybridize to single-stranded nucleic acids in a manner similar to that of naturally-occurring nucleotides (e.g., peptide nucleic acids).

By "nucleic acid library" is meant a collection of isolated DNA or RNA molecules which comprise and substantially represent the entire transcribed fraction of a genome of a specified organism, or of a tissue or cell type from that organism. Construction of exemplary nucleic acid libraries, such as genomic and cDNA libraries, is taught in standard molecular biology references such as Berger and Kimmel, *Guide to Molecular Cloning Techniques, Methods in Enzymology*, Vol. 152, Academic Press, Inc., San Diego, Calif. (Berger); Sambrook, et al., *Molecular Cloning—A Laboratory Manual*, 2nd ed., Vol. 1-3 (1989); and *Current Protocols in Molecular Biology*, Ausubel, et al., Eds., Current Protocols, a joint venture between Greene Publishing Associates, Inc. and John Wiley & Sons, Inc. (1994).

As used herein "operably linked" includes reference to a functional linkage between a promoter and a second sequence, wherein the promoter sequence initiates and mediates transcription of the second sequence. Generally, operably linked means that the nucleic acid sequences being linked are contiguous and, where necessary to join two protein coding regions, contiguous and in the same reading frame.

As used herein, the term "plant" includes reference to whole plants, plant organs (e.g., leaves, stems, roots, etc.), seeds and plant cells and progeny of same. Plant cell, as used herein includes, without limitation, cells isolated from seeds, suspension cultures, embryos, meristematic regions, callus tissue, leaves, roots, shoots, gametophytes, sporophytes, pollen, and microspores. The class of plants which can be used in the methods of the invention include both monocotyledonous and dicotyledonous plants. A particularly preferred plant is *Zea mays*.

As used herein, "polynucleotide" includes reference to a deoxyribopolynucleotide, ribopolynucleotide, or chimeras or analogs thereof that have the essential nature of a natural deoxy- or ribo-nucleotide in that they hybridize, under stringent hybridization conditions, to substantially the same nucleotide sequence as do naturally-occurring nucleotides and/or allow translation into the same amino acid(s) as do the naturally-occurring nucleotide(s). A polynucleotide can be full-length or a subsequence of a native or heterologous structural or regulatory gene. Unless otherwise indicated, the term includes reference to the specified sequence as well as to the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms apply to naturally-occurring amino acid polymers, as well as to amino acid polymers in which one or more amino acid residue is an artificial chemical analogue of a corresponding naturally-occurring amino acid. The essential nature of such analogues of naturally-occurring amino acids is that, when incorporated into a protein, that protein is specifically reactive to antibodies elicited to the same protein but consisting entirely of naturally-occurring amino acids. The terms "polypeptide", "peptide" and "protein" are also inclusive of modifications including, but not limited to, glycosylation, lipid attachment, sulfation, gamma-carboxylation of glutamic acid residues, hydroxylation and ADP-ribosylation. Further, this invention contemplates the use of both the methionine-containing and the methionine-less amino terminal variants of proteins of the invention.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells whether or not its origin is a plant cell. Exemplary plant promoters include, but are not limited to, those that are obtained from plants, plant viruses, and bacteria which comprise genes expressed in plant cells such *Agrobacterium* or *Rhizobium*. Examples of promoters under developmental control include promoters that preferentially initiate transcription in certain tissues, such as leaves, roots, or seeds. Such promoters are referred to as "tissue preferred". Promoters which initiate transcription only in certain tissue are referred to as "tissue specific". A "cell type" specific promoter primarily drives expression in certain cell types in one or more organs, for example, vascular cells in roots or leaves. An "inducible" or "repressible" promoter is a promoter which is under environmental control. Examples of environmental conditions that may effect transcription by inducible promoters include anaerobic conditions or the presence of light. Tissue specific, tissue preferred, cell type specific, and inducible promoters constitute the class of "non-constitutive" promoters. A "constitutive" promoter is a promoter which is active under most conditions.

As used herein "recombinant" includes reference to a cell or vector that has been modified by the introduction of a heterologous nucleic acid or to a cell derived from a cell so modified. Thus, for example, recombinant cells express genes that are not found in identical form within the native (non-recombinant) form of the cell or express native genes that are otherwise abnormally expressed, under-expressed or not expressed at all, as a result of human intervention. The term "recombinant" as used herein does not encompass the alteration of the cell or vector by naturally-occurring events (e.g., spontaneous mutation, natural transformation/transduction/transposition) such as those occurring without human intervention.

As used herein, a "recombinant expression cassette" is a nucleic acid construct, generated recombinantly or synthetically, with a series of specified nucleic acid elements which permit transcription of a particular nucleic acid in a host cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a promoter and a nucleic acid to be transcribed.

The terms "residue" and "amino acid residue" and "amino acid" are used interchangeably herein to refer to an amino acid that is incorporated into a protein, polypeptide, or peptide (collectively "protein"). The amino acid may be a naturally-occurring amino acid and, unless otherwise limited, may encompass non-natural analogs of natural amino acids that can function in a similar manner as naturally-occurring amino acids.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, preferably 90% sequence identity, and most preferably 100% sequence identity (i.e., are complementary) with each other.

The term "stringent conditions" or "stringent hybridization conditions" includes reference to conditions under which a probe will selectively hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl, (1984) *Anal. Biochem.*, 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. Hybridization and/or wash conditions can be applied for at least 10, 30, 60, 90, 120 or 240 minutes. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York (1993); and *Current Protocols in Molecular Biology*, Chapter 2, Ausubel, et al., Eds., Greene Publishing and Wiley-Interscience, New York (1995).

As used herein, "transgenic plant" includes reference to a plant which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally-occurring events such as random cross-fertilization, non-recombinant viral infection, non-recombinant bacterial transformation, non-recombinant transposition, or spontaneous mutation.

As used herein, "vector" includes reference to a nucleic acid used in introduction of a polynucleotide of the present invention into a host cell. Vectors are often replicons. Expression vectors permit transcription of a nucleic acid inserted therein.

The following terms are used to describe the sequence relationships between a polynucleotide/polypeptide of the present invention with a reference polynucleotide/polypeptide: (a) "reference sequence", (b) "comparison window", (c) "sequence identity", and (d) "percentage of sequence identity".

(a) As used herein, "reference sequence" is a defined sequence used as a basis for sequence comparison with a polynucleotide/polypeptide of the present invention. A reference sequence may be a subset or the entirety of a specified sequence; for example, as a segment of a full-length cDNA or gene sequence, or the complete cDNA or gene sequence.

(b) As used herein, "comparison window" includes reference to a contiguous and specified segment of a polynucleotide/polypeptide sequence, wherein the polynucleotide/polypeptide sequence may be compared to a reference sequence and wherein the portion of the polynucleotide/polypeptide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides/amino acids residues in length, and optionally can be 30, 40, 50, 100, 200, 300, 400, 500, 600, 750, 1000, 1250, 1500 or longer. Those of skill in the art understand that to avoid a high similarity to a reference sequence due to inclusion of gaps in the polynucleotide/polypeptide sequence, a gap penalty is typically introduced and is subtracted from the number of matches.

Methods of alignment of sequences for comparison are well-known in the art. Optimal alignment of sequences for comparison may be conducted by the local homology algorithm of Smith and Waterman, (1981) *Adv. Appl. Math.* 2:482; by the homology alignment algorithm of Needleman and Wunsch, (1970) *J. Mol. Biol.* 48:443; by the search for similarity method of Pearson and Lipman, (1988) *Proc. Natl. Acad. Sci.* 85:2444; by computerized implementations of these programs, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA. The CLUSTAL program is well described by Higgins and Sharp, (1988) *Gene* 73:237-244; Higgins and Sharp, (1989) *CABIOS* 5:151-153; Corpet, et al., (1988) *Nucleic Acids Research* 16:10881-90; Huang, et al., (1992) *Computer Applications in the Biosciences* 8:155-65, and Pearson, (1994) et al., *Methods in Molecular Biology* 24:307-331.

The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel, et al., Eds., Greene Publishing and Wiley-Interscience, New York (1995); Altschul, et al., (1990) *J. Mol. Biol.* 215:403-410; and Altschul, et al., (1997) *Nucleic Acids Res.* 25:3389-3402.

Software for performing BLAST analyses is publicly available, e.g., through the National Center for Biotechnology Information. This program involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST program parameters W, T, and X determine the sensitivity and speed of the alignment. The BLASTN program (for nucleotide sequences) uses as defaults a wordlength (W) of 11, an expectation (E) of 10, a cutoff of 100, M=5, N=-4, and a comparison of both strands. For amino acid sequences, the BLASTP program uses as defaults a wordlength (W) of 3, an expectation (E) of 10, and the BLOSUM62 scoring matrix (see, Henikoff and Henikoff, (1989) *Proc. Natl. Acad. Sci. USA* 89:10915).

In addition to calculating percent sequence identity, the BLAST program also performs a statistical analysis of the similarity between two sequences (see, e.g., Karlin and Altschul, (1993) *Proc. Natl. Acad. Sci. USA* 90:5873-5877). One measure of similarity provided by the BLAST program is the smallest sum probability (P(N)), which provides an indication of the probability by which a match between two nucleotide or amino acid sequences would occur by chance.

BLAST searches assume that proteins can be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, (1993) *Comput. Chem.* 17:149-163) and XNU (Clayerie and States, (1993) *Comput. Chem.* 17:191-201) low-complexity filters can be employed alone or in combination.

Unless otherwise stated, nucleotide and protein identity/similarity values provided herein are calculated using GAP (GCG Version 10) under default values.

GAP (Global Alignment Program) can also be used to compare a polynucleotide or polypeptide of the present invention with a reference sequence. GAP uses the algorithm of Needleman and Wunsch (*J. Mol. Biol.* 48:443-453, 1970) to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. For polypeptide sequences the default gap creation penalty is 8 while the default gap extension penalty is 2. The gap creation and gap extension penalties can be expressed as an integer selected from the group of integers consisting of from 0 to 100. Thus, for example, the gap creation and gap extension penalties can each independently be: 0, 1, 2, 3, 4, 5, 6, 7, 8, 9, 10, 15, 20, 30, 40, 50, 60 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see, Henikoff and Henikoff, (1989) *Proc. Natl. Acad. Sci. USA* 89:10915).

Multiple alignment of the sequences can be performed using the CLUSTAL method of alignment (Higgins and Sharp, (1989) *CABIOS.* 5:151-153) with the default parameters (GAP PENALTY=10, GAP LENGTH PENALTY=10). Default parameters for pairwise alignments using the CLUSTAL method are KTUPLE 1, GAP PENALTY=3, WINDOW=5 and DIAGONALS SAVED=5.

(c) As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, (1988) *Computer Applic. Biol. Sci.,* 4:11-17, e.g., as implemented in the program PC/GENE (Intelligenetics, Mountain View, Calif., USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

Utilities

The present invention provides, among other things, compositions and methods for modulating (i.e., increasing or decreasing) the level of polynucleotides and polypeptides of the present invention in plants. In particular, the polynucleotides and polypeptides of the present invention can be expressed temporally or spatially, e.g., at developmental stages, in tissues, and/or in quantities, which are uncharacteristic of non-recombinantly engineered plants.

The present invention also provides isolated nucleic acids comprising polynucleotides of sufficient length and complementarity to a polynucleotide of the present invention to use as probes or amplification primers in the detection, quantitation, or isolation of gene transcripts. For example, isolated nucleic acids of the present invention can be used as probes in detecting deficiencies in the level of mRNA in screenings for desired transgenic plants, for detecting mutations in the gene (e.g., substitutions, deletions, or additions), for monitoring upregulation of expression or changes in enzyme activity in screening assays of compounds, for detection of any number of allelic variants (polymorphisms), orthologs, or paralogs of the gene, or for site directed mutagenesis in eukaryotic cells (see, e.g., U.S. Pat. No. 5,565,350). The isolated nucleic acids of the present invention can also be used for recombinant expression of their encoded polypeptides, or for use as immunogens in the preparation and/or screening of antibodies. The isolated nucleic acids of the present invention can also be employed for use in sense or antisense suppression of one or more genes of the present invention in a host cell, tissue, or plant. Attachment of chemical agents which bind, intercalate, cleave and/or crosslink to the isolated nucleic acids of the present invention can also be used to modulate transcription or translation.

The present invention also provides isolated proteins comprising a polypeptide of the present invention (e.g., preproenzyme, proenzyme, or enzymes). The present invention also provides proteins comprising at least one epitope from a polypeptide of the present invention. The proteins of the present invention can be employed in assays for enzyme agonists or antagonists of enzyme function, or for use as immunogens or antigens to obtain antibodies specifically immunoreactive with a protein of the present invention. Such antibodies can be used in assays for expression levels, for identifying and/or isolating nucleic acids of the present invention from expression libraries, for identification of homologous polypeptides from other species, or for purification of polypeptides of the present invention.

The isolated nucleic acids and polypeptides of the present invention can be used over a broad range of plant types, particularly monocots such as the species of the family Gramineae including *Hordeum, Secale, Oryza, Triticum, Sorghum* (e.g., *S. bicolor*) and *Zea* (e.g., *Z. mays*), and dicots such as *Glycine*.

The isolated nucleic acid and proteins of the present invention can also be used in species from the genera: *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browallia, Pisum, Phaseolus, Lolium,* and *Avena.*

Nucleic Acids

The present invention provides, among other things, isolated nucleic acids of RNA, DNA, and analogs and/or chimeras thereof, comprising a polynucleotide of the present invention.

A polynucleotide of the present invention is inclusive of those in Table 1 and:

(a) an isolated polynucleotide encoding a polypeptide of the present invention such as those referenced in Table 1, including exemplary polynucleotides of the present invention;

(b) an isolated polynucleotide which is the product of amplification from a plant nucleic acid library using primer pairs which selectively hybridize under stringent conditions to loci within a polynucleotide of the present invention;

(c) an isolated polynucleotide which selectively hybridizes to a polynucleotide of (a) or (b);

(d) an isolated polynucleotide having a specified sequence identity with polynucleotides of (a), (b) or (c);

(e) an isolated polynucleotide encoding a protein having a specified number of contiguous amino acids from a prototype polypeptide, wherein the protein is specifically recognized by antisera elicited by presentation of the protein and wherein the protein does not detectably immunoreact to antisera which has been fully immunosorbed with the protein;

(f) complementary sequences of polynucleotides of (a), (b), (c), (d) or (e);

(g) an isolated polynucleotide comprising at least a specific number of contiguous nucleotides from a polynucleotide of (a), (b), (c), (d), (e) or (f);

(h) an isolated polynucleotide from a full-length enriched cDNA library having the physico-chemical property of selectively hybridizing to a polynucleotide of (a), (b), (c), (d), (e), (f) or (g); and (i) an isolated polynucleotide made by the process of: 1) providing a full-length enriched nucleic acid library, 2) selectively hybridizing the polynucleotide to a polynucleotide of (a), (b), (c), (d), (e), (f), (g) or (h), thereby isolating the polynucleotide from the nucleic acid library.

A. Polynucleotides Encoding A Polypeptide of the Present Invention

As indicated in (a), above, the present invention provides isolated nucleic acids comprising a polynucleotide of the present invention, wherein the polynucleotide encodes a polypeptide of the present invention. Every nucleic acid sequence herein that encodes a polypeptide also, by reference to the genetic code, describes every possible silent variation of the nucleic acid. One of ordinary skill will recognize that each codon in a nucleic acid (except AUG, which is ordinarily the only codon for methionine; and UGG, which is ordinarily the only codon for tryptophan) can be modified to yield a functionally identical molecule. Thus, each silent variation of a nucleic acid which encodes a polypeptide of the present invention is implicit in each described polypeptide sequence and is within the scope of the present invention. Accordingly, the present invention includes polynucleotides of the present invention and polynucleotides encoding a polypeptide of the present invention.

B. Polynucleotides Amplified from a Plant Nucleic Acid Library

As indicated in (b), above, the present invention provides an isolated nucleic acid comprising a polynucleotide of the present invention, wherein the polynucleotides are amplified, under nucleic acid amplification conditions, from a plant nucleic acid library. Nucleic acid amplification conditions for each of the variety of amplification methods are well known to those of ordinary skill in the art. The plant nucleic acid library can be constructed from a monocot such as a cereal crop. Exemplary cereals include corn, sorghum, wheat, or rice. The plant nucleic acid library can also be constructed from a dicot such as soybean, alfalfa, or canola. *Zea mays* lines B73, PHRE1, A632, BMS-P2#10, W23, and Mo17 are known and publicly available. Other publicly known and available maize lines can be obtained from the Maize Genetics Cooperation (Urbana, Ill.). Wheat lines are available from the Wheat Genetics Resource Center (Manhattan, Kans.).

The nucleic acid library may be a cDNA library, a genomic library, or a library generally constructed from nuclear transcripts at any stage of intron processing. In optional embodiments, the cDNA library is constructed using an enriched full-length cDNA synthesis method. Examples of such methods include Oligo-Capping (Maruyama and Sugano, (1994) *Gene* 138:171-174), Biotinylated CAP Trapper (Carninci, et al., (1996) *Genomics* 37:327-336), and CAP Retention Procedure (Edery, et al., (1995) *Molecular and Cellular Biology* 15:3363-3371). Rapidly growing tissues or rapidly dividing cells are preferred for use as an mRNA source for construction of a cDNA library. Growth stages of corn are described in "How a Corn Plant Develops," Special Report No. 48, Iowa State University of Science and Technology Cooperative Extension Service, Ames, Iowa, Reprinted February 1993.

A polynucleotide of this embodiment (or subsequences thereof) can be obtained, for example, by using amplification primers which are selectively hybridized and primer extended, under nucleic acid amplification conditions, to at least two sites within a polynucleotide of the present invention, or to two sites within the nucleic acid which flank and comprise a polynucleotide of the present invention, or to a site within a polynucleotide of the present invention and a site within the nucleic acid which comprises it. Methods for obtaining 5' and/or 3' ends of a vector insert are well known in the art. See, e.g., RACE (Rapid Amplification of Complementary Ends) as described in Frohman, M. A., in PCR Protocols: A Guide to Methods and Applications, M. A. Innis, D. H. Gelfand, J. J. Sninsky, T. J. White, Eds. (Academic Press, Inc., San Diego), pp. 28-38 (1990)); see, also, U.S. Pat. No. 5,470,722, and *Current Protocols in Molecular Biology*, Unit 15.6, Ausubel, et al., Eds., Greene Publishing and Wiley-Interscience, New York (1995); Frohman and Martin, (1989) *Techniques* 1:165.

Optionally, the primers are complementary to a subsequence of the target nucleic acid which they amplify but may have a sequence identity ranging from about 85% to 99% relative to the polynucleotide sequence to which they are designed to anneal. As those skilled in the art will appreciate, the sites to which the primer pairs will selectively hybridize are chosen such that a single contiguous nucleic acid can be formed under the desired nucleic acid amplification conditions. The primer length as measured in contiguous nucleotides is selected from the group of integers consisting of from at least 15 to 50. Thus, the primers can be at least 15, 18, 20, 25, 30, 40 or 50 contiguous nucleotides in length. Those of skill will recognize that a lengthened primer sequence can be employed to increase specificity of binding (i.e., annealing) to a target sequence. A non-annealing sequence at the 5' end of a primer (a "tail") can be added, for example, to introduce a cloning site at the terminal ends of the amplicon.

The amplification products can be translated using expression systems well known to those of skill in the art. The resulting translation products can be confirmed as polypeptides of the present invention by, for example, assaying for the appropriate catalytic activity (e.g., specific activity and/or substrate specificity), or verifying the presence of one or more epitopes which are specific to a polypeptide of the present invention. Methods for protein synthesis from PCR-derived templates are known in the art and available commercially. See, e.g., Amersham Life Sciences, Inc, Catalog '97, p. 354.

C. Polynucleotides Which Selectively Hybridize to a Polynucleotide of (A) or (B)

As indicated in (c), above, the present invention provides isolated nucleic acids comprising polynucleotides of the present invention, wherein the polynucleotides selectively hybridize, under selective hybridization conditions, to a polynucleotide of sections (A) or (B) as discussed above. Thus, the polynucleotides of this embodiment can be used for isolating, detecting, and/or quantifying nucleic acids comprising the polynucleotides of (A) or (B). For example, polynucleotides of the present invention can be used to identify, isolate, or amplify partial or full-length clones in a deposited library. In some embodiments, the polynucleotides are genomic or cDNA sequences isolated or otherwise complementary to a cDNA from a dicot or monocot nucleic acid library. Exemplary species of monocots and dicots include, but are not limited to: maize, canola, soybean, cotton, wheat, sorghum, sunflower, alfalfa, oats, sugar cane, millet, barley and rice. The cDNA library comprises at least 50% to 95% full-length sequences (for example, at least 50%, 60%, 70%, 80%, 90% or 95% full-length sequences). The cDNA libraries can be normalized to increase the representation of rare sequences. See, e.g., U.S. Pat. No. 5,482,845. Low stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% to 80% sequence identity and can be employed to identify orthologous or paralogous sequences.

D. Polynucleotides Having a Specific Sequence Identity with the Polynucleotides of (A), (B) or (C)

As indicated in (d), above, the present invention provides isolated nucleic acids comprising polynucleotides of the present invention, wherein the polynucleotides have a specified identity at the nucleotide level to a polynucleotide as disclosed above in sections (A), (B) or (C), above. Identity can be calculated using, for example, the BLAST, CLUSTALW, or GAP programs under default conditions. The percentage of identity to a reference sequence is at least 60% and, rounded upwards to the nearest integer, can be expressed as an integer selected from the group of integers consisting of from 60 to 99. Thus, for example, the percentage of identity to a reference sequence can be at least 70%, 75%, 80%, 85%, 90% or 95%.

The polynucleotides/polypeptides of the present invention having a specified sequence identity with a polynucleotide/polypeptide of section (A), (B) or (C) can be of a length (measured in contiguous nucleotides or amino acids) selected from the group consisting of from 15 to the length of the polynucleotide/polypeptide of (A), (B) or (C) or any integer value in between. For example, the length of the polynucleotides or polypeptides can be 25, 50, 75, 100, 150, 200, 250, 300, 350, 400, 500, 750, 1000, 1250, 1500 or greater.

Optionally, the polynucleotides of this embodiment will encode a polypeptide that will share an epitope with a polypeptide encoded by the polynucleotides of sections (A), (B) or (C). Thus, these polynucleotides encode a first polypeptide which elicits production of antisera comprising antibodies which are specifically reactive to a second polypeptide encoded by a polynucleotide of (A), (B) or (C). However, the first polypeptide does not bind to antisera raised against itself when the antisera has been fully immunosorbed with the first polypeptide. Hence, the polynucleotides of this embodiment can be used to generate antibodies for use in, for example, the screening of expression libraries for nucleic acids comprising polynucleotides of (A), (B) or (C), or for purification of, or in immunoassays for, polypeptides encoded by the polynucleotides of (A), (B) or (C). The polynucleotides of this embodiment comprise nucleic acid sequences which can be employed for selective hybridization to a polynucleotide encoding a polypeptide of the present invention.

Screening polypeptides for specific binding to antisera can be conveniently achieved using peptide display libraries. This method involves the screening of large collections of peptides for individual members having the desired function or structure. Antibody screening of peptide display libraries is well known in the art. The displayed peptide sequences can be from 3 to 5000 or more amino acids in length, frequently from 5-100 amino acids long, and often from about 8 to 15 amino acids long. In addition to direct chemical synthetic methods for generating peptide libraries, several recombinant DNA methods have been described. One type involves the display of a peptide sequence on the surface of a bacteriophage or cell. Each bacteriophage or cell contains the nucleotide sequence encoding the particular displayed peptide sequence. Such methods are described in PCT Patent Publication Numbers 91/17271, 91/18980, 91/19818 and 93/08278. Other systems for generating libraries of peptides have aspects of both in vitro chemical synthesis and recombinant methods. See, PCT Patent Publication Numbers 92/05258, 92/14843 and 97/20078. See, also, U.S. Pat. Nos. 5,658,754 and 5,643,768. Peptide display libraries, vectors, and screening kits are commercially available from such suppliers as Invitrogen (Carlsbad, Calif.).

E. Polynucleotides Encoding a Protein Having a Subsequence from a Prototype Polypeptide and Cross-Reactive to the Prototype Polypeptide As indicated in (e), above, the present invention provides isolated nucleic acids comprising polynucleotides of the present invention, wherein the polynucleotides encode a protein having a subsequence of contiguous amino acids from a prototype polypeptide of the present invention such as are provided in (a), above. The length of contiguous amino acids from the prototype polypeptide is selected from the group of integers consisting of from at least 10 to the number of amino acids within the prototype sequence. Thus, for example, the polynucleotide can encode a polypeptide having a subsequence having at least 10, 15, 20, 25, 30, 35, 40, 45 or 50, contiguous amino acids from the prototype polypeptide. Further, the number of such subsequences encoded by a polynucleotide of the instant embodiment can be any integer selected from the group consisting of from 0 to 20, such as 2, 3, 4 or 5. The subsequences can be separated by any integer of nucleotides from 0 to the number of nucleotides in the sequence such as at least 5, 10, 15, 25, 50, 100 or 200 nucleotides.

The proteins encoded by polynucleotides of this embodiment, when presented as an immunogen, elicit the production of polyclonal antibodies which specifically bind to a prototype polypeptide such as but not limited to, a polypeptide encoded by the polynucleotide of (a) or (b), above. Generally, however, a protein encoded by a polynucleotide of this embodiment does not bind to antisera raised against the prototype polypeptide when the antisera has been fully immunosorbed with the prototype polypeptide. Methods of making and assaying for antibody binding specificity/affinity are well known in the art. Exemplary immunoassay formats include ELISA, competitive immunoassays, radioimmunoassays, Western blots, indirect immunofluorescent assays and the like.

In a preferred assay method, fully immunosorbed and pooled antisera which is elicited to the prototype polypeptide can be used in a competitive binding assay to test the protein. The concentration of the prototype polypeptide required to inhibit 50% of the binding of the antisera to the prototype polypeptide is determined. If the amount of the protein required to inhibit binding is less than twice the amount of the prototype protein, then the protein is said to specifically bind to the antisera elicited to the immunogen. Accordingly, the proteins of the present invention embrace allelic variants, conservatively modified variants, and minor recombinant modifications to a prototype polypeptide.

A polynucleotide of the present invention optionally encodes a protein having a molecular weight as the non-glycosylated protein within 20% of the molecular weight of the full-length non-glycosylated polypeptides of the present invention. Molecular weight can be readily determined by SDS-PAGE under reducing conditions. Optionally, the molecular weight is within 15% of a full length polypeptide of the present invention, more preferably within 10% or 5%, and most preferably within 3%, 2% or 1% of a full length polypeptide of the present invention.

Optionally, the polynucleotides of this embodiment will encode a protein having a specific enzymatic activity at least 50%, 60%, 80% or 90% of a cellular extract comprising the native, endogenous full-length polypeptide of the present invention. Further, the proteins encoded by polynucleotides of this embodiment will optionally have a substantially similar affinity constant ($K_m$) and/or catalytic activity (i.e., the microscopic rate constant, $k_{cat}$) as the native endogenous, full-length protein. Those of skill in the art will recognize that $k_{cat}/K_m$ value determines the specificity for competing substrates and is often referred to as the specificity constant. Proteins of this embodiment can have a $k_{cat}/K_m$ value at least 10% of a full-length polypeptide of the present invention as determined using the endogenous substrate of that polypeptide. Optionally, the $k_{cat}/K_m$ value will be at least 20%, 30%, 40%, 50%, and most preferably at least 60%, 70%, 80%, 90% or 95% the $k_{cat}/K_m$ value of the full-length polypeptide of the present invention. Determination of $k_{cat}$, $K_m$, and $k_{cat}/K_m$ can be determined by any number of means well known to those of skill in the art. For example, the initial rates (i.e., the first 5% or less of the reaction) can be determined using rapid mixing and sampling techniques (e.g., continuous-flow, stopped-flow, or rapid quenching techniques), flash photolysis, or relaxation methods (e.g., temperature jumps) in conjunction with such exemplary methods of measuring as spectrophotometry, spectrofluorimetry, nuclear magnetic resonance, or radioactive procedures. Kinetic values are conveniently obtained using a Lineweaver-Burk or Eadie-Hofstee plot.

F. Polynucleotides Complementary to the Polynucleotides of (A)-(E)

As indicated in (f), above, the present invention provides isolated nucleic acids comprising polynucleotides complementary to the polynucleotides of paragraphs A-E, above. As those of skill in the art will recognize, complementary sequences base-pair throughout the entirety of their length with the polynucleotides of sections (A)-(E) (i.e., have 100% sequence identity over their entire length). Complementary bases associate through hydrogen bonding in double stranded nucleic acids. For example, the following base pairs are complementary: guanine and cytosine; adenine and thymine; and adenine and uracil.

G. Polynucleotides which are Subsequences of the Polynucleotides of (A)-(F)

As indicated in (g), above, the present invention provides isolated nucleic acids comprising polynucleotides which comprise at least 15 contiguous bases from the polynucleotides of sections (A) through (F) as discussed above. The length of the polynucleotide is given as an integer selected from the group consisting of from at least 15 to the length of the nucleic acid sequence of which the polynucleotide is a subsequence. Thus, for example, polynucleotides of the present invention are inclusive of polynucleotides comprising at least 15, 20, 25, 30, 40, 50, 60, 75, 100, 200, 300, 400, 500, 600, 700, 800, 900 or 1000 contiguous nucleotides in length from the polynucleotides of (A)-(F). Optionally, the number of such subsequences encoded by a polynucleotide of the instant embodiment can be any integer selected from the group consisting of from 1 to 20, such as 2, 3, 4 or 5. The subsequences can be separated by any integer of nucleotides from 1 to the number of nucleotides in the sequence such as at least 5, 10, 15, 25, 50, 100 or 200 nucleotides.

Subsequences can be made by in vitro synthetic, in vitro biosynthetic, or in vivo recombinant methods. In optional embodiments, subsequences can be made by nucleic acid amplification. For example, nucleic acid primers will be constructed to selectively hybridize to a sequence (or its complement) within, or co-extensive with, the coding region.

A subsequence of the present invention can comprise structural characteristics of the sequence from which it is derived. Alternatively, a subsequence can lack certain structural characteristics of the larger sequence from which it is derived such as a poly (A) tail. Optionally, a subsequence from a polynucleotide encoding a polypeptide having at least one epitope in common with a prototype polypeptide sequence as provided in (a), above, may encode an epitope in common with the prototype sequence. Alternatively, the subsequence may not encode an epitope in common with the prototype sequence but can be used to isolate the larger sequence by, for example, nucleic acid hybridization with the sequence from which it is derived. Subsequences can be used to modulate or detect gene expression by introducing into the subsequences compounds which bind, intercalate, cleave and/or crosslink to nucleic acids. Exemplary compounds include acridine, psoralen, phenanthroline, naphthoquinone, daunomycin or chloroethylaminoaryl conjugates.

H. Polynucleotides from a Full-Length Enriched cDNA Library Having the Physico-Chemical Property of Selectively Hybridizing to a Polynucleotide of (A)-(G)

As indicated in (h), above, the present invention provides an isolated polynucleotide from a full-length enriched cDNA library having the physico-chemical property of selectively hybridizing to a polynucleotide of paragraphs (A), (B), (C), (D), (E), (F) or (G) as discussed above. Methods of constructing full-length enriched cDNA libraries are known in the art and discussed briefly below. The cDNA library comprises at least 50% to 95% full-length sequences (for example, at least 50%, 60%, 70%, 80%, 90% or 95% full-length sequences). The cDNA library can be constructed from a variety of tissues from a monocot or dicot at a variety of developmental stages. Exemplary species include maize, wheat, rice, canola, soybean, cotton, sorghum, sunflower, alfalfa, oats, sugar cane, millet, barley and rice. Methods of selectively hybridizing a polynucleotide from a full-length enriched library to a polynucleotide of the present invention are known to those of ordinary skill in the art. Any number of stringency conditions can be employed to allow for selective hybridization. In optional embodiments, the stringency allows for selective hybridization of sequences having at least 70%, 75%, 80%, 85%, 90%, 95% or 98% sequence identity over the length of the hybridized region.

I. Polynucleotide Products Made by a cDNA Isolation Process

As indicated in (I), above, the present invention provides an isolated polynucleotide made by the process of: 1) providing a full-length enriched nucleic acid library, 2) selectively hybridizing the polynucleotide to a polynucleotide of paragraphs (A), (B), (C), (D), (E), (F), (G) or (H) as discussed above, and thereby isolating the polynucleotide from the nucleic acid library. Full-length enriched nucleic acid libraries are constructed as discussed in paragraph (G) and below. Selective hybridization conditions are as discussed in paragraph (G). Nucleic acid purification procedures are well known in the art. Purification can be conveniently accomplished using solid-phase methods; such methods are well known to those of skill in the art and kits are available from commercial suppliers such as Advanced Biotechnologies (Surrey, UK). For example, a polynucleotide of paragraphs (A)-(H) can be immobilized to a solid support such as a membrane, bead, or particle. See, e.g., U.S. Pat. No. 5,667, 976. The polynucleotide product of the present process is selectively hybridized to an immobilized polynucleotide and the solid support is subsequently isolated from non-hybridized polynucleotides by methods including, but not limited to, centrifugation, magnetic separation, filtration, electrophoresis, and the like.

Construction of Nucleic Acids

The isolated nucleic acids of the present invention can be made using (a) standard recombinant methods, (b) synthetic techniques, or combinations thereof. In some embodiments, the polynucleotides of the present invention will be cloned, amplified, or otherwise constructed from a monocot such as corn, rice, or wheat, or a dicot such as soybean.

The nucleic acids may conveniently comprise sequences in addition to a polynucleotide of the present invention. For example, a multi-cloning site comprising one or more endonuclease restriction sites may be inserted into the nucleic acid to aid in isolation of the polynucleotide. Also, translatable sequences may be inserted to aid in the isolation of the translated polynucleotide of the present invention. For example, a hexa-histidine marker sequence provides a convenient means to purify the proteins of the present invention. A polynucleotide of the present invention can be attached to a vector, adapter, or linker for cloning and/or expression of a polynucleotide of the present invention. Additional sequences may be added to such cloning and/or expression sequences to optimize their function in cloning and/or expression, to aid in isolation of the polynucleotide, or to improve the introduction of the polynucleotide into a cell. Typically, the length of a nucleic acid of the present invention less the length of its polynucleotide of the present invention is less than 20 kilobase pairs, often less than 15 kb, and frequently less than 10 kb. Use of cloning vectors, expression vectors, adapters, and linkers is well known and extensively described in the art. For a description of various nucleic acids see, for example, Stratagene Cloning Systems, Catalogs 1999 (La Jolla, Calif.); and, Amersham Life Sciences, Inc, Catalog '99 (Arlington Heights, Ill.).

A Recombinant Methods for Constructing Nucleic Acids

The isolated nucleic acid compositions of this invention, such as RNA, cDNA, genomic DNA, or a hybrid thereof, can be obtained from plant biological sources using any number of cloning methodologies known to those of skill in the art. In some embodiments, oligonucleotide probes which selectively hybridize, under stringent conditions, to the polynucleotides of the present invention are used to identify the desired sequence in a cDNA or genomic DNA library. Isolation of RNA and construction of cDNA and genomic libraries are well known to those of ordinary skill in the art. See, e.g., *Plant Molecular Biology: A Laboratory Manual*, Clark, Ed., Springer-Verlag, Berlin (1997); and *Current Protocols in Molecular Biology*, Ausubel, et al., Eds., Greene Publishing and Wiley-Interscience, New York (1995).

A1. Full-Length Enriched cDNA Libraries

A number of cDNA synthesis protocols have been described which provide enriched full-length cDNA libraries. Enriched full-length cDNA libraries are constructed to comprise at least 60%, and more preferably at least 70%, 80%, 90% or 95% full-length inserts amongst clones containing inserts. The length of insert in such libraries can be at least 2, 3, 4, 5, 6, 7, 8, 9, 10 or more kilobase pairs. Vectors to accommodate inserts of these sizes are known in the art and available commercially. See, e.g., Stratagene's lambda ZAP Express (cDNA cloning vector with 0 to 12 kb cloning capacity). An exemplary method of constructing a greater than 95% pure full-length cDNA library is described by Carninci, et al., (1996) *Genomics,* 37:327-336. Other methods for producing full-length libraries are known in the art. See, e.g., Edery, et al., (1995) *Mol. Cell. Biol.,* 15(6):3363-3371; and, PCT Application Number WO 96/34981.

A2 Normalized or Subtracted cDNA Libraries

A non-normalized cDNA library represents the mRNA population of the tissue from which it was made. Since unique clones are out-numbered by clones derived from highly expressed genes, their isolation can be laborious. Normalization of a cDNA library is the process of creating a library in which each clone is more equally represented. Construction of normalized libraries is described in Ko, (1990) *Nucl. Acids. Res.* 18(19):5705-5711; Patanjali, et al., (1991) *Proc. Natl. Acad. U.S.A.* 88:1943-1947; U.S. Pat. Nos. 5,482,685; 5,482, 845 and 5,637,685. In an exemplary method described by Soares, et al., normalization resulted in reduction of the abundance of clones from a range of four orders of magnitude to a narrow range of only 1 order of magnitude. *Proc. Natl. Acad. Sci. USA* 91:9228-9232 (1994).

Subtracted cDNA libraries are another means to increase the proportion of less abundant cDNA species. In this procedure, cDNA prepared from one pool of mRNA is depleted of sequences present in a second pool of mRNA by hybridization. The cDNA:mRNA hybrids are removed and the remaining un-hybridized cDNA pool is enriched for sequences unique to that pool. See, Foote, et al., *Plant Molecular Biology: A Laboratory Manual*, Clark, Ed., Springer-Verlag, Berlin (1997); Kho and Zarbl, (1991) *Technique,* 3(2):58-63; Sive and St. John, (1988) *Nucl. Acids Res.* 16(22):10937; *Current Protocols in Molecular Biology*, Ausubel, et al., Eds., Greene Publishing and Wiley-Interscience, New York (1995); and, Swaroop, et al., (1991) *Nucl. Acids Res.,* 19(8):1954. cDNA subtraction kits are commercially available. See, e.g., PCR-Select (Clontech, Palo Alto, Calif.).

To construct genomic libraries, large segments of genomic DNA are generated by fragmentation, e.g. using restriction endonucleases, and are ligated with vector DNA to form concatemers that can be packaged into the appropriate vector. Methodologies to accomplish these ends, and sequencing methods to verify the sequence of nucleic acids, are well known in the art. Examples of appropriate molecular biological techniques and instructions sufficient to direct persons of skill through many construction, cloning, and screening methodologies are found in Sambrook, et al., *Molecular Cloning: A Laboratory Manual*, 2nd Ed., Cold Spring Harbor Laboratory Vols. 1-3 (1989), Methods in Enzymology, Vol.

152: *Guide to Molecular Cloning Techniques*, Berger and Kimmel, Eds., San Diego: Academic Press, Inc. (1987), *Current Protocols in Molecular Biology*, Ausubel, et al., Eds., Greene Publishing and Wiley-Interscience, New York (1995); *Plant Molecular Biology: A Laboratory Manual*, Clark, Ed., Springer-Verlag, Berlin (1997). Kits for construction of genomic libraries are also commercially available.

The cDNA or genomic library can be screened using a probe based upon the sequence of a polynucleotide of the present invention such as those disclosed herein. Probes may be used to hybridize with genomic DNA or cDNA sequences to isolate homologous genes in the same or different plant species. Those of skill in the art will appreciate that various degrees of stringency of hybridization can be employed in the assay, and either the hybridization or the wash medium can be stringent.

The nucleic acids of interest can also be amplified from nucleic acid samples using amplification techniques. For instance, polymerase chain reaction (PCR) technology can be used to amplify the sequences of polynucleotides of the present invention and related genes directly from genomic DNA or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. The T4 gene 32 protein (Boehringer Mannheim) can be used to improve yield of long PCR products.

PCR-based screening methods have been described. Wilfinger, et al., describe a PCR-based method in which the longest cDNA is identified in the first step so that incomplete clones can be eliminated from study. *BioTechniques*, 22(3): 481-486 (1997). Such methods are particularly effective in combination with a full-length cDNA construction methodology, above.

B. Synthetic Methods for Constructing Nucleic Acids

The isolated nucleic acids of the present invention can also be prepared by direct chemical synthesis by methods such as the phosphotriester method of Narang, et al., (1979) *Meth. Enzymol.* 68:90-99; the phosphodiester method of Brown, et al., (1979) *Meth. Enzymol.* 68:109-151; the diethylphosphoramidite method of Beaucage, et al., (1981) *Tetra. Lett.* 22:1859-1862; the solid phase phosphoramidite triester method described by Beaucage and Caruthers, (1981) *Tetra. Letts.* 22(20):1859-1862, e.g., using an automated synthesizer, e.g., as described in Needham-VanDevanter, et al., (1984) *Nucleic Acids Res.* 12:6159-6168; and, the solid support method of U.S. Pat. No. 4,458,066. Chemical synthesis generally produces a single-stranded oligonucleotide. This may be converted into double-stranded DNA by hybridization with a complementary sequence or by polymerization with a DNA polymerase using the single strand as a template. One of skill will recognize that while chemical synthesis of DNA is best employed for sequences of about 100 bases or less, longer sequences may be obtained by the ligation of shorter sequences.

Recombinant Expression Cassettes

The present invention further provides recombinant expression cassettes comprising a nucleic acid of the present invention. A nucleic acid sequence coding for the desired polypeptide of the present invention, for example a cDNA or a genomic sequence encoding a full-length polypeptide of the present invention, can be used to construct a recombinant expression cassette which can be introduced into the desired host cell. A recombinant expression cassette will typically comprise a polynucleotide of the present invention operably linked to transcriptional initiation regulatory sequences which will direct the transcription of the polynucleotide in the intended host cell, such as within tissues of a transformed plant.

For example, plant expression vectors may include (1) a cloned plant gene under the transcriptional control of 5' and 3' regulatory sequences and (2) a dominant selectable marker. Such plant expression vectors may also contain, if desired, a promoter regulatory region (e.g., one conferring inducible or constitutive, environmentally- or developmentally-regulated, or cell- or tissue-specific/selective expression), a transcription initiation start site, a ribosome binding site, an RNA processing signal, a transcription termination site, and/or a polyadenylation signal.

A plant promoter fragment can be employed which will direct expression of a polynucleotide of the present invention in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumefaciens*, the ubiquitin 1 promoter, the Smas promoter, the cinnamyl alcohol dehydrogenase promoter (U.S. Pat. No. 5,683,439), the Nos promoter, the pEmu promoter, the rubisco promoter, and the GRP1-8 promoter.

Alternatively, the plant promoter can direct expression of a polynucleotide of the present invention in a specific tissue or may be otherwise under more precise environmental or developmental control. Such promoters are referred to here as "inducible" promoters. Environmental conditions that may effect transcription by inducible promoters include pathogen attack, anaerobic conditions, or the presence of light. Examples of inducible promoters are the Adh1 promoter which is inducible by hypoxia or cold stress, the Hsp70 promoter which is inducible by heat stress, and the PPDK promoter which is inducible by light.

Examples of promoters under developmental control include promoters that initiate transcription only, or preferentially, in certain tissues, such as leaves, roots, fruit, seeds, or flowers. Exemplary promoters include the anther specific promoter 5126 (U.S. Pat. Nos. 5,689,049 and 5,689,051), glob-1 promoter, and gamma-zein promoter. The present invention provides promoters with expression limited to, or enhanced in, maize silks, including the gl2 promoter (SEQ ID NO: 1 and SEQ ID NO: 26). The operation of a promoter may also vary depending on its location in the genome. Thus, an inducible promoter may become fully or partially constitutive in certain locations.

Both heterologous and non-heterologous (i.e., endogenous) promoters can be employed to direct expression of the nucleic acids of the present invention. These promoters can also be used, for example, in recombinant expression cassettes to drive expression of antisense nucleic acids to reduce, increase, or alter concentration and/or composition of the proteins of the present invention in a desired tissue. Thus, in some embodiments, the nucleic acid construct will comprise a promoter, functional in a plant cell, operably linked to a polynucleotide of the present invention. Promoters useful in these embodiments include the endogenous promoters driving expression of a polypeptide of the present invention.

In some embodiments, isolated nucleic acids which serve as promoter or enhancer elements can be introduced in the appropriate position (generally upstream) of a non-heterologous form of a polynucleotide of the present invention so as to up- or down-regulate expression of a polynucleotide of the present invention. For example, endogenous promoters can be altered in vivo by mutation, deletion, and/or substitution (see, Kmiec, U.S. Pat. No. 5,565,350; Zarling, et al., PCT/US93/03868), or isolated promoters can be introduced into a plant cell in the proper orientation and distance from a cognate gene of a polynucleotide of the present invention so as to control the expression of the gene. Gene expression can be modulated under conditions suitable for plant growth so as to alter the total concentration and/or alter the composition of the polypeptides of the present invention in plant cell. Thus, the present invention provides compositions, and methods for making, heterologous promoters and/or enhancers operably linked to a native, endogenous (i.e., non-heterologous) form of a polynucleotide of the present invention.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added can be derived from, for example, the nopaline synthase or octopine synthase genes, or alternatively from another plant gene, or less preferably from any other eukaryotic gene.

An intron sequence can be added to the 5' untranslated region or the coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold. Buchman and Berg, (1988) *Mol. Cell. Biol.* 8:4395-4405; Callis, et al., (1987) *Genes Dev.* 1:1183-1200. Such intron enhancement of gene expression is typically greatest when placed near the 5' end of the transcription unit. Use of maize introns Adh1-S intron 1, 2 and 6, the Bronze-1 intron are known in the art. See, generally, *The Maize Handbook*, Chapter 116, Freeling and Walbot, Eds., Springer, New York (1994). The vector comprising the sequences from a polynucleotide of the present invention will typically comprise a marker gene which confers a selectable phenotype on plant cells. Typical vectors useful for expression of genes in higher plants are well known in the art and include vectors derived from the tumor-inducing (Ti) plasmid of *Agrobacterium tumefaciens* described by Rogers, et al., (1987) *Meth. in Enzymol.* 153:253-277.

A polynucleotide of the present invention can be expressed in either sense or anti-sense orientation as desired. It will be appreciated that control of gene expression in either sense or anti-sense orientation can have a direct impact on the observable plant characteristics. Antisense technology can be conveniently used to inhibit gene expression in plants. To accomplish this, a nucleic acid segment from the desired gene is cloned and operably linked to a promoter such that the anti-sense strand of RNA will be transcribed. The construct is then transformed into plants and the antisense strand of RNA is produced. In plant cells, it has been shown that antisense RNA inhibits gene expression by preventing the accumulation of mRNA which encodes the enzyme of interest, see, e.g., Sheehy, et al., (1988) *Proc. Nat'l. Acad. Sci. (USA)* 85:8805-8809; and Hiatt, et al., U.S. Pat. No. 4,801,340.

Another method of suppression is sense suppression (i.e., co-suppression). Introduction of nucleic acid configured in the sense orientation has been shown to be an effective means by which to block the transcription of target genes. For an example of the use of this method to modulate expression of endogenous genes, see, Napoli, et al., (1990) *The Plant Cell* 2:279-289 and U.S. Pat. No. 5,034,323.

Catalytic RNA molecules or ribozymes can also be used to inhibit expression of plant genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs. The design and use of target RNA-specific ribozymes is described in Haseloff, et al., (1988) *Nature* 334:585-591.

A variety of cross-linking agents, alkylating agents and radical generating species as pendant groups on polynucleotides of the present invention can be used to bind, label, detect, and/or cleave nucleic acids. For example, Vlassov, et al., (1986) *Nucleic Acids Res* 14:4065-4076, describe covalent bonding of a single-stranded DNA fragment with alkylating derivatives of nucleotides complementary to target sequences. A report of similar work by the same group is that by Knorre, et al., (1985) *Biochimie* 67:785-789. Iverson and Dervan also showed sequence-specific cleavage of single-stranded DNA mediated by incorporation of a modified nucleotide which was capable of activating cleavage (*J Am Chem Soc* (1987) 109:1241-1243). Meyer, et al., (1989) *J Am Chem Soc* 111:8517-8519, effect covalent crosslinking to a target nucleotide using an alkylating agent complementary to the single-stranded target nucleotide sequence. A photoactivated crosslinking to single-stranded oligonucleotides mediated by psoralen was disclosed by Lee, et al., (1988) *Biochemistry* 27:3197-3203. Use of crosslinking in triple-helix forming probes was also disclosed by Home, et al., (1990) *J Am Chem Soc* 112:2435-2437. Use of N4, N4-ethanocytosine as an alkylating agent to crosslink to single-stranded oligonucleotides has also been described by Webb and Matteucci, (1986) *J Am Chem Soc* 108:2764-2765; Nucleic Acids Res (1986) 14:7661-7674; Feteritz, et al., (1991) *J. Am. Chem. Soc.* 113:4000. Various compounds to bind, detect, label, and/or cleave nucleic acids are known in the art. See, for example, U.S. Pat. Nos. 5,543,507; 5,672,593; 5,484,908; 5,256,648 and 5,681,941.

Proteins

The isolated proteins of the present invention comprise a polypeptide having at least 10 amino acids from a polypeptide of the present invention (or conservative variants thereof) such as those encoded by any one of the polynucleotides of the present invention as discussed more fully above (e.g., Table 1). The proteins of the present invention or variants thereof can comprise any number of contiguous amino acid residues from a polypeptide of the present invention, wherein that number is selected from the group of integers consisting of from 10 to the number of residues in a full-length polypeptide of the present invention. Optionally, this subsequence of contiguous amino acids is at least 15, 20, 25, 30, 35 or 40 amino acids in length, often at least 50, 60, 70, 80 or 90 amino acids in length. Further, the number of such subsequences can be any integer selected from the group consisting of from 1 to 20, such as 2, 3, 4 or 5.

The present invention further provides a protein comprising a polypeptide having a specified sequence identity/similarity with a polypeptide of the present invention. The percentage of sequence identity/similarity is an integer selected from the group consisting of from 50 to 99. Exemplary sequence identity/similarity values include 60%, 65%, 70%, 75%, 80%, 85%, 90% and 95%. Sequence identity can be determined using, for example, the GAP, CLUSTALW or BLAST programs.

As those of skill will appreciate, the present invention includes, but is not limited to, catalytically active polypeptides of the present invention (i.e., enzymes). Catalytically active polypeptides have a specific activity of at least 20%, 30% or 40%, and preferably at least 50%, 60% or 70%, and most preferably at least 80%, 90% or 95% that of the native (non-synthetic), endogenous polypeptide. Further, the substrate specificity ($k_{cat}/K_m$) is optionally substantially similar to the native (non-synthetic), endogenous polypeptide. Typically, the $K_m$ will be at least 30%, 40% or 50%, that of the native (non-synthetic), endogenous polypeptide; and more preferably at least 60%, 70%, 80% or 90%. Methods of assaying and quantifying measures of enzymatic activity and substrate specificity ($k_{cat}/K_m$) are well known to those of skill in the art.

Expression of Proteins in Host Cells

Using the nucleic acids of the present invention, one may express a protein of the present invention in a recombinantly engineered cell such as bacteria, yeast, insect, mammalian, or preferably plant cells. The cells produce the protein in a non-natural condition (e.g., in quantity, composition, location, and/or time), because they have been genetically altered through human intervention to do so.

It is expected that those of skill in the art are knowledgeable in the numerous expression systems available for expression of a nucleic acid encoding a protein of the present invention. No attempt to describe in detail the various methods known for the expression of proteins in prokaryotes or eukaryotes will be made.

In brief summary, the expression of isolated nucleic acids encoding a protein of the present invention will typically be achieved by operably linking, for example, the DNA or cDNA to a promoter, followed by incorporation into an expression vector. The vector can be suitable for replication and integration in either prokaryotes or eukaryotes. Typical expression vectors contain transcription and translation terminators, initiation sequences, and promoters useful for regulation of the expression of the DNA encoding a protein of the present invention. To obtain high level expression of a cloned gene, it is desirable to construct expression vectors which contain, at the minimum, a strong promoter to direct transcription, a ribosome binding site for translational initiation, and a transcription/translation terminator. One of skill would recognize that modifications can be made to a protein of the present invention without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located purification sequences. Restriction sites or termination codons can also be introduced.

Synthesis of Proteins

The proteins of the present invention can be constructed using non-cellular synthetic methods. Solid phase synthesis of proteins of less than about 50 amino acids in length may be accomplished by attaching the C-terminal amino acid of the sequence to an insoluble support followed by sequential addition of the remaining amino acids in the sequence. Techniques for solid phase synthesis are described by Barany and Merrifield, Solid-Phase Peptide Synthesis, pp. 3-284 in *The Peptides: Analysis, Synthesis, Biology. Vol. 2: Special Methods in Peptide Synthesis, Part A.*; Merrifield, et al., (1963) *J. Am. Chem. Soc.* 85: 2149-2156, and Stewart, et al., *Solid Phase Peptide Synthesis*, 2nd ed., Pierce Chem. Co., Rockford, Ill. (1984). Proteins of greater length may be synthesized by condensation of the amino and carboxy termini of shorter fragments. Methods of forming peptide bonds by activation of a carboxy terminal end (e.g., by the use of the coupling reagent N,N'-dicycylohexylcarbodiimide) are known to those of skill.

Purification of Proteins

The proteins of the present invention may be purified by standard techniques well known to those of skill in the art. Recombinantly produced proteins of the present invention can be directly expressed or expressed as a fusion protein. The recombinant protein is purified by a combination of cell lysis (e.g., sonication, French press) and affinity chromatography. For fusion products, subsequent digestion of the fusion protein with an appropriate proteolytic enzyme releases the desired recombinant protein.

The proteins of this invention, recombinant or synthetic, may be purified to substantial purity by standard techniques well known in the art, including detergent solubilization, selective precipitation with such substances as ammonium sulfate, column chromatography, immunopurification methods, and others. See, for instance, R. Scopes, *Protein Purification Principles and Practice*, Springer-Verlag: New York (1982); Deutscher, *Guide to Protein Purification*, Academic Press (1990). For example, antibodies may be raised to the proteins as described herein. Purification from *E. coli* can be achieved following procedures described in U.S. Pat. No. 4,511,503. The protein may then be isolated from cells expressing the protein and further purified by standard protein chemistry techniques as described herein. Detection of the expressed protein is achieved by methods known in the art, including, for example, radioimmunoassays, Western blotting techniques or immunoprecipitation.

Introduction of Nucleic Acids Into Host Cells

The method of introducing a nucleic acid of the present invention into a host cell is not critical to the instant invention. Transformation or transfection methods are conveniently used. Accordingly, a wide variety of methods have been developed to insert a DNA sequence into the genome of a host cell to obtain the transcription and/or translation of the sequence to effect phenotypic changes in the organism. Thus, any method which provides for effective introduction of a nucleic acid may be employed.

A. Plant Transformation

A nucleic acid comprising a polynucleotide of the present invention is optionally introduced into a plant. Generally, the polynucleotide will first be incorporated into a recombinant expression cassette or vector. Isolated nucleic acid acids of the present invention can be introduced into plants according to techniques known in the art. Techniques for transforming a wide variety of higher plant species are well known and described in the technical, scientific, and patent literature. See, for example, Weising, et al., (1988) *Ann. Rev. Genet.* 22:421-477. For example, the DNA construct may be introduced directly into the genomic DNA of the plant cell using techniques such as electroporation, polyethylene glycol (PEG), poration, particle bombardment, silicon fiber delivery, or microinjection of plant cell protoplasts or embryogenic callus. See, e.g., Tomes, et al., Direct DNA Transfer into Intact Plant Cells Via Microprojectile Bombardment. pp. 197-213 in Plant Cell, Tissue and Organ Culture, Fundamental Methods. eds. O. L. Gamborg and G. C. Phillips, Springer-Verlag Berlin Heidelberg New York, 1995; see, U.S. Pat. No. 5,990,387. The introduction of DNA constructs using PEG precipitation is described in Paszkowski, et al., (1984) *Embo J.* 3:2717-2722. Electroporation techniques are described in Fromm, et al., (1985) *Proc. Natl. Acad. Sci.* (*USA*) 82:5824. Ballistic transformation techniques are described in Klein, et al., (1987) *Nature* 327:70-73.

*Agrobacterium tumefaciens*-mediated transformation techniques are well described in the scientific literature. See, for example, Horsch, et al., (1984) *Science* 233:496-498; Fraley, et al., (1983) *Proc. Natl. Acad. Sci. (USA)* 80:4803; and *Plant Molecular Biology: A Laboratory Manual*, Chapter 8, Clark, Ed., Springer-Verlag, Berlin (1997). The DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. See, U.S. Pat. No. 5,591,616. Although *Agrobacterium* is useful primarily in dicots, certain monocots can be transformed by *Agrobacterium*. For instance, *Agrobacterium* transformation of maize is described in U.S. Pat. No. 5,550,318.

Other methods of transfection or transformation include (1) *Agrobacterium rhizogenes*-mediated transformation (see, e.g., Lichtenstein and Fuller In: Genetic Engineering, vol. 6, P W J Rigby, Ed., London, Academic Press, 1987; and Lichtenstein, C. P., and Draper, J., In: DNA Cloning, Vol. II, D. M. Glover, Ed., Oxford, IRI Press, 1985), Application PCT/US87/02512 (WO 88/02405 published Apr. 7, 1988) describes the use of *A. rhizogenes* strain A4 and its Ri plasmid along with *A. tumefaciens* vectors pARC8 or pARC16; (2) liposome-mediated DNA uptake (see, e.g., Freeman, et al., (1984) *Plant Cell Physiol.* 25:1353); (3) the vortexing method (see, e.g., Kindle, (1990) *Proc. Natl. Acad. Sci., (USA)* 87:1228).

DNA can also be introduced into plants by direct DNA transfer into pollen as described by Zhou, et al., (1983) *Methods in Enzymology* 101:433; Hess, (1987) *Intern Rev. Cytol.* 107:367; Luo, et al., (1988) *Plant Mol. Biol. Reporter* 6:165. Expression of polypeptide coding genes can be obtained by injection of the DNA into reproductive organs of a plant as described by Pena, et al., (1987) *Nature* 325:274. DNA can also be injected directly into the cells of immature embryos and rehydrated desiccated embryos as described by Neuhaus, et al., (1987) *Theor. Appl. Genet.* 75:30; and Benbrook, et al., in *Proceedings Bio Expo* 1986, Butterworth, Stoneham, Mass., pp. 27-54 (1986). A variety of plant viruses that can be employed as vectors are known in the art and include cauliflower mosaic virus (CaMV), geminivirus, brome mosaic virus, and tobacco mosaic virus.

B. Transfection of Prokaryotes, Lower Eukaryotes, and Animal Cells

Animal and lower eukaryotic (e.g., yeast) host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation, biolistics, and micro-injection of the DNA directly into the cells. The transfected cells are cultured by means well known in the art. Kuchler, *Biochemical Methods in Cell Culture and Virology*, Dowden, Hutchinson and Ross, Inc. (1977).

Transgenic Plant Regeneration

Plant cells which directly result or are derived from the nucleic acid introduction techniques can be cultured to regenerate a whole plant which possesses the introduced genotype. Such regeneration techniques often rely on manipulation of certain phytohormones in a tissue culture growth medium. Plants cells can be regenerated, e.g., from single cells, callus tissue or leaf discs according to standard plant tissue culture techniques. It is well known in the art that various cells, tissues, and organs from almost any plant can be successfully cultured to regenerate an entire plant. Plant regeneration from cultured protoplasts is described in Evans, et al., *Protoplasts Isolation and Culture, Handbook of Plant Cell Culture*, Macmillan Publishing Company, New York, pp. 124-176 (1983); and Binding, *Regeneration of Plants, Plant Protoplasts*, CRC Press, Boca Raton, pp. 21-73 (1985).

The regeneration of plants from either single plant protoplasts or various explants is well known in the art. See, for example, *Methods for Plant Molecular Biology*, Weissbach and Weissbach, eds., Academic Press, Inc., San Diego, Calif. (1988). This regeneration and growth process includes the steps of selection of transformant cells and shoots, rooting the transformant shoots and growth of the plantlets in soil. For maize cell culture and regeneration see generally, *The Maize Handbook*, Freeling and Walbot, Eds., Springer, New York (1994); *Corn and Corn Improvement*, $3^{rd}$ edition, Sprague and Dudley Eds., American Society of Agronomy, Madison, Wis. (1988). For transformation and regeneration of maize, see, Gordon-Kamm, et al., (1990) *The Plant Cell* 2:603-618.

The regeneration of plants containing the polynucleotide of the present invention and introduced by *Agrobacterium* from leaf explants can be achieved as described by Horsch, et al., (1985) *Science* 227:1229-1231. In this procedure, transformants are grown in the presence of a selection agent and in a medium that induces the regeneration of shoots in the plant species being transformed as described by Fraley, et al., (1983) *Proc. Natl. Acad. Sci. USA* 80:4803. This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

One of skill will recognize that after the recombinant expression cassette is stably incorporated in transgenic plants and confirmed to be operable, it can be introduced into other plants by sexual crossing. Any of a number of standard breeding techniques can be used, depending upon the species to be crossed. In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self crossed to produce a homozygous inbred plant. The inbred plant produces seed containing the newly introduced nucleic acid. These seeds can be grown to produce plants with the selected phenotype. Parts obtained from the regenerated plant, such as flowers, seeds, leaves, branches, fruit, and the like are included in the invention, provided that these parts comprise cells comprising the isolated nucleic acid of the present invention. Progeny, variants, and mutants of the regenerated plants are also included within the scope of the invention, provided that these parts comprise the introduced nucleic acid sequences. Transgenic plants expressing a polynucleotide of the present invention can be screened for transmission of the nucleic acid of the present invention by, for example, standard immunoblot and DNA detection techniques. Expression at the RNA level can be determined initially to identify and quantitate expression-positive plants. Standard techniques for RNA analysis can be employed and include PCR amplification assays using oligonucleotide primers designed to amplify only the heterologous RNA templates and solution hybridization assays using heterologous nucleic acid-specific probes. The RNA-positive plants can then be analyzed for protein expression by Western immunoblot analysis using the specifically reactive antibodies of the present invention. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

A preferred embodiment is a transgenic plant that is homozygous for the added heterologous nucleic acid; i.e., a transgenic plant that contains two added nucleic acid sequences, one gene at the same locus on each chromosome of a chromosome pair. A homozygous transgenic plant can be obtained by sexually mating (selfing) a heterozygous transgenic plant that contains a single added heterologous nucleic acid, germinating some of the seed produced and analyzing the resulting plants for altered expression of a polynucleotide of the present invention relative to a control plant (i.e., native, non-transgenic). Back-crossing to a parental plant and out-crossing with a non-transgenic plant are also contemplated.

Modulating Polypeptide Levels and/or Composition

The present invention further provides a method for modulating (i.e., increasing or decreasing) the concentration or ratio of the polypeptides of the present invention in a plant or part thereof. Modulation can be effected by increasing or decreasing the concentration and/or the ratio of the polypeptides of the present invention in a plant. The method comprises introducing into a plant cell a recombinant expression cassette comprising a polynucleotide of the present invention as described above to obtain a transgenic plant cell, culturing the transgenic plant cell under transgenic plant cell growing conditions, and inducing or repressing expression of a polynucleotide of the present invention in the transgenic plant for a time sufficient to modulate concentration and/or the ratios of the polypeptides in the transgenic plant or plant part.

In some embodiments, the concentration and/or ratios of polypeptides of the present invention in a plant may be modulated by altering, in vivo or in vitro, the promoter of a gene to up- or down-regulate gene expression. In some embodiments, the coding regions of native genes of the present invention can be altered via substitution, addition, insertion, or deletion to decrease activity of the encoded enzyme. See, e.g., Kmiec, U.S. Pat. No. 5,565,350; Zarling, et al., PCT/US93/03868. And in some embodiments, an isolated nucleic acid (e.g., a vector) comprising a promoter sequence is transfected into a plant cell. Subsequently, a plant cell comprising the promoter operably linked to a polynucleotide of the present invention is selected for by means known to those of skill in the art such as, but not limited to, Southern blot, DNA sequencing, or PCR analysis using primers specific to the promoter and to the gene and detecting amplicons produced therefrom. A plant or plant part altered or modified by the foregoing embodiments is grown under plant-forming conditions for a time sufficient to modulate the concentration and/or ratios of polypeptides of the present invention in the plant. Plant-forming conditions are well known in the art and discussed briefly, supra.

In general, concentration or the ratios of the polypeptides is increased or decreased by at least 5%, 10%, 20%, 30%, 40%, 50%, 60%, 70%, 80% or 90% relative to a native control plant, plant part, or cell lacking the aforementioned recombinant expression cassette. Modulation in the present invention may occur during and/or subsequent to growth of the plant to the desired stage of development. Modulating nucleic acid expression temporally and/or in particular tissues can be controlled by employing the appropriate promoter operably linked to a polynucleotide of the present invention in, for example, sense or antisense orientation as discussed in greater detail, supra. Induction of expression of a polynucleotide of the present invention can also be controlled by exogenous administration of an effective amount of inducing compound. Inducible promoters and inducing compounds which activate expression from these promoters are well known in the art. In preferred embodiments, the polypeptides of the present invention are modulated in monocots, particularly maize.

UTRs and Codon Preference

In general, translational efficiency has been found to be regulated by specific sequence elements in the 5' non-coding or untranslated region (5' UTR) of the RNA. Positive sequence motifs include translational initiation consensus sequences (Kozak, (1987) *Nucleic Acids Res.* 15:8125) and the 7-methylguanosine cap structure (Drummond, et al., (1985) *Nucleic Acids Res.* 13:7375). Negative elements include stable intramolecular 5' UTR stem-loop structures (Muesing, et al., (1987) *Cell* 48:691) and AUG sequences or short open reading frames preceded by an appropriate AUG in the 5' UTR (Kozak, supra, Rao, et al., (1988) *Mol. and Cell. Biol.* 8:284). Accordingly, the present invention provides 5' and/or 3' untranslated regions for modulation of translation of heterologous coding sequences.

Further, the polypeptide-encoding segments of the polynucleotides of the present invention can be modified to alter codon usage. Altered codon usage can be employed to alter translational efficiency and/or to optimize the coding sequence for expression in a desired host such as to optimize the codon usage in a heterologous sequence for expression in maize. Codon usage in the coding regions of the polynucleotides of the present invention can be analyzed statistically using commercially available software packages such as "Codon Preference" available from the University of Wisconsin Genetics Computer Group (see, Devereaux, et al., (1984) *Nucleic Acids Res.* 12:387-395) or MacVector 4.1 (Eastman Kodak Co., New Haven, Conn.). Thus, the present invention provides a codon usage frequency characteristic of the coding region of at least one of the polynucleotides of the present invention. The number of polynucleotides that can be used to determine a codon usage frequency can be any integer from 1 to the number of polynucleotides of the present invention as provided herein. Optionally, the polynucleotides will be full-length sequences. An exemplary number of sequences for statistical analysis can be at least 1, 5, 10, 20, 50 or 100.

Sequence Shuffling

The present invention provides methods for sequence shuffling using polynucleotides of the present invention, and compositions resulting therefrom. Sequence shuffling is described in PCT Publication Number WO 97/20078. See, also, Zhang, et al., (1997) *Proc. Natl. Acad. Sci. USA* 94:4504-4509. Generally, sequence shuffling provides a means for generating libraries of polynucleotides having a desired characteristic which can be selected or screened for. Libraries of recombinant polynucleotides are generated from a population of related sequence polynucleotides which comprise sequence regions which have substantial sequence identity and can be homologously recombined in vitro or in vivo. The population of sequence-recombined polynucleotides comprises a subpopulation of polynucleotides which possess desired or advantageous characteristics and which can be selected by a suitable selection or screening method. The characteristics can be any property or attribute capable of being selected for or detected in a screening system, and may include properties of: an encoded protein, a transcriptional element, a sequence controlling transcription, RNA processing, RNA stability, chromatin conformation, translation, or other expression property of a gene or transgene, a replicative element, a protein-binding element, or the like, such as any feature which confers a selectable or detectable property. In some embodiments, the selected characteristic will be a decreased $K_m$ and/or increased $K_{cat}$ over the wild-type protein as provided herein. In other embodiments, a protein or polynucleotide generated from sequence shuffling will have a ligand binding affinity greater than the non-shuffled wild-type polynucleotide. The increase in such properties can be at least 110%, 120%, 130%, 140% or at least 150% of the wild-type value.

Generic and Consensus Sequences

Polynucleotides and polypeptides of the present invention further include those having: (a) a generic sequence of at least two homologous polynucleotides or polypeptides, respectively, of the present invention; and (b) a consensus sequence of at least three homologous polynucleotides or polypeptides, respectively, of the present invention. The generic sequence of the present invention comprises each species of polypeptide or polynucleotide embraced by the generic polypeptide or polynucleotide sequence, respectively. The individual species encompassed by a polynucleotide having an amino acid or nucleic acid consensus sequence can be used to generate antibodies or produce nucleic acid probes or primers to screen for homologs in other species, genera, families, orders, classes, phyla, or kingdoms. For example, a polynucleotide having a consensus sequence from a gene family of *Zea mays* can be used to generate antibody or nucleic acid probes or primers to other *Gramineae* species such as wheat, rice, or sorghum. Alternatively, a polynucleotide having a consensus sequence generated from orthologous genes can be used to identify or isolate orthologs of other taxa. Typically, a polynucleotide having a consensus sequence will be at least 9, 10, 15, 20, 25, 30 or 40 amino acids in length, or 20, 30, 40, 50, 100 or 150 nucleotides in length. As those of skill in the art are aware, a conservative amino acid substitution can be used for amino acids which differ amongst aligned sequences but are from the same conservative substitution group as discussed above. Optionally, no more than 1 or 2 conservative amino acids are substituted for each 10 amino acid length of consensus sequence.

Similar sequences used for generation of a consensus or generic sequence include any number and combination of allelic variants of the same gene, orthologous, or paralogous sequences as provided herein. Optionally, similar sequences used in generating a consensus or generic sequence are identified using the BLAST program's smallest sum probability (P(N)). Various suppliers of sequence-analysis software are listed in chapter 7 of *Current Protocols in Molecular Biology*, F. M. Ausubel, et al., Eds., Current Protocols, a joint venture between Greene Publishing Associates, Inc. and John Wiley & Sons, Inc. (Supplement 30). A polynucleotide sequence is considered similar to a reference sequence if the smallest sum probability in a comparison of the test nucleic acid to the reference nucleic acid is less than about 0.1, more preferably less than about 0.01, or 0.001, and most preferably less than about 0.0001, or 0.00001. Similar polynucleotides can be aligned and a consensus or generic sequence generated using multiple sequence alignment software available from a number of commercial suppliers such as the Genetics Computer Group's (Madison, Wis.) PILEUP software, Vector NTI's (North Bethesda, Md.) ALIGNX, or Genecode's (Ann Arbor, Mich.) SEQUENCHER. Conveniently, default parameters of such software can be used to generate consensus or generic sequences.

Detection of Nucleic Acids

The present invention further provides methods for detecting a polynucleotide of the present invention in a nucleic acid sample suspected of containing a polynucleotide of the present invention, such as a plant cell lysate, particularly a lysate of maize. In some embodiments, a cognate gene of a polynucleotide of the present invention or portion thereof can be amplified prior to the step of contacting the nucleic acid sample with a polynucleotide of the present invention. The nucleic acid sample is contacted with the polynucleotide to form a hybridization complex. The polynucleotide hybridizes under stringent conditions to a gene encoding a polypeptide of the present invention. Formation of the hybridization complex is used to detect a gene encoding a polypeptide of the present invention in the nucleic acid sample. Those of skill will appreciate that an isolated nucleic acid comprising a polynucleotide of the present invention should lack cross-hybridizing sequences in common with non-target genes that would yield a false positive result. Detection of the hybridization complex can be achieved using any number of well-known methods. For example, the nucleic acid sample, or a portion thereof, may be assayed by hybridization formats including but not limited to, solution phase, solid phase, mixed phase, or in situ hybridization assays.

Detectable labels suitable for use in the present invention include any composition detectable by spectroscopic, radio-isotopic, photochemical, biochemical, immunochemical, electrical, optical or chemical means. Useful labels in the present invention include biotin for staining with labeled streptavidin conjugate, magnetic beads, fluorescent dyes, radiolabels, enzymes, and calorimetric labels. Other labels include ligands which bind to antibodies labeled with fluorophores, chemiluminescent agents, and enzymes. Labeling the nucleic acids of the present invention is readily achieved such as by the use of labeled PCR primers.

In certain embodiments the nucleic acid sequences of the present invention can be used in combination ("stacked") with other polynucleotide sequences of interest in order to create plants with a desired phenotype. The combinations generated can include multiple copies of any one or more of the polynucleotides of interest. The polynucleotides of the present invention may be stacked with any gene or combination of genes to produce plants with a variety of desired trait combinations, including but not limited to traits desirable for animal feed such as high oil genes (e.g., U.S. Pat. No. 6,232, 529); balanced amino acids (e.g., hordothionins (U.S. Pat. Nos. 5,990,389; 5,885,801; 5,885,802 and 5,703,409); barley high lysine (Williamson, et al., (1987) *Eur. J. Biochem.* 165: 99-106; and WO 98/20122); and high methionine proteins (Pedersen, et al., (1986) *J. Biol. Chem.* 261:6279; Kirihara, et al., (1988) *Gene* 71:359 and Musumura, et al., (1989) *Plant Mol. Biol.* 12:123)); increased digestibility (e.g., modified storage proteins (U.S. patent application Ser. No. 10/053,410, filed Nov. 7, 2001); and thioredoxins (U.S. patent application Ser. No. 10/005,429, filed Dec. 3, 2001)), the disclosures of which are herein incorporated by reference. The polynucleotides of the present invention can also be stacked with traits desirable for insect, disease or herbicide resistance (e.g., *Bacillus thuringiensis* toxic proteins (U.S. Pat. Nos. 5,366, 892; 5,747,450; 5,737,514; 5,723,756; 5,593,881; Geiser, et al., (1986) *Gene* 48:109); lectins (Van Damme, et al., (1994) *Plant Mol. Biol.* 24:825); fumonisin detoxification genes (U.S. Pat. No. 5,792,931); avirulence and disease resistance genes (Jones, et al., (1994) *Science* 266:789; Martin, et al., (1993) *Science* 262:1432; Mindrinos, et al., (1994) *Cell* 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE) and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert, et al., (1988) *J. Bacteriol.* 170:5837-5847) facilitate expression of polyhydroxyalkanoates (PHAs)), the disclosures of which are herein incorporated by reference. One could also combine the polynucleotides of the present invention with polynucleotides affecting agronomic traits such as male sterility (e.g., see, U.S. Pat. No. 5,583,210), stalk strength, flowering time, or transformation technology traits such as cell cycle regulation or gene targeting (e.g., WO 99/61619; WO 00/17364; WO 99/25821), the disclosures of which are herein incorporated by reference.

These stacked combinations can be created by any method, including but not limited to cross breeding plants by any conventional or TopCross methodology, or genetic transformation. If the traits are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences of interest can be driven by the same promoter or by different promoters. In certain cases, it may be desirable to introduce a transformation cassette that will suppress the expression of a polynucleotide of interest. This may be accompanied by any combination of other suppression cassettes or overexpression cassettes to generate the desired combination of traits in the plant.

The transformed plants of the invention may be used in a plant breeding program. The goal of plant breeding is to combine, in a single variety or hybrid, various desirable traits. For field crops, these traits may include, for example, resistance to diseases and insects, tolerance to heat and drought, reduced time to crop maturity, greater yield, and better agronomic quality. With mechanical harvesting of many crops, uniformity of plant characteristics such as germination and stand establishment, growth rate, maturity, and plant and ear height, is desirable. Traditional plant breeding is an important tool in developing new and improved commercial crops. This invention encompasses methods for producing a maize plant by crossing a first parent maize plant with a second parent maize plant wherein one or both of the parent maize plants is a transformed plant displaying enhanced vigor, as described herein.

Plant breeding techniques known in the art and used in a maize plant breeding program include, but are not limited to, recurrent selection, bulk selection, mass selection, backcrossing, pedigree breeding, open pollination breeding, restriction fragment length polymorphism enhanced selection, genetic marker enhanced selection, doubled haploids, and transformation. Often combinations of these techniques are used.

The development of maize hybrids in a maize plant breeding program requires, in general, the development of homozygous inbred lines, the crossing of these lines, and the evaluation of the crosses. There are many analytical methods available to evaluate the result of a cross. The oldest and most traditional method of analysis is the observation of phenotypic traits. Alternatively, the genotype of a plant can be examined.

A genetic trait which has been engineered into a particular maize plant using transformation techniques, could be moved into another line using traditional breeding techniques that are well known in the plant breeding arts. For example, a backcrossing approach is commonly used to move a transgene from a transformed maize plant to an elite inbred line, and the resulting progeny would then comprise the transgene(s). Also, if an inbred line was used for the transformation then the transgenic plants could be crossed to a different inbred in order to produce a transgenic hybrid maize plant. As used herein, "crossing" can refer to a simple X by Y cross, or the process of backcrossing, depending on the context.

The development of a maize hybrid in a maize plant breeding program involves three steps: (1) the selection of plants from various germplasm pools for initial breeding crosses; (2) the selfing of the selected plants from the breeding crosses for several generations to produce a series of inbred lines, which, while different from each other, breed true and are highly uniform; and (3) crossing the selected inbred lines with different inbred lines to produce the hybrids. During the inbreeding process in maize, the vigor of the lines decreases. Vigor is restored when two different inbred lines are crossed to produce the hybrid. An important consequence of the homozygosity and homogeneity of the inbred lines is that the hybrid created by crossing a defined pair of inbreds will always be the same. Once the inbreds that give a superior hybrid have been identified, the hybrid seed can be reproduced indefinitely as long as the homogeneity of the inbred parents is maintained.

Transgenic plants of the present invention may be used to produce a single cross hybrid, a three-way hybrid or a double cross hybrid. A single cross hybrid is produced when two inbred lines are crossed to produce the F1 progeny. A double cross hybrid is produced from four inbred lines crossed in pairs (A×B and C×D) and then the two F1 hybrids are crossed again (A×B)×(C×D). A three-way cross hybrid is produced from three inbred lines where two of the inbred lines are crossed (A×B) and then the resulting F1 hybrid is crossed with the third inbred (A×B)×C. Much of the hybrid vigor and uniformity exhibited by F1 hybrids is lost in the next generation (F2). Consequently, seed produced by hybrids is consumed rather than planted.

Although the present invention has been described in some detail by way of illustration and example for purposes of clarity of understanding, it will be obvious that certain changes and modifications may be practiced within the scope of the appended claims.

Example 1

This example describes the construction of a cDNA library.

Total RNA can be isolated from maize tissues with TRIzol Reagent (Life Technology Inc. Gaithersburg, Md.) using a modification of the guanidine isothiocyanate/acid-phenol procedure described by Chomczynski and Sacchi (Chomczynski and Sacchi, (1987) *Anal. Biochem* 162:156). In brief, plant tissue samples are pulverized in liquid nitrogen before the addition of the TRIzol Reagent, and then further homogenized with a mortar and pestle. Addition of chloroform followed by centrifugation is conducted for separation of an aqueous phase and an organic phase. The total RNA is recovered by precipitation with isopropyl alcohol from the aqueous phase.

The selection of poly(A)+ RNA from total RNA can be performed using PolyATact system (Promega Corporation. Madison, Wis.). Biotinylated oligo(dT) primers are used to hybridize to the 3' poly(A) tails on mRNA. The hybrids are captured using streptavidin coupled to paramagnetic particles and a magnetic separation stand. The mRNA is then washed at high stringency conditions and eluted by RNase-free deionized water.

cDNA synthesis and construction of unidirectional cDNA libraries can be accomplished using the SuperScript Plasmid System (Life Technology Inc. Gaithersburg, Md.). The first strand of cDNA is synthesized by priming an oligo(dT) primer containing a Not I site. The reaction is catalyzed by SuperScript Reverse Transcriptase II at 45° C. The second strand of cDNA is labeled with alpha-$^{32}$P-dCTP and a portion of the reaction analyzed by agarose gel electrophoresis to determine cDNA sizes. cDNA molecules smaller than 500 base pairs and unligated adapters are removed by Sephacryl-S400 chromatography. The selected cDNA molecules are ligated into pSPORT1 vector in between of Not I and Sal I sites.

Alternatively, cDNA libraries can be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see, Adams, et al., (1991) *Science* 252:1651-1656). The resulting ESTs are analyzed using a Perkin Elmer Model 377 fluorescent sequencer.

Example 2

This method describes construction of a full-length enriched cDNA library.

An enriched full-length cDNA library can be constructed using one of two variations of the method of Carninci, et al., (1996) *Genomics* 37:327-336. These variations are based on chemical introduction of a biotin group into the diol residue of the 5' cap structure of eukaryotic mRNA to select full-length first strand cDNA. The selection occurs by trapping the biotin residue at the cap sites using streptavidin-coated magnetic beads followed by RNase I treatment to eliminate incompletely synthesized cDNAs. Second strand cDNA is synthesized using established procedures such as those provided in Life Technologies' (Rockville, Md.) "SuperScript Plasmid System for cDNA Synthesis and Plasmid Cloning" kit. Libraries made by this method have been shown to contain 50% to 70% full-length cDNAs.

The first strand synthesis methods are detailed below. An asterisk denotes that the reagent was obtained from Life Technologies, Inc.

A. First Strand cDNA Synthesis Method 1 (with Trehalose)

| | |
|---|---|
| mRNA (10 ug) | 25 µl |
| *Not I primer (5 ug) | 10 µl |
| *5× 1$^{st}$ strand buffer | 43 µl |
| *0.1m DTT | 20 µl |
| *dNTP mix 10 mm | 10 µl |
| BSA 10 ug/µl | 1 µl |
| Trehalose (saturated) | 59.2 µl |
| RNase inhibitor (Promega) | 1.8 µl |
| *Superscript II RT 200 u/µl | 20 µl |
| 100% glycerol | 18 µl |
| Water | 7 µl |

The mRNA and Not I primer are mixed and denatured at 65° C. for 10 min. They are then chilled on ice and other components added to the tube. Incubation is at 45° C. for 2 min. Twenty microliters of RT (reverse transcriptase) is added to the reaction and start program on the thermocycler (MJ Research, Waltham, Mass.):

| | | |
|---|---|---|
| Step 1 | 45° C. | 10 min |
| Step 2 | 45° C. | −0.3° C./cycle, 2 seconds/cycle |
| Step 3 | go to 2 for 33 cycles | |
| Step 4 | 35° C. | 5 min |
| Step 5 | 45° C. | 5 min |
| Step 6 | 45° C. | 0.2° C./cycle, 1 sec/cycle |
| Step 7 | go to 7 for 49 cycles | |
| Step 8 | 55° C. | 0.1° C./cycle, 12 sec/cycle |
| Step 9 | go to 8 for 49 cycles | |
| Step 10 | 55° C. | 2 min |
| Step 11 | 60° C. | 2 min |
| Step 12 | go to 11 for 9 times | |
| Step 13 | 4° C. forever | |
| Step 14 | end | |

B. First Strand cDNA Synthesis Method 2

| | |
|---|---|
| mRNA (10 µg) | 25 µl |
| water | 30 µl |
| *Not I adapter primer (5 µg) | 10 µl |
| 65° C. for 10 min, chill on ice, then add following reagents, | |
| *5× first buffer | 20 µl |
| *0.1M DTT | 10 µl |
| *10 mM dNTP mix | 5 µl |

Incubate at 45° C. for 2 min, then add 10 µl of *Superscript II RT (200 u/µl), start the following program:

| | |
|---|---|
| Step 1 | 45° C. for 6 sec, −0.1° C./cycle |
| Step 2 | go to 1 for 99 additional cycles |
| Step 3 | 35° C. for 5 min |
| Step 4 | 45° C. for 60 min |
| Step 5 | 50° C. for 10 min |
| Step 6 | 4° C. forever |
| Step 7 | end |

After the 1$^{st}$ strand cDNA synthesis, the DNA is extracted by phenol according to standard procedures, and then precipitated in NaOAc and ethanol, and stored in −20° C.

C Oxidization of the Diol Group of mRNA for Biotin Labeling

First strand cDNA is spun down and washed once with 70% EtOH. The pellet is resuspended in 23.2 µl of DEPC treated water and put on ice. Prepare 100 mM of NaIO4 freshly, and then add the following reagents:

| | |
|---|---|
| mRNA:1$^{st}$ cDNA (start with 20 µg mRNA) | 46.4 µl |
| 100 mM NaIO4 (freshly made) | 2.5 µl |
| NaOAc 3M pH 4.5 | 1.1 µl |

To make 100 mM NaIO4, use 21.39 µg of NaIO4 for 1 µl of water.

Wrap the tube in a foil and incubate on ice for 45 min.

After the incubation, the reaction is then precipitated in:

| | |
|---|---|
| 5M NaCl | 10 µl |
| 20% SDS | 0.5 µl |
| isopropanol | 61 µl |

Incubate on ice for at least 30 min, then spin it down at max speed at 4° C. for 30 min and wash once with 70% ethanol and then 80% EtOH.

D. Biotinylation of the mRNA Diol Group

Resuspend the DNA in 110 µl DEPC treated water, then add the following reagents:

| | |
|---|---|
| 20% SDS | 5 µl |
| 2M NaOAc pH 6.1 | 5 µl |
| 10 mm biotin hydrazide (freshly made) | 300 µl |

Wrap in a foil and incubate at room temperature overnight.

E. RNase I Treatment

Precipitate DNA in:

| | |
|---|---|
| 5M NaCl | 10 µl |
| 2M NaOAc pH 6.1 | 75 µl |
| biotinylated mRNA:cDNA | 420 µl |
| 100% EtOH (2.5 Vol) | 1262.5 µl |

(Perform this precipitation in two tubes and split the 420 µl of DNA into 210 µl each, add 5 µl of 5M NaCl, 37.5 µl of 2M NaOAc pH 6.1, and 631.25 µl of 100% EtOH).

Store at −20° C. for at least 30 min. Spin the DNA down at 4° C. at maximal speed for 30 min. and wash with 80% EtOH twice, then dissolve DNA in 70 µl RNase free water. Pool two tubes and end up with 140 µl.

Add the following reagents:

| | |
|---|---|
| RNase One 10 U/µl | 40 µl |
| 1$^{st}$ cDNA:RNA | 140 µl |
| 10X buffer | 20 µl |

Incubate at 37° C. for 15 min.

Add 5 µl of 40 µg/µl yeast tRNA to each sample for capturing.

F. Full Length 1$^{st}$ cDNA Capturing

Blocking the beads with yeast tRNA:

| | |
|---|---|
| Beads | 1 ml |
| Yeast tRNA 40 µg/µl | 5 µl |

Incubate on ice for 30 min with mixing, wash 3 times with 1 ml of 2M NaCl, 50 mmEDTA, pH 8.0.

Resuspend the beads in 800% of 2M NaCl, 50 mm EDTA, pH 8.0, add RNase I treated sample 200 µl, and incubate the reaction for 30 min at room temperature. Capture the beads using the magnetic stand, save the supernatant, and start following washes:

2 washes with 2M NaCl, 50 mm EDTA, pH 8.0, 1 ml each time, 1 wash with 0.4% SDS, 50 µg/ml tRNA, 1 wash with 10 mm Tris-Cl pH 7.5, 0.2 mm EDTA, 10 mm NaCl, 20% glycerol, 1 wash with 50 µg/ml tRNA, 1 wash with 1$^{st}$ cDNA buffer G. Second Strand cDNA Synthesis Resuspend the beads in:

| | |
|---|---|
| *5X first buffer | 8 µl |
| *0.1 mM DTT | 4 µl |
| *10 mm dNTP mix | 8 µl |
| *5X 2nd buffer | 60 µl |
| *E. coli Ligase 10 U/µl | 2 µl |
| *E. coli DNA polymerase 10 U/µl | 8 µl |
| *E. coli RNaseH 2 U/µl | 2 µl |
| P32 dCTP 10 µci/µl | 2 µl |
| Or water up to 300 µl | 208 µl |

Incubate at 16° C. for 2 hr with mixing the reaction in every 30 min.

Add 4 µl of T4 DNA polymerase and incubate for additional 5 min at 16° C.

Elute 2$^{nd}$ cDNA from the beads.

Use a magnetic stand to separate the 2$^{nd}$ cDNA from the beads, then resuspend the beads in 200 µl of water, and then separate again, pool the samples (about 500 µl), Add 200 µl of water to the beads, then 200 µl of phenol: chloroform, vortex, and spin to separate the sample with phenol.

Pool the DNA together (about 700 µl) and use phenol to clean the DNA again, DNA is then precipitated in 2 µg of glycogen and 0.5 vol of 7.5M NH$_4$OAc and 2 vol of 100% EtOH. Precipitate overnight. Spin down the pellet and wash with 70% EtOH, air-dry the pellet.

| | | | |
|---|---|---|---|
| DNA | 250 µl | DNA | 200 µl |
| 7.5M NH4OAc | 125 µl | 7.5M NH4OAc | 100 µl |
| 100% EtOH | 750 µl | 100% EtOH | 600 µl |
| glycogen 1 µg/µl | 2 µl | glycogen 1 µg/µl | 2 µl |

H. Sal I Adapter Ligation

Resuspend the pellet in 26 µl of water and use 1 µl for TAE gel.

Set up reaction as following:

| | |
|---|---|
| 2$^{nd}$ strand cDNA | 25 µl |
| *5X T4 DNA ligase buffer | 10 µl |
| *Sal I adapters | 10 µl |
| *T4 DNA ligase | 5 µl |

Mix gently, incubate the reaction at 16° C. overnight.

Add 2 μl of ligase second day and incubate at room temperature for 2 hrs (optional).

Add 50 μl water to the reaction and use 100 μl of phenol to clean the DNA, 90 μl of the upper phase is transferred into a new tube and precipitate in:

| | |
|---|---|
| Glycogen 1 μg/μl | 2 μl |
| Upper phase DNA | 90 μl |
| 7.5M NH4OAc | 50 μl |
| 100% EtOH | 300 μl | precipitate at −20° C. overnight

Spin down the pellet at 4° C. and wash in 70% EtOH, dry the pellet.

I. Not I Digestion

| | |
|---|---|
| $2^{nd}$ cDNA | 41 μl |
| *Reaction 3 buffer | 5 μl |
| *Not I 15 u/μl | 4 μl |

Mix gently and incubate the reaction at 37° C. for 2 hr.

Add 50 μl of water and 100 μl of phenol, vortex, and take 90 μl of the upper phase to a new tube, then add 50 μl of $NH_{40}Ac$ and 300 μl of EtOH. Precipitate overnight at −20° C.

Cloning, ligation, and transformation are performed per the Superscript cDNA synthesis kit.

Example 3

This example describes cDNA sequencing and library subtraction.

Individual colonies can be picked and DNA prepared either by PCR with M13 forward primers and M13 reverse primers, or by plasmid isolation. cDNA clones can be sequenced using M13 reverse primers.

cDNA libraries are plated out on 22×22 cm² agar plate at density of about 3,000 colonies per plate. The plates are incubated in a 37° C. incubator for 12-24 hours. Colonies are picked into 384-well plates by a robot colony picker, Q-bot (GENETIX Limited). These plates are incubated overnight at 37° C. Once sufficient colonies are picked, they are pinned onto 22×22 cm² nylon membranes using Q-bot. Each membrane holds 9,216 or 36,864 colonies. These membranes are placed onto an agar plate with an appropriate antibiotic. The plates are incubated at 37° C. overnight.

After colonies are recovered on the second day, these filters are placed on filter paper prewetted with denaturing solution for four minutes, then incubated on top of a boiling water bath for an additional four minutes. The filters are then placed on filter paper prewetted with neutralizing solution for four minutes. After excess solution is removed by placing the filters on dry filter papers for one minute, the colony side of the filters is placed into Proteinase K solution, incubated at 37° C. for 40-50 minutes. The filters are placed on dry filter papers to dry overnight. DNA is then cross-linked to nylon membrane by UV light treatment.

Colony hybridization is conducted as described by Sambrook, et al., (in Molecular Cloning: A laboratory Manual, $2^{nd}$ Edition). The following probes can be used in colony hybridization:

1. First strand cDNA from the same tissue as the library was made from to remove the most redundant clones.

2. 48-192 most redundant cDNA clones from the same library based on previous sequencing data.

3. 192 most redundant cDNA clones in the entire maize sequence database.

4. A Sal-A20 oligo nucleotide: TCG ACC CAC GCG TCC GAA AAA AAA AAA AAA AAA AAA, removes clones containing a poly A tail but no cDNA.

5. cDNA clones derived from rRNA.

The image of the autoradiography is scanned into computer and the signal intensity and cold colony addresses of each colony is analyzed. Re-arraying of cold-colonies from 384 well plates to 96 well plates is conducted using Q-bot.

Example 4

This example describes identification of the gene from a computer homology search.

Gene identities can be determined by conducting BLAST (Basic Local Alignment Search Tool; Altschul, et al., (1993) *J. Mol. Biol.* 215:403-410; see, also, www.ncbi.nlm.nih.gov/BLAST/) searches under default parameters for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences are analyzed for similarity to all publicly available DNA sequences contained in the "nr" database using the BLASTN program. The DNA sequences are translated in all reading frames and compared for similarity to all publicly available protein sequences contained in the "nr" database using the BLASTX program (Gish and States, (1993) *Nature Genetics* 3:266-272) provided by the NCBI. In some cases, the sequencing data from two or more clones containing overlapping segments of DNA are used to construct contiguous DNA sequences.

Sequence alignments and percent identity calculations can be performed using the Megalign program of the LASERGENE bioinformatics computing suite (DNASTAR Inc., Madison, Wis.). Multiple alignment of the sequences can be performed using the Clustal method of alignment (Higgins and Sharp (1989) *CABIOS.* 5:151-153) with the default parameters (GAP PENALTY=10, GAP LENGTH PENALTY=10). Default parameters for pairwise alignments using the Clustal method are KTUPLE 1, GAP PENALTY=3, WINDOW=5 and DIAGONALS SAVED=5.

Example 5

This example describes expression of transgenes in monocot cells.

A transgene can be constructed comprising a cDNA encoding the instant polypeptides, such as ipt (SEQ ID NO: 2) or ivr2 (SEQ ID NO: 20), in sense orientation with respect to a maize silk-preferred promoter, such as gl2 (SEQ ID NO: 1 or 26), that is located 5' to the cDNA fragment, and an appropriate termination sequence, such as the 10 kD zein 3' end, located 3' to the cDNA fragment. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (Epicurian Coli XL-1 Blue; Stratagene). Bacterial transformants can be screened by restriction enzyme digestion of plasmid DNA and limited nucleotide sequence analysis using the dideoxy chain termination method (Sequenase DNA Sequencing Kit; U.S. Biochemical). The resulting plasmid construct would comprise a transgene encoding, in the 5' to 3' direction, the maize 27 kD zein promoter, a cDNA fragment encoding the instant polypeptides, and the 10 kD zein 3' region.

The transgene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu, et al., (1975) *Sci. Sin. Peking* 18:659-668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (Hoechst Ag, Frankfurt, Germany) or equivalent may be used in transformation experiments in order to provide for a selectable marker. This plasmid contains the Pat gene (see, European Patent Publication Number 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell, et al., (1985) *Nature* 313:810-812) and the 3' region of the nopaline synthase gene from the T-DNA of the Ti plasmid of *Agrobacterium tumefaciens*.

The particle bombardment method (Klein, et al., (1987) *Nature* 327:70-73) may be used to transfer genes to the callus culture cells. According to this method, gold particles (1 µm in diameter) are coated with DNA using the following technique. Ten µg of plasmid DNAs are added to 50 µL of a suspension of gold particles (60 mg per mL). Calcium chloride (50 µL of a 2.5 M solution) and spermidine free base (20 µL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 µL of absolute ethanol, centrifuged again and the supernatant removed. The ethanol rinse is performed again and the particles resuspended in a final volume of 30 µL of ethanol. An aliquot (5 µL) of the DNA-coated gold particles can be placed in the center of a Kapton flying disc (Bio-Rad Labs). The particles are then accelerated into the corn tissue with a Biolistic PDS-1000/He (Bio-Rad Instruments, Hercules Calif.), using a helium pressure of 1000 psi, a gap distance of 0.5 m and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm, et al., (1990) *Bio/Technology* 8:833-839).

Example 6

This example describes expression of transgenes in dicot cells.

A seed-specific expression cassette composed of the promoter and transcription terminator from the gene encoding the 0 subunit of the seed storage protein phaseolin from the bean *Phaseolus vulgaris* (Doyle, et al., (1986) *J. Biol. Chem.* 261:9228-9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), SmaI, KpnI and XbaI. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3-5 mm in length dissected from surface sterilized, immature seeds of the soybean cultivar A2872, can be cultured in the light or dark at 26° C. on an appropriate agar medium for 6-10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein, et al., (1987) Nature (London) 327:70-73, U.S. Pat. No. 4,945,050). A Du Pont Biolistic PDS1000/HE instrument (helium retrofit) can be used for these transformations.

A selectable marker gene which can be used to facilitate soybean transformation is a transgene composed of the 35S promoter from Cauliflower Mosaic Virus (Odell, et al., (1985) Nature 313:810-812), the hygromycin phosphotransferase gene from plasmid pJR225 (from E. coli; Gritz, et al., (1983) Gene 25:179-188) and the 3' region of the nopaline synthase gene from the T-DNA of the Ti plasmid of Agrobacterium tumefaciens. The seed expression cassette comprising the phaseolin 5' region, the fragment encoding the instant polypeptide and the phaseolin 3' region can be isolated as a restriction fragment. This fragment can then be inserted into a unique restriction site of the vector carrying the marker gene.

To 50 µL of a 60 mg/mL 1 µm gold particle suspension are added (in order): 5 µL DNA (1 µg/µL), 20 µl spermidine (0.1 M), and 50 µL CaCl$_2$ (2.5 M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five microliters of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 7

This example describes expression of a transgene in microbial cells.

The cDNAs encoding the instant polypeptides can be inserted into the T7 E. coli expression vector pBT430. This vector is a derivative of pET-3a (Rosenberg, et al., (1987) Gene 56:125-135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG low melting agarose gel (FMC). Buffer and agarose contain 10 µg/ml ethidium bromide for visualization of the DNA fragment. The fragment can then be purified from the agarose gel by digestion with GELase (Epicentre Technologies) according to the manufacturer's instructions, ethanol precipitated, dried and resuspended in 20 µL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 µg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into E. coli strain BL21(DE3) (Studier, et al., (1986) J. Mol. Biol. 189:113-130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 hours at 25° C. Cells are then harvested by centrifugation and re-suspended in 50 µL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One microgram of protein from the soluble fraction of the culture can be separated by SDS-polyacrylamide gel electrophoresis. Gels can be observed for protein bands migrating at the expected molecular weight.

The above examples are provided to illustrate the invention but not to limit its scope. Other variants of the invention will be readily apparent to one of ordinary skill in the art and are encompassed by the appended claims. All publications, patents, patent applications, and computer programs cited herein are hereby incorporated by reference.

What is claimed is:

1. A method for enhancing silk exsertion in a *Zea mays* plant under stress, relative to a non-transformed *Zea mays* plant under stress, comprising transforming said plant or its ancestor with a construct comprising a silk-specific or silk-preferred promoter of SEQ ID NO: 1 or SEQ ID NO: 26 operably linked to a polynucleotide encoding a polypeptide which increases cell division.

2. The method of claim 1 wherein the polynucleotide encodes cyclin D.

3. The method of claim 2 wherein the polynucleotide encoding cyclin D comprises SEQ ID: 4.

4. The method of claim 1 wherein the polynucleotide encodes a cyclin-dependent kinase.

5. The method of claim 4 wherein the polynucleotide encoding a cyclin-dependent kinase comprises SEQ ID NO: 6.

* * * * *

SEQUENCE LISTING

<160> NUMBER OF SEQ ID NOS: 26

<210> SEQ ID NO 1
<211> LENGTH: 1946
<212> TYPE: DNA
<213> ORGANISM: Zea mays

<400> SEQUENCE: 1

```
acctggtcag ttgtatattc ccctcttttt tattagtgaa taaagatatc caaaaaactt      60
gaaatgcact acctctattt tattatttgg tttttatgat gaaaactttt tttttacttt     120
tctggtttta ttgtgactgt agtataagac agcatgggct ctctcaaata ttgtctctgc     180
ggatgacgct attgtcagtt ataaatattg gcggcatatt aggaaacaaa ttatccctat     240
ttgagttgcg cacacatatc atgttattat tgtgaatttg tgagatattg aggttgatga     300
tatatatgtt gttcattttc atgtgatcgt tatgcactaa cagttatcga ataatttata     360
cgcgtcgcaa cgcacgggca catacatagt tacaatttaa gtggccagat tacactttct     420
tcttcggggt gattttaac taaacatcta acaatgcgtg gagacgatgt tgctcatgct      480
gaaatagtac taccagcttc tgtcgtagca atctgtgatg agacacctcc agccctccag     540
tcaccacttc ttcagtcctt gtaataggaa ccacttcatc agtatgctct tgtattagga     600
accacttcat cagtatgtta ctgtcatata gctcgaagct ctttaggaac cacttcatca     660
gtagttaccc gtgaactatc tcgtgtacat gcaacctata gagcataatg gaattaaata     720
gttgtgacct caccacataa gaatctaact aggtatatgc tcatgtgttg ctatgataaa     780
atacattaat atacaaaaaa tattgtgttt tataatatta actccgtagc aacgcacgag     840
catatacata taacacacac acatgtacat aagttatcgt gttattatac ggtttcgttg     900
caacgcacgg gcacttacct agtatagtat gagggaagca cattcgtgtg ttgcagaatg     960
cagactacca gctgtccagc cctccctcat tcaagacgtg tggggtttgc tcctccgatc    1020
gagtggcacg cacccgtttt ttcaggccta attatggtgc agtgcagtgc agccgctctc    1080
ctgcctgtcc tccccgtggt tcgttccctc gccggaccac cgtggggccg gtagccgctg    1140
cctgcttgct actagatccg atccagcctc gcatcgcatg cccatgccgc catgcggatg    1200
gataataact gtacagtgcc tctttgatag ggtctggcgg ccaggaacta gcgacccgac    1260
caatcgttta tgctcttgca ctgtccgtct acaccgtgtc ccgatcgatt ccactgcctg    1320
tgcgtacgag tagggctggg ccagtaggga tctttctcgc caatcagccc gcatatatgg    1380
acccagtcag taattggctc gcaagtcaca acagatctcg atcggtctgt tgtaccaatc    1440
tacgtactag caacatgtac acgcacgtac cgaagcgggc gtaaaacgtt gtcacgatac    1500
aaactttcgg cggcaagagc atgcggcgcg ctgagcgcag cgcagcgcag tcgtccggtc    1560
gtcccatcgc ggccgttttc ggcgtacgta cggcggtacg ggctacggag cactgactga    1620
ctcgtcggcc gtccaactgt gtagtccgcc gataccgcct gggccaatag cggaatagcc    1680
caaggcgcga cacggcggcg tcacacatcg gcgcagttgg ttgggtcgag ctcccaacca    1740
actcgctccc gcgccagcca agccagccac gacccacgag ccaccaccat tacccgcccg    1800
cccgccacag gccacatcgt ttccggccct gctcggctat atatccgcga gcatctgcat    1860
atcgccatat ccccgccccg ggcaccgcga gctagctagc tactgacacc cggcgccggc    1920
gccgagtaca atacaaggaa agcacc                                         1946
```

<210> SEQ ID NO 2

<211> LENGTH: 723
<212> TYPE: DNA
<213> ORGANISM: Zea mays
<220> FEATURE:
<221> NAME/KEY: CDS
<222> LOCATION: (1)...(720)

<400> SEQUENCE: 2

```
atg gat cta cgt cta att ttc ggt cca act tgc aca gga aag aca tcg    48
Met Asp Leu Arg Leu Ile Phe Gly Pro Thr Cys Thr Gly Lys Thr Ser
 1               5                  10                  15 act gcg ata gct ctt gcc cag cag act ggc ctc cca gtc ctc tcg ctc    96
Thr Ala Ile Ala Leu Ala Gln Gln Thr Gly Leu Pro Val Leu Ser Leu
            20                  25                  30 gat cgc gtc caa tgc tgt cct caa cta tca acc gga agc ggg cga cca   144
Asp Arg Val Gln Cys Cys Pro Gln Leu Ser Thr Gly Ser Gly Arg Pro
        35                  40                  45 aca gtg gaa gaa ctg aaa gga acg act cgt ctg tac ctt gat gat cgc   192
Thr Val Glu Glu Leu Lys Gly Thr Thr Arg Leu Tyr Leu Asp Asp Arg
    50                  55                  60 cct ttg gta aag ggt atc att aca gcc aag caa gct cat gaa cgg ctc   240
Pro Leu Val Lys Gly Ile Ile Thr Ala Lys Gln Ala His Glu Arg Leu
65                  70                  75                  80 att gcg gag gtg cac aat cac gag gcc aaa ggc ggg ctt att ctt gag   288
Ile Ala Glu Val His Asn His Glu Ala Lys Gly Gly Leu Ile Leu Glu
                85                  90                  95 gga gga tct atc tcg ttg ctc agg tgc atg gcg caa agt cgt tat tgg   336
Gly Gly Ser Ile Ser Leu Leu Arg Cys Met Ala Gln Ser Arg Tyr Trp
            100                 105                 110 aac gcg gat ttt cgt tgg cat att att cgc aac gag tta gca gac gag   384
Asn Ala Asp Phe Arg Trp His Ile Ile Arg Asn Glu Leu Ala Asp Glu
        115                 120                 125 gag agc ttc atg agc gtg gcc aag acc aga gtt aag cag atg tta cgc   432
Glu Ser Phe Met Ser Val Ala Lys Thr Arg Val Lys Gln Met Leu Arg
    130                 135                 140 ccc tct gca ggt ctt tct att atc caa gag ttg gtt caa ctt tgg agg   480
Pro Ser Ala Gly Leu Ser Ile Ile Gln Glu Leu Val Gln Leu Trp Arg
145                 150                 155                 160 gag cct cgg ctg agg ccc ata ctg gaa ggg atc gat gga tat cga tat   528
Glu Pro Arg Leu Arg Pro Ile Leu Glu Gly Ile Asp Gly Tyr Arg Tyr
                165                 170                 175 gcc ctg cta ttt gct acc cag aac cag atc acg ccc gat atg cta ttg   576
Ala Leu Leu Phe Ala Thr Gln Asn Gln Ile Thr Pro Asp Met Leu Leu
            180                 185                 190 cag ctc gac gca gat atg gag aat aaa ttg att cac ggt atc gct cag   624
Gln Leu Asp Ala Asp Met Glu Asn Lys Leu Ile His Gly Ile Ala Gln
        195                 200                 205 gag ttt cta atc cat gcg cgt cga cag gaa cag aaa ttc cct ttg gtg   672
Glu Phe Leu Ile His Ala Arg Arg Gln Glu Gln Lys Phe Pro Leu Val
    210                 215                 220 ggc gcg aca gct gtc gaa gcg ttt gaa gga cca cca ttt cga atg tga   720
Gly Ala Thr Ala Val Glu Ala Phe Glu Gly Pro Pro Phe Arg Met *
225                 230                 235 gtt                                                                723
```

<210> SEQ ID NO 3
<211> LENGTH: 239
<212> TYPE: PRT
<213> ORGANISM: Zea mays

<400> SEQUENCE: 3

Met Asp Leu Arg Leu Ile Phe Gly Pro Thr Cys Thr Gly Lys Thr Ser

```
                 1               5                  10                 15
        Thr Ala Ile Ala Leu Ala Gln Gln Thr Gly Leu Pro Val Leu Ser Leu
                         20                  25                  30

Asp Arg Val Gln Cys Cys Pro Gln Leu Ser Thr Gly Ser Gly Arg Pro
                         35                  40                  45

Thr Val Glu Glu Leu Lys Gly Thr Thr Arg Leu Tyr Leu Asp Asp Arg
                50                  55                  60

Pro Leu Val Lys Gly Ile Ile Thr Ala Lys Gln Ala His Glu Arg Leu
         65                  70                  75                  80

Ile Ala Glu Val His Asn His Glu Ala Lys Gly Gly Leu Ile Leu Glu
                             85                  90                  95

Gly Gly Ser Ile Ser Leu Leu Arg Cys Met Ala Gln Ser Arg Tyr Trp
                        100                 105                 110

Asn Ala Asp Phe Arg Trp His Ile Ile Arg Asn Glu Leu Ala Asp Glu
                        115                 120                 125

Glu Ser Phe Met Ser Val Ala Lys Thr Arg Val Lys Gln Met Leu Arg
                    130                 135                 140

Pro Ser Ala Gly Leu Ser Ile Ile Gln Glu Leu Val Gln Leu Trp Arg
        145                 150                 155                 160

Glu Pro Arg Leu Arg Pro Ile Leu Glu Gly Ile Asp Gly Tyr Arg Tyr
                        165                 170                 175

Ala Leu Leu Phe Ala Thr Gln Asn Gln Ile Thr Pro Asp Met Leu Leu
                        180                 185                 190

Gln Leu Asp Ala Asp Met Glu Asn Lys Leu Ile His Gly Ile Ala Gln
                        195                 200                 205

Glu Phe Leu Ile His Ala Arg Arg Gln Glu Gln Lys Phe Pro Leu Val
                    210                 215                 220

Gly Ala Thr Ala Val Glu Ala Phe Glu Gly Pro Pro Phe Arg Met
        225                 230                 235

<210> SEQ ID NO 4
<211> LENGTH: 1077
<212> TYPE: DNA
<213> ORGANISM: Zea mays
<220> FEATURE:
<221> NAME/KEY: CDS
<222> LOCATION: (1)...(1077)

<400> SEQUENCE: 4 atg gtg ccg ggc tat gac tgc gcc gcc tcc gtg ctg ctg tgc gcg gag      48
Met Val Pro Gly Tyr Asp Cys Ala Ala Ser Val Leu Leu Cys Ala Glu
 1               5                  10                  15 gac aac gct gct att ctc ggc ctg gac gac gat ggg gag gag tcc tcc      96
Asp Asn Ala Ala Ile Leu Gly Leu Asp Asp Asp Gly Glu Glu Ser Ser
                 20                  25                  30 tgg gcg gcc gcc gct acg ccg cca cgt gac acc gtc gcc gcc gcc gcc     144
Trp Ala Ala Ala Ala Thr Pro Pro Arg Asp Thr Val Ala Ala Ala Ala
             35                  40                  45 gcc acc ggg gtc gcc gtc gat ggg att ttg acg gag ttc ccc ttg ctc     192
Ala Thr Gly Val Ala Val Asp Gly Ile Leu Thr Glu Phe Pro Leu Leu
         50                  55                  60 tcg gat gac tgc gtt gcg acg ctc gtg gag aag gag gtg gag cac atg     240
Ser Asp Asp Cys Val Ala Thr Leu Val Glu Lys Glu Val Glu His Met
 65                  70                  75                  80 ccc gcg gag ggg tac ctc cag aag ctg cag cga cgg cat ggg gac ctg     288
Pro Ala Glu Gly Tyr Leu Gln Lys Leu Gln Arg Arg His Gly Asp Leu
                 85                  90                  95 gat ttg gcc gcc gtc agg aag gac gcc atc gat tgg att tgg aag gtc     336
```

```
Asp Leu Ala Ala Val Arg Lys Asp Ala Ile Asp Trp Ile Trp Lys Val
            100                 105                 110 att gag cat tac aat ttc gca ccg ttg act gcc gtt ttg tct gtg aac      384
Ile Glu His Tyr Asn Phe Ala Pro Leu Thr Ala Val Leu Ser Val Asn
        115                 120                 125 tac ctc gat aga ttc ctc tcc acg tat gag ttc cct gaa ggc aga gct      432
Tyr Leu Asp Arg Phe Leu Ser Thr Tyr Glu Phe Pro Glu Gly Arg Ala
    130                 135                 140 tgg atg act cag ctc ttg gca gtg gct tgc ttg tct ttg gct tcg aaa      480
Trp Met Thr Gln Leu Leu Ala Val Ala Cys Leu Ser Leu Ala Ser Lys
145                 150                 155                 160 atc gaa gag act ttt gtg cca ctc ccc ttg gat ttg cag gta gcg gag      528
Ile Glu Glu Thr Phe Val Pro Leu Pro Leu Asp Leu Gln Val Ala Glu
                165                 170                 175 gca aag ttt gtt ttt gag gga agg acc ata aaa agg atg gag ctt ctg      576
Ala Lys Phe Val Phe Glu Gly Arg Thr Ile Lys Arg Met Glu Leu Leu
            180                 185                 190 gtg cta agc acc tta aag tgg agg atg cat gct gtt act gct tgc tca      624
Val Leu Ser Thr Leu Lys Trp Arg Met His Ala Val Thr Ala Cys Ser
        195                 200                 205 ttt gtt gaa tac ttt ctt cat aaa ttg agt gat cat ggt gca ccc tcc      672
Phe Val Glu Tyr Phe Leu His Lys Leu Ser Asp His Gly Ala Pro Ser
    210                 215                 220 ttg ctt gca cgc tct cgc tct ttg gac ctt gtc ttg agc acc gct aaa      720
Leu Leu Ala Arg Ser Arg Ser Leu Asp Leu Val Leu Ser Thr Ala Lys
225                 230                 235                 240 ggt gct gaa ttc gtg gta ttc aga ccc tcc gag att gct gcc agt gtt      768
Gly Ala Glu Phe Val Val Phe Arg Pro Ser Glu Ile Ala Ala Ser Val
                245                 250                 255 gca ctt gct gct atc ggc gaa tgc agg agt tct gta att gag aga gct      816
Ala Leu Ala Ala Ile Gly Glu Cys Arg Ser Ser Val Ile Glu Arg Ala
            260                 265                 270 gct agt agc tgc aaa tat ttg gac aag gag agg gtt tta aga tgc cat      864
Ala Ser Ser Cys Lys Tyr Leu Asp Lys Glu Arg Val Leu Arg Cys His
        275                 280                 285 gaa atg att caa gag aag att act gcg gga agc att gtc cta aag tct      912
Glu Met Ile Gln Glu Lys Ile Thr Ala Gly Ser Ile Val Leu Lys Ser
    290                 295                 300 gct gga tca tca atc tcc tct gtg cca caa agc cca ata ggt gtc ctg      960
Ala Gly Ser Ser Ile Ser Ser Val Pro Gln Ser Pro Ile Gly Val Leu
305                 310                 315                 320 gac gct gca gcc tgt ctg agt caa caa agc gat gac gct act gtc ggg     1008
Asp Ala Ala Ala Cys Leu Ser Gln Gln Ser Asp Asp Ala Thr Val Gly
                325                 330                 335 tct cct gca gta tgt tac cat agt tct tcc aca agc aag agg aga agg     1056
Ser Pro Ala Val Cys Tyr His Ser Ser Ser Thr Ser Lys Arg Arg Arg
            340                 345                 350 atc act aga cgt cta ctc taa                                         1077
Ile Thr Arg Arg Leu Leu *
        355

<210> SEQ ID NO 5
<211> LENGTH: 358
<212> TYPE: PRT
<213> ORGANISM: Zea mays

<400> SEQUENCE: 5

Met Val Pro Gly Tyr Asp Cys Ala Ala Ser Val Leu Leu Cys Ala Glu
1               5                   10                  15

Asp Asn Ala Ala Ile Leu Gly Leu Asp Asp Gly Glu Glu Ser Ser
            20                  25                  30
```

| | | | | | | | | | | | |
|---|---|---|---|---|---|---|---|---|---|---|---|
|Trp|Ala|Ala|Ala|Ala|Thr|Pro|Pro|Arg|Asp|Thr|Val|Ala|Ala|Ala|
| |35| | | | |40| | | |45| | | | |

Trp Ala Ala Ala Ala Thr Pro Pro Arg Asp Thr Val Ala Ala Ala
 35                  40                  45

Ala Thr Gly Val Ala Val Asp Gly Ile Leu Thr Glu Phe Pro Leu Leu
 50                  55                  60

Ser Asp Asp Cys Val Ala Thr Leu Val Glu Lys Glu Val Glu His Met
65                  70                  75                  80

Pro Ala Glu Gly Tyr Leu Gln Lys Leu Gln Arg Arg His Gly Asp Leu
                 85                  90                  95

Asp Leu Ala Ala Val Arg Lys Asp Ala Ile Asp Trp Ile Trp Lys Val
            100                 105                 110

Ile Glu His Tyr Asn Phe Ala Pro Leu Thr Ala Val Leu Ser Val Asn
        115                 120                 125

Tyr Leu Asp Arg Phe Leu Ser Thr Tyr Glu Phe Pro Glu Gly Arg Ala
    130                 135                 140

Trp Met Thr Gln Leu Leu Ala Val Ala Cys Leu Ser Leu Ala Ser Lys
145                 150                 155                 160

Ile Glu Glu Thr Phe Val Pro Leu Pro Leu Asp Leu Gln Val Ala Glu
                165                 170                 175

Ala Lys Phe Val Phe Glu Gly Arg Thr Ile Lys Arg Met Glu Leu Leu
            180                 185                 190

Val Leu Ser Thr Leu Lys Trp Arg Met His Ala Val Thr Ala Cys Ser
        195                 200                 205

Phe Val Glu Tyr Phe Leu His Lys Leu Ser Asp His Gly Ala Pro Ser
    210                 215                 220

Leu Leu Ala Arg Ser Arg Ser Leu Asp Leu Val Leu Ser Thr Ala Lys
225                 230                 235                 240

Gly Ala Glu Phe Val Val Phe Arg Pro Ser Glu Ile Ala Ala Ser Val
                245                 250                 255

Ala Leu Ala Ala Ile Gly Glu Cys Arg Ser Ser Val Ile Glu Arg Ala
            260                 265                 270

Ala Ser Ser Cys Lys Tyr Leu Asp Lys Glu Arg Val Leu Arg Cys His
        275                 280                 285

Glu Met Ile Gln Glu Lys Ile Thr Ala Gly Ser Ile Val Leu Lys Ser
290                 295                 300

Ala Gly Ser Ser Ile Ser Ser Val Pro Gln Ser Pro Ile Gly Val Leu
305                 310                 315                 320

Asp Ala Ala Ala Cys Leu Ser Gln Gln Ser Asp Asp Ala Thr Val Gly
                325                 330                 335

Ser Pro Ala Val Cys Tyr His Ser Ser Ser Thr Ser Lys Arg Arg Arg
            340                 345                 350

Ile Thr Arg Arg Leu Leu
        355

```
<210> SEQ ID NO 6
<211> LENGTH: 876
<212> TYPE: DNA
<213> ORGANISM: Zea mays
<220> FEATURE:
<221> NAME/KEY: CDS
<222> LOCATION: (1)...(876)

<400> SEQUENCE: 6 atg gac cag tac gag aag gtg gag aag atc ggg gag ggc acg tac ggg      48
Met Asp Gln Tyr Glu Lys Val Glu Lys Ile Gly Glu Gly Thr Tyr Gly
 1               5                  10                  15 gtg gtg tac aag ggc aag gac cgc cac acc aac gag acg atc gcg ctc      96
```

```
                Val Val Tyr Lys Gly Lys Asp Arg His Thr Asn Glu Thr Ile Ala Leu
                        20                  25                  30 aag aag atc cgc ctc gag cag gag gac gag ggc gtc ccc tcc acc gcc        144
Lys Lys Ile Arg Leu Glu Gln Glu Asp Glu Gly Val Pro Ser Thr Ala
            35                  40                  45 atc cgc gag atc tcc ctc ctc aag gag atg cag cac cgc aac atc gtc        192
Ile Arg Glu Ile Ser Leu Leu Lys Glu Met Gln His Arg Asn Ile Val
        50                  55                  60 agg ctg cag gaa gtc gtg cac aac gac aag tgc atc tac ctc gtc ttc        240
Arg Leu Gln Glu Val Val His Asn Asp Lys Cys Ile Tyr Leu Val Phe
 65              70                  75                  80 gag tac ctc gac ctc gac ctc aag aag cac atg gac tcc tcc acg gac        288
Glu Tyr Leu Asp Leu Asp Leu Lys Lys His Met Asp Ser Ser Thr Asp
                85                  90                  95 ttc aag aac cac cgc ata gtc aaa tcc ttc ctc tac cag att ctg cgg        336
Phe Lys Asn His Arg Ile Val Lys Ser Phe Leu Tyr Gln Ile Leu Arg
            100                 105                 110 ggc atc gcc tac tgc cac tcg cac cgc gtg ctc cac cgc gac ctg aag        384
Gly Ile Ala Tyr Cys His Ser His Arg Val Leu His Arg Asp Leu Lys
        115                 120                 125 ccg cag aac ctg ctg att gac cgc cgc aac aac ctc ttg aag ctc gcg        432
Pro Gln Asn Leu Leu Ile Asp Arg Arg Asn Asn Leu Leu Lys Leu Ala
130                 135                 140 gac ttt gga ctg gcg agg gcg ttc ggc atc cct gtc cgg acg ttc act        480
Asp Phe Gly Leu Ala Arg Ala Phe Gly Ile Pro Val Arg Thr Phe Thr
145                 150                 155                 160 cat gag gtg gtg acg ctt tgg tat aga gcg cct gaa atc ctt ctc ggt        528
His Glu Val Val Thr Leu Trp Tyr Arg Ala Pro Glu Ile Leu Leu Gly
                165                 170                 175 gca agg cat tat tcc acc cct gtt gat gtg tgg tca gtt ggt tgc att        576
Ala Arg His Tyr Ser Thr Pro Val Asp Val Trp Ser Val Gly Cys Ile
            180                 185                 190 ttc gct gaa atg gtg aac cag aag gcg ctt ttt cct ggc gac tct gag        624
Phe Ala Glu Met Val Asn Gln Lys Ala Leu Phe Pro Gly Asp Ser Glu
        195                 200                 205 atc gat gag ctg ttt aag att ttc aga att ttg ggc act cca act aaa        672
Ile Asp Glu Leu Phe Lys Ile Phe Arg Ile Leu Gly Thr Pro Thr Lys
210                 215                 220 gaa aca tgg cca ggc gtt gct tcg ttg cct gat tac aag tca act ttc        720
Glu Thr Trp Pro Gly Val Ala Ser Leu Pro Asp Tyr Lys Ser Thr Phe
225                 230                 235                 240 cca aag tgg cca cct gtg gat ctt gca acg gtg gtc ccg aca ctc gaa        768
Pro Lys Trp Pro Pro Val Asp Leu Ala Thr Val Val Pro Thr Leu Glu
                245                 250                 255 ccg tcg gga atc gat ctc cta tct aag atg ctg cgt cta gat ccc agc        816
Pro Ser Gly Ile Asp Leu Leu Ser Lys Met Leu Arg Leu Asp Pro Ser
            260                 265                 270 aag agg atc acc gcc cgc gcc gcc ctc gag cac gac tac ttc agg gac        864
Lys Arg Ile Thr Ala Arg Ala Ala Leu Glu His Asp Tyr Phe Arg Asp
        275                 280                 285 ctc gag cac gcc                                                        876
Leu Glu His Ala
    290

<210> SEQ ID NO 7
<211> LENGTH: 292
<212> TYPE: PRT
<213> ORGANISM: Zea mays

<400> SEQUENCE: 7

Met Asp Gln Tyr Glu Lys Val Glu Lys Ile Gly Glu Gly Thr Tyr Gly
```

```
                1               5                   10                  15
            Val Val Tyr Lys Gly Lys Asp Arg His Thr Asn Glu Thr Ile Ala Leu
                            20                  25                  30

Lys Lys Ile Arg Leu Glu Gln Glu Asp Glu Gly Val Pro Ser Thr Ala
                        35                  40                  45

Ile Arg Glu Ile Ser Leu Leu Lys Glu Met Gln His Arg Asn Ile Val
                    50                  55                  60

Arg Leu Gln Glu Val Val His Asn Asp Lys Cys Ile Tyr Leu Val Phe
            65                  70                  75                  80

Glu Tyr Leu Asp Leu Asp Leu Lys Lys His Met Asp Ser Ser Thr Asp
                            85                  90                  95

Phe Lys Asn His Arg Ile Val Lys Ser Phe Leu Tyr Gln Ile Leu Arg
                        100                 105                 110

Gly Ile Ala Tyr Cys His Ser His Arg Val Leu His Arg Asp Leu Lys
                    115                 120                 125

Pro Gln Asn Leu Leu Ile Asp Arg Arg Asn Asn Leu Leu Lys Leu Ala
                130                 135                 140

Asp Phe Gly Leu Ala Arg Ala Phe Gly Ile Pro Val Arg Thr Phe Thr
            145                 150                 155                 160

His Glu Val Val Thr Leu Trp Tyr Arg Ala Pro Glu Ile Leu Leu Gly
                            165                 170                 175

Ala Arg His Tyr Ser Thr Pro Val Asp Val Trp Ser Val Gly Cys Ile
                        180                 185                 190

Phe Ala Glu Met Val Asn Gln Lys Ala Leu Phe Pro Gly Asp Ser Glu
                    195                 200                 205

Ile Asp Glu Leu Phe Lys Ile Phe Arg Ile Leu Gly Thr Pro Thr Lys
                210                 215                 220

Glu Thr Trp Pro Gly Val Ala Ser Leu Pro Asp Tyr Lys Ser Thr Phe
            225                 230                 235                 240

Pro Lys Trp Pro Pro Val Asp Leu Ala Thr Val Val Pro Thr Leu Glu
                            245                 250                 255

Pro Ser Gly Ile Asp Leu Leu Ser Lys Met Leu Arg Leu Asp Pro Ser
                        260                 265                 270

Lys Arg Ile Thr Ala Arg Ala Ala Leu Glu His Asp Tyr Phe Arg Asp
                    275                 280                 285

Leu Glu His Ala
                290

<210> SEQ ID NO 8
<211> LENGTH: 759
<212> TYPE: DNA
<213> ORGANISM: Zea mays
<220> FEATURE:
<221> NAME/KEY: CDS
<222> LOCATION: (1)...(759)

<400> SEQUENCE: 8 atg gcg gca gct gct agt gcc ctg ctc ctc ctg ctc tgc tca gcc ttc      48
Met Ala Ala Ala Ala Ser Ala Leu Leu Leu Leu Leu Cys Ser Ala Phe
 1               5                  10                  15 tgc tcc ctt gcc cac cgg gcg gcc ggc gtc gac tac ggc tcg tgg cag      96
Cys Ser Leu Ala His Arg Ala Ala Gly Val Asp Tyr Gly Ser Trp Gln
                20                  25                  30 agc gcc cac gcc acg ttc tac ggc ggc ggc gac gcg tct ggc acg atg     144
Ser Ala His Ala Thr Phe Tyr Gly Gly Gly Asp Ala Ser Gly Thr Met
            35                  40                  45 ggc ggc gcg tgc ggc tac ggg aac atg tac agc acg ggg tac ggc acc     192
```

```
               Gly Gly Ala Cys Gly Tyr Gly Asn Met Tyr Ser Thr Gly Tyr Gly Thr
                50                  55                  60 aac acg gcg gcg ctg agc acg gcg ctg ttc aac gac ggc gcc gcg tgc            240
Asn Thr Ala Ala Leu Ser Thr Ala Leu Phe Asn Asp Gly Ala Ala Cys
 65                  70                  75                  80 ggg tcc tgc tac gag ctg cgc tgc gac aac aac ggg cag tcg tgc ctg            288
Gly Ser Cys Tyr Glu Leu Arg Cys Asp Asn Asn Gly Gln Ser Cys Leu
                 85                  90                  95 ccg ggc acc atc acc gtc acg gcc acc aac ttc tgc ccg ccc aac tac            336
Pro Gly Thr Ile Thr Val Thr Ala Thr Asn Phe Cys Pro Pro Asn Tyr
            100                 105                 110 ggc ctc ccc agc gac gac ggc tgg tgc aac ccg ccg cgc ccg cac                384
Gly Leu Pro Ser Asp Asp Gly Trp Cys Asn Pro Pro Arg Pro His
            115                 120                 125 ttc gac atg gcc cag ccg gcc ttc ctc cag atc gcg cag tac cgc gcc            432
Phe Asp Met Ala Gln Pro Ala Phe Leu Gln Ile Ala Gln Tyr Arg Ala
    130                 135                 140 ggc atc gtg ccc gtc gcc tac agg agg gtg ccg tgc gtg aag aag ggc            480
Gly Ile Val Pro Val Ala Tyr Arg Arg Val Pro Cys Val Lys Lys Gly
145                 150                 155                 160 ggg atc agg ttc acc atc aac ggc cac tcc tac ttc aac ctg gtg ctg            528
Gly Ile Arg Phe Thr Ile Asn Gly His Ser Tyr Phe Asn Leu Val Leu
                165                 170                 175 gtg acc aac gtg gcc ggc gcc ggg gac gtg cag tcc gtg tcc atc aag            576
Val Thr Asn Val Ala Gly Ala Gly Asp Val Gln Ser Val Ser Ile Lys
            180                 185                 190 ggc tcc agc acc ggg tgg cag ccc atg tcc cgc aac tgg ggc cag aac            624
Gly Ser Ser Thr Gly Trp Gln Pro Met Ser Arg Asn Trp Gly Gln Asn
        195                 200                 205 tgg cag agc aac tcg ctc ctc gac ggc cag agc ctg tcc ttc cag gtc            672
Trp Gln Ser Asn Ser Leu Leu Asp Gly Gln Ser Leu Ser Phe Gln Val
    210                 215                 220 acc gcc agc gac ggc cgc acc gtc acc agc aac ggc gtc gct ccg gcg            720
Thr Ala Ser Asp Gly Arg Thr Val Thr Ser Asn Gly Val Ala Pro Ala
225                 230                 235                 240 ggc tgg cag ttc ggc cag acc ttc gag ggc gcc cag ttc                        759
Gly Trp Gln Phe Gly Gln Thr Phe Glu Gly Ala Gln Phe
                245                 250

<210> SEQ ID NO 9
<211> LENGTH: 253
<212> TYPE: PRT
<213> ORGANISM: Zea mays

<400> SEQUENCE: 9

Met Ala Ala Ala Ala Ser Ala Leu Leu Leu Leu Leu Cys Ser Ala Phe
  1               5                  10                  15

Cys Ser Leu Ala His Arg Ala Ala Gly Val Asp Tyr Gly Ser Trp Gln
             20                  25                  30

Ser Ala His Ala Thr Phe Tyr Gly Gly Gly Asp Ala Ser Gly Thr Met
         35                  40                  45

Gly Gly Ala Cys Gly Tyr Gly Asn Met Tyr Ser Thr Gly Tyr Gly Thr
     50                  55                  60

Asn Thr Ala Ala Leu Ser Thr Ala Leu Phe Asn Asp Gly Ala Ala Cys
 65                  70                  75                  80

Gly Ser Cys Tyr Glu Leu Arg Cys Asp Asn Asn Gly Gln Ser Cys Leu
                 85                  90                  95

Pro Gly Thr Ile Thr Val Thr Ala Thr Asn Phe Cys Pro Pro Asn Tyr
            100                 105                 110
```

```
Gly Leu Pro Ser Asp Asp Gly Gly Trp Cys Asn Pro Pro Arg Pro His
            115                 120                 125
Phe Asp Met Ala Gln Pro Ala Phe Leu Gln Ile Ala Gln Tyr Arg Ala
130                 135                 140
Gly Ile Val Pro Val Ala Tyr Arg Arg Val Pro Cys Val Lys Lys Gly
145                 150                 155                 160
Gly Ile Arg Phe Thr Ile Asn Gly His Ser Tyr Phe Asn Leu Val Leu
                165                 170                 175
Val Thr Asn Val Ala Gly Ala Gly Asp Val Gln Ser Val Ser Ile Lys
            180                 185                 190
Gly Ser Ser Thr Gly Trp Gln Pro Met Ser Arg Asn Trp Gly Gln Asn
        195                 200                 205
Trp Gln Ser Asn Ser Leu Leu Asp Gly Gln Ser Leu Ser Phe Gln Val
210                 215                 220
Thr Ala Ser Asp Gly Arg Thr Val Thr Ser Asn Gly Val Ala Pro Ala
225                 230                 235                 240
Gly Trp Gln Phe Gly Gln Thr Phe Glu Gly Ala Gln Phe
                245                 250

<210> SEQ ID NO 10
<211> LENGTH: 849
<212> TYPE: DNA
<213> ORGANISM: Zea mays
<220> FEATURE:
<221> NAME/KEY: CDS
<222> LOCATION: (1)...(849)

<400> SEQUENCE: 10 atg ggc tcc cct tcc tcc ctc ccc gcc gcg gcg gcg ctc gtg ctc ctg      48
Met Gly Ser Pro Ser Ser Leu Pro Ala Ala Ala Ala Leu Val Leu Leu
1               5                   10                  15 gcc ctg ctc gcc gga gcc cag tgc cgc gag gcc cag ttc gac gcc gcg      96
Ala Leu Leu Ala Gly Ala Gln Cys Arg Glu Ala Gln Phe Asp Ala Ala
                20                  25                  30 gac gcc ggc gcg gag aac ttc aac acc agc gag gcc gcc gtg tac tgg     144
Asp Ala Gly Ala Glu Asn Phe Asn Thr Ser Glu Ala Ala Val Tyr Trp
            35                  40                  45 ggc ccc tgg cag aag gcc cgg gcc acc tgg tac ggc cag ccc aac ggc     192
Gly Pro Trp Gln Lys Ala Arg Ala Thr Trp Tyr Gly Gln Pro Asn Gly
        50                  55                  60 gcc ggc ccg gac gac aac ggt ggt gcg tgc ggc ttc aag cac acc aac     240
Ala Gly Pro Asp Asp Asn Gly Gly Ala Cys Gly Phe Lys His Thr Asn
65                  70                  75                  80 cag tac ccc ttc atg tcc atg ggc tcc tgc gga aac cag cca ttg ttc     288
Gln Tyr Pro Phe Met Ser Met Gly Ser Cys Gly Asn Gln Pro Leu Phe
                85                  90                  95 aag gac ggc aag gga tgc ggc tcc tgc tac aag att cgg tgc agg aag     336
Lys Asp Gly Lys Gly Cys Gly Ser Cys Tyr Lys Ile Arg Cys Arg Lys
                100                 105                 110 gac ccg tcc tgc tcc ggg cgg acg gag acg gtg atc atc acc gac atg     384
Asp Pro Ser Cys Ser Gly Arg Thr Glu Thr Val Ile Ile Thr Asp Met
            115                 120                 125 aac tac tac ccg gtg tcc aag tac cac ttc gac ctc agc ggc acg gcg     432
Asn Tyr Tyr Pro Val Ser Lys Tyr His Phe Asp Leu Ser Gly Thr Ala
        130                 135                 140 ttc ggc agg ctg gcc aag ccc ggc ctc aac gac aag ctc cgc cac tcg     480
Phe Gly Arg Leu Ala Lys Pro Gly Leu Asn Asp Lys Leu Arg His Ser
145                 150                 155                 160 ggc atc atc gac atc gag ttc acc agg gtg ccg tgc gag ttc cct ggc     528
Gly Ile Ile Asp Ile Glu Phe Thr Arg Val Pro Cys Glu Phe Pro Gly
```

```
                165                 170                 175
ctc aag atc ggg ttc cac gtg gag gag tac tcg aag ccc cgt cta ctt    576
Leu Lys Ile Gly Phe His Val Glu Glu Tyr Ser Lys Pro Arg Leu Leu
            180                 185                 190 cgc ggg tgc tgg tgg agt acg agg acg gcg aac ggc gac gtg gtg cag    624
Arg Gly Cys Trp Trp Ser Thr Arg Thr Ala Asn Gly Asp Val Val Gln
        195                 200                 205 gtg gac ctg atg gag tcc aag acg gcg cgc ggg ccg ccg acg ggg cgg    672
Val Asp Leu Met Glu Ser Lys Thr Ala Arg Gly Pro Pro Thr Gly Arg
    210                 215                 220 tgg gcg ccg atg cgc gag tcc tgg ggc tcc atc tgg cgc atg gac acc    720
Trp Ala Pro Met Arg Glu Ser Trp Gly Ser Ile Trp Arg Met Asp Thr
225                 230                 235                 240 aac cac cgc atg cag ccg ccc ttc tcc atc cgc atc cgc aac gag tcc    768
Asn His Arg Met Gln Pro Pro Phe Ser Ile Arg Ile Arg Asn Glu Ser
                245                 250                 255 ggc aag acg ctc gtc gcc agg aac gtc atc ccg gcc aac tgg agg ccc    816
Gly Lys Thr Leu Val Ala Arg Asn Val Ile Pro Ala Asn Trp Arg Pro
            260                 265                 270 aac acc ttc tac cgc tcc ttc gtc cag tac agc                        849
Asn Thr Phe Tyr Arg Ser Phe Val Gln Tyr Ser
        275                 280

<210> SEQ ID NO 11
<211> LENGTH: 283
<212> TYPE: PRT
<213> ORGANISM: Zea mays

<400> SEQUENCE: 11

Met Gly Ser Pro Ser Ser Leu Pro Ala Ala Ala Leu Val Leu Leu
 1               5                  10                  15

Ala Leu Leu Ala Gly Ala Gln Cys Arg Glu Ala Gln Phe Asp Ala Ala
            20                  25                  30

Asp Ala Gly Ala Glu Asn Phe Asn Thr Ser Glu Ala Ala Val Tyr Trp
        35                  40                  45

Gly Pro Trp Gln Lys Ala Arg Ala Thr Trp Tyr Gly Gln Pro Asn Gly
    50                  55                  60

Ala Gly Pro Asp Asp Asn Gly Ala Cys Gly Phe Lys His Thr Asn
65                  70                  75                  80

Gln Tyr Pro Phe Met Ser Met Gly Ser Cys Gly Asn Gln Pro Leu Phe
                85                  90                  95

Lys Asp Gly Lys Gly Cys Gly Ser Cys Tyr Lys Ile Arg Cys Arg Lys
            100                 105                 110

Asp Pro Ser Cys Ser Gly Arg Thr Glu Thr Val Ile Ile Thr Asp Met
        115                 120                 125

Asn Tyr Tyr Pro Val Ser Lys Tyr His Phe Asp Leu Ser Gly Thr Ala
    130                 135                 140

Phe Gly Arg Leu Ala Lys Pro Gly Leu Asn Asp Lys Leu Arg His Ser
145                 150                 155                 160

Gly Ile Ile Asp Ile Glu Phe Thr Arg Val Pro Cys Glu Phe Pro Gly
                165                 170                 175

Leu Lys Ile Gly Phe His Val Glu Glu Tyr Ser Lys Pro Arg Leu Leu
            180                 185                 190

Arg Gly Cys Trp Trp Ser Thr Arg Thr Ala Asn Gly Asp Val Val Gln
        195                 200                 205

Val Asp Leu Met Glu Ser Lys Thr Ala Arg Gly Pro Pro Thr Gly Arg
    210                 215                 220
```

```
Trp Ala Pro Met Arg Glu Ser Trp Gly Ser Ile Trp Arg Met Asp Thr
225                 230                 235                 240

Asn His Arg Met Gln Pro Pro Phe Ser Ile Arg Ile Arg Asn Glu Ser
            245                 250                 255

Gly Lys Thr Leu Val Ala Arg Asn Val Ile Pro Ala Asn Trp Arg Pro
        260                 265                 270

Asn Thr Phe Tyr Arg Ser Phe Val Gln Tyr Ser
    275                 280

<210> SEQ ID NO 12
<211> LENGTH: 1389
<212> TYPE: DNA
<213> ORGANISM: Zea mays
<220> FEATURE:
<221> NAME/KEY: CDS
<222> LOCATION: (272)...(1039)
<220> FEATURE:
<221> NAME/KEY: misc_feature
<222> LOCATION: 1372
<223> OTHER INFORMATION: n = a, c, g, or t

<400> SEQUENCE: 12
ccacgcgtcc gcaagccaac aaccatcccg ctcctcctcc ctccgtcagg ctgtcactgt      60 cccccctcacc gccgccgtcc tcgtcaccac acctcacccg ttgctcccac tccttccaga   120
accacctcct cgccaccgtg ctgcctgcc ctgcccgcta taagactctt cactcccgct     180
gcgacgcagt cctcacaagc accagaccaa ttaactagct tcttctagct ctagctaggc   240
tcgtctgctg caagaaggta acagcgcagg c atg gag ggg aag gag gag gac      292
                                   Met Glu Gly Lys Glu Glu Asp
                                     1               5 gtc cgc ctg ggc gcc aac aag ttc tcg gag cgc cag ccc atc ggc acg      340
Val Arg Leu Gly Ala Asn Lys Phe Ser Glu Arg Gln Pro Ile Gly Thr
        10                  15                  20 gcg gcg cag ggc acg gac gac aag gac tac aag gag ccc ccg ccg gcg      388
Ala Ala Gln Gly Thr Asp Asp Lys Asp Tyr Lys Glu Pro Pro Pro Ala
    25                  30                  35 ccg ctc ttc gag ccc cgg gga gct caa gtc ctg gtc ctt cta ccg cgc      436
Pro Leu Phe Glu Pro Arg Gly Ala Gln Val Leu Val Leu Leu Pro Arg
40                  45                  50                  55 cgg cat cgc cga gtt cgt cgc cac ctt cct ctt cct cta cat ctc cat      484
Arg His Arg Arg Val Arg Arg His Leu Pro Leu Pro Leu His Leu His
                60                  65                  70 cct cac cgt cat ggg cgt ctc caa gtc cac ctc caa gtg cgc cac cgt      532
Pro His Arg His Gly Arg Leu Gln Val His Leu Gln Val Arg His Arg
            75                  80                  85 cgg cat cca ggg cat cgc ctg gtc ctt cgg cgg cat gat ctt cgc cct      580
Arg His Pro Gly His Arg Leu Val Leu Arg Arg His Asp Leu Arg Pro
        90                  95                 100 cgt cta ctg cac cgc cgg cat ctc cgg cgg gca cat caa ccc ggc ggt      628
Arg Leu Leu His Arg Arg His Leu Arg Arg Ala His Gln Pro Gly Gly
    105                 110                 115 gac ctt cgg gct gtt cct ggc gag gaa gtt gtc cct cac cag ggc ggt      676
Asp Leu Arg Ala Val Pro Gly Glu Glu Val Val Pro His Gln Gly Gly
120                 125                 130                 135 gtt tta cat cat cat gca gtg cct ggg cgc cat ctg cgg cgc ggg cgt      724
Val Leu His His His Ala Val Pro Gly Arg His Leu Arg Arg Gly Arg
                140                 145                 150 cgt caa ggg gtt cca gca ggg gct gta cat ggg caa cgg cgg cgg cgc      772
Arg Gln Gly Val Pro Ala Gly Ala Val His Gly Gln Arg Arg Arg Arg
            155                 160                 165 caa cgt cgt ggc gcc cgg cta cac caa ggg cga cgg cct agg cgc cga      820
Gln Arg Arg Gly Ala Arg Leu His Gln Gly Arg Arg Pro Arg Arg Arg
```

```
Gln Arg Arg Gly Ala Arg Leu His Gln Gly Arg Arg Pro Arg Arg Arg
        170                 175                 180 gat cgt cgg cac ctt cat cct cgt cta cac cgt ctt ctc cgc cac cga      868
Asp Arg Arg His Leu His Pro Arg Leu His Arg Leu Leu Arg His Arg
        185                 190                 195 cgc caa gag gaa cgc cag gga ctc cca tgt gcc gat cct cgc ccc tct      916
Arg Gln Glu Glu Arg Gln Gly Leu Pro Cys Ala Asp Pro Arg Pro Ser
200                 205                 210                 215 tcc aat cgg gtt tgc cgt gtt cct cgt cca cct ggc cac cat ccc tat      964
Ser Asn Arg Val Cys Arg Val Pro Arg Pro Pro Gly His His Pro Tyr
                220                 225                 230 cac cgg cac cgg cat caa ccc cgc gcg gag cct tgg cgc cgc cgt aat     1012
His Arg His Arg His Gln Pro Arg Ala Glu Pro Trp Arg Arg Arg Asn
                235                 240                 245 tta caa cca gca cca tgc gtg ggc tga ccactggatc ttctgggtcg           1059
Leu Gln Pro Ala Pro Cys Val Gly  *
        250                 255 gccccttcat cggcgctgcg ctggctgcca tctaccacca ggtgatcatc agggcgatcc   1119
cgttcaagag taggtcttaa aggagccgat gctgctgctt cgagatgctg ccggtcttga   1179
aaggatggat tcgtggctgt ttcaaatgat cccctactat gttacgtgga gttccattcc   1239
tctttcaaag ttcggagctg cttttatccg aacccagact tgtaattcat ctgtaccaat   1299
tgtgtaatat gccgcgcctc tgttatgtgc aattcaaaat tatgagacag cgagtcaagc   1359
tttaagagtt canaaaaaaa aaaaaaaaaa                                    1389

<210> SEQ ID NO 13
<211> LENGTH: 255
<212> TYPE: PRT
<213> ORGANISM: Zea mays
<220> FEATURE:
<223> OTHER INFORMATION: Xaa = any amino acid

<400> SEQUENCE: 13

Met Glu Gly Lys Glu Glu Asp Val Arg Leu Gly Ala Asn Lys Phe Ser
1               5                   10                  15

Glu Arg Gln Pro Ile Gly Thr Ala Ala Gln Gly Thr Asp Asp Lys Asp
            20                  25                  30

Tyr Lys Glu Pro Pro Pro Ala Pro Leu Phe Glu Pro Arg Gly Ala Gln
        35                  40                  45

Val Leu Val Leu Leu Pro Arg Arg His Arg Arg Val Arg Arg His Leu
    50                  55                  60

Pro Leu Pro Leu His Leu His Pro His Arg Gly Arg Leu Gln Val
65                  70                  75                  80

His Leu Gln Val Arg His Arg Arg His Pro Gly His Arg Leu Val Leu
                85                  90                  95

Arg Arg His Asp Leu Arg Pro Arg Leu Leu Arg Arg His Leu Arg
            100                 105                 110

Arg Ala His Gln Pro Gly Gly Asp Leu Arg Ala Val Pro Gly Glu Glu
        115                 120                 125

Val Val Pro His Gln Gly Val Leu His His Ala Val Pro Gly
    130                 135                 140

Arg His Leu Arg Arg Gly Arg Arg Gln Gly Val Pro Ala Gly Ala Val
145                 150                 155                 160

His Gly Gln Arg Arg Arg Gln Arg Gly Ala Arg Leu His Gln
                165                 170                 175

Gly Arg Arg Pro Arg Arg Arg Asp Arg Arg His Leu His Pro Arg Leu
            180                 185                 190
```

```
His Arg Leu Leu Arg His Arg Arg Gln Glu Glu Arg Gln Gly Leu Pro
            195                 200                 205

Cys Ala Asp Pro Arg Pro Ser Ser Asn Arg Val Cys Arg Val Pro Arg
    210                 215                 220

Pro Pro Gly His His Pro Tyr His Arg His His Gln Pro Arg Ala
225                 230                 235                 240

Glu Pro Trp Arg Arg Arg Asn Leu Gln Pro Ala Pro Cys Val Gly
                245                 250                 255

<210> SEQ ID NO 14
<211> LENGTH: 1238
<212> TYPE: DNA
<213> ORGANISM: Zea mays
<220> FEATURE:
<221> NAME/KEY: CDS
<222> LOCATION: (227)...(976)
<220> FEATURE:
<221> NAME/KEY: misc_feature
<222> LOCATION: 134
<223> OTHER INFORMATION: n = a, c, g, or t

<400> SEQUENCE: 14
aaatgttttg tgacgattat ccccgcaccg tccagagtac tctaacccac aagttgaggc     60
cgccctgcag cccatcagac gaggacgcgc gcgtgtataa aagctgactg gactcccagc    120
gtctgtcagc gaancgaagc agcagccaat tcgctcgagt tcagatcgag cgcgcgccaa    180
gcaagtcttc cggccggccg cgaagagcgc aatcaagcaa gacaag atg gtg aag       235
                                                  Met Val Lys
                                                    1 ctc gcc ttc gga agc gtc ggc gac tcc ttc agc gcc acc tcc atc aag      283
Leu Ala Phe Gly Ser Val Gly Asp Ser Phe Ser Ala Thr Ser Ile Lys
      5                  10                  15 gcc tac gtg gcc gag ttc atc gcc acc ctc ctc ttc gtc ttc gcc ggc      331
Ala Tyr Val Ala Glu Phe Ile Ala Thr Leu Leu Phe Val Phe Ala Gly
 20                  25                  30                  35 gtc ggt tcc gcc atc gcc tac ggg caa ctg acg aat ggc ggc gcg ctg      379
Val Gly Ser Ala Ile Ala Tyr Gly Gln Leu Thr Asn Gly Gly Ala Leu
              40                  45                  50 gac ccg gcg ggc ctg gtg gcg atc gcg atc gcg cac gcg ctg gcg ctg      427
Asp Pro Ala Gly Leu Val Ala Ile Ala Ile Ala His Ala Leu Ala Leu
          55                  60                  65 ttc gtg ggc gtg tcc gtc gcg gcg aac atc tcg ggc ggc cac ctg aac      475
Phe Val Gly Val Ser Val Ala Ala Asn Ile Ser Gly Gly His Leu Asn
      70                  75                  80 ccg gcc gtg acg ttc ggg ctg gcc gtg ggc ggc cac atc acc atc ctg      523
Pro Ala Val Thr Phe Gly Leu Ala Val Gly Gly His Ile Thr Ile Leu
 85                  90                  95 acg ggc gtc ttc tac tgg gtg gcc cag ctg ctg ggc gcc acc gtg gcg      571
Thr Gly Val Phe Tyr Trp Val Ala Gln Leu Leu Gly Ala Thr Val Ala
100                 105                 110                 115 tgc ctc ctc ctc ggg ttc gtc acc cac ggc aag gcc atc ccg acg cac      619
Cys Leu Leu Leu Gly Phe Val Thr His Gly Lys Ala Ile Pro Thr His
              120                 125                 130 gcc gtc gcg ggc atc agc gag ctg gaa ggc gtc gtg ttc gag gtc gtc      667
Ala Val Ala Gly Ile Ser Glu Leu Glu Gly Val Val Phe Glu Val Val
          135                 140                 145 atc acc ttc gcg ctc gtc tac acc gtg tac gcc acc gcc gcc gac ccc      715
Ile Thr Phe Ala Leu Val Tyr Thr Val Tyr Ala Thr Ala Ala Asp Pro
      150                 155                 160 aag aag ggc tcg ctc ggc acc atc gcg ccc atc gcc atc ggc ttc atc      763
Lys Lys Gly Ser Leu Gly Thr Ile Ala Pro Ile Ala Ile Gly Phe Ile
```

```
                165                 170                 175
gtc ggc gcc aac atc ctc gcc gcg ggg ccc ttc agc ggc ggc tcc atg      811
Val Gly Ala Asn Ile Leu Ala Ala Gly Pro Phe Ser Gly Gly Ser Met
180                 185                 190                 195 aac ccc gcc cgc tcc ttc ggc ccc gcc gtc gcc gcg ggc gac ttc gcc      859
Asn Pro Ala Arg Ser Phe Gly Pro Ala Val Ala Ala Gly Asp Phe Ala
                200                 205                 210 gga aac tgg gtc tac tgg gtc ggc ccg ctc gtc ggc ggc ggc ctc gct      907
Gly Asn Trp Val Tyr Trp Val Gly Pro Leu Val Gly Gly Gly Leu Ala
            215                 220                 225 ggc ctc gtc tac ggc gac gtc ttc att ggc ggc tcc tac cag cag gtc      955
Gly Leu Val Tyr Gly Asp Val Phe Ile Gly Gly Ser Tyr Gln Gln Val
        230                 235                 240 gcg gac cag gac tac gcc taa tttattcacc actccatctc cgctctggat        1006
Ala Asp Gln Asp Tyr Ala  *
    245 gaatggattc aaaaccgtcg tcgtttgctt ttgctcctcg ccacgttcaa ttaatggttg    1066 tgtatgcatg tatgtgccaa tatgatgtgc ctttgccctg gtccattcat ttccctttct   1126 tttttcgggg tgaaatagat gtaaagatct cgtcttgcct gccgtactcg cgctgtgttg   1186 ggaaaaattg gttttcgttc aagtttgtt tacgcaaaga aaaaaaaaaa aa            1238
```

<210> SEQ ID NO 15
<211> LENGTH: 249
<212> TYPE: PRT
<213> ORGANISM: Zea mays
<220> FEATURE:
<223> OTHER INFORMATION: Xaa = any amino acid

<400> SEQUENCE: 15

```
Met Val Lys Leu Ala Phe Gly Ser Val Gly Asp Ser Phe Ser Ala Thr
 1               5                  10                  15

Ser Ile Lys Ala Tyr Val Ala Glu Phe Ile Ala Thr Leu Leu Phe Val
                20                  25                  30

Phe Ala Gly Val Gly Ser Ala Ile Ala Tyr Gly Gln Leu Thr Asn Gly
            35                  40                  45

Gly Ala Leu Asp Pro Ala Gly Leu Val Ala Ile Ala Ile Ala His Ala
        50                  55                  60

Leu Ala Leu Phe Val Gly Val Ser Val Ala Ala Asn Ile Ser Gly Gly
65                  70                  75                  80

His Leu Asn Pro Ala Val Thr Phe Gly Leu Ala Val Gly Gly His Ile
                85                  90                  95

Thr Ile Leu Thr Gly Val Phe Tyr Trp Val Ala Gln Leu Leu Gly Ala
            100                 105                 110

Thr Val Ala Cys Leu Leu Leu Gly Phe Val Thr His Gly Lys Ala Ile
        115                 120                 125

Pro Thr His Ala Val Ala Gly Ile Ser Glu Leu Glu Gly Val Val Phe
130                 135                 140

Glu Val Val Ile Thr Phe Ala Leu Val Tyr Thr Val Tyr Ala Thr Ala
145                 150                 155                 160

Ala Asp Pro Lys Lys Gly Ser Leu Gly Thr Ile Ala Pro Ile Ala Ile
                165                 170                 175

Gly Phe Ile Val Gly Ala Asn Ile Leu Ala Ala Gly Pro Phe Ser Gly
            180                 185                 190

Gly Ser Met Asn Pro Ala Arg Ser Phe Gly Pro Ala Val Ala Ala Gly
        195                 200                 205

Asp Phe Ala Gly Asn Trp Val Tyr Trp Val Gly Pro Leu Val Gly Gly
```

Gly Leu Ala Gly Leu Val Tyr Gly Asp Val Phe Ile Gly Gly Ser Tyr
225                 230                 235                 240

Gln Gln Val Ala Asp Gln Asp Tyr Ala
            245

<210> SEQ ID NO 16
<211> LENGTH: 1170
<212> TYPE: DNA
<213> ORGANISM: Zea mays
<220> FEATURE:
<221> NAME/KEY: CDS
<222> LOCATION: (593)...(769)

<400> SEQUENCE: 16

| | |
|---|---|
| gtccattcca atctcatctc aaatctgtcc atgggctgac aagaccgcgc gctgaaaaca | 60 |
| tttgcgtggt ggctgctgca cgcagctggg cgcggagttc gtgggcacgt tcatcctcat | 120 |
| cttcttcgcg acggcggcgc cgatcgtgaa ccagaagtac ggcggcgcga tcagcccgtt | 180 |
| cgggaacgcg gcgtgcgcgg ggctggcggt ggcgaccgtg atcctgtcga cggggcacat | 240 |
| ctccggggcg cacctgaacc cgtcgctcac catcgccttc gcggcgctgc gccacttccc | 300 |
| ctggctgcag gtgcccgcgt acgtggccgt ccaggcgctg gcatccgtct cgccgccctt | 360 |
| cgcgctcaag ggcgtcttcc acccgttcct tccggcggc gtcaccgtgc cgacgccac | 420 |
| cgtctccacc gcccaggcgt tcttcaccga gttcatcatc ccttcaacc tctcttcgt | 480 |
| cgtcaccgcc gtcgccaccg acacccgcgc agtgggtgaa ctcgccggga tcgcggtggg | 540 |
| agcggccgta acgctgaaca tcctcgtcgc cgggccgacg acgggcgggt cc atg aac | 598 |
| | Met Asn |
| | 1 |
| ccg gtg agg acg ctg ggg ccg gcc gtg gcg gcg ggg aac tac cgg cag | 646 |
| Pro Val Arg Thr Leu Gly Pro Ala Val Ala Ala Gly Asn Tyr Arg Gln | |
| 5                       10                      15 | |
| ctc tgg atc tac ctg ctg gcc ccg acg ctg ggc gcg ttg gcg ggg gcc | 694 |
| Leu Trp Ile Tyr Leu Leu Ala Pro Thr Leu Gly Ala Leu Ala Gly Ala | |
| 20                      25                      30 | |
| agc gtg tac aag gcg gtg aag ctc agg gac gag aac ggt gag acg ccg | 742 |
| Ser Val Tyr Lys Ala Val Lys Leu Arg Asp Glu Asn Gly Glu Thr Pro | |
| 35                      40                      45                      50 | |
| cgc acg cag cgc agc ttc cgc cgc tga cgacgcacac tggccacggg | 789 |
| Arg Thr Gln Arg Ser Phe Arg Arg * | |
|                     55 | |
| cgcgagacat tgtccggccg tgtcacgcac gcccgcgtcc tcctccgccg ccgcgtaacg | 849 |
| cacggccacg acgtgtccgc ggtcgtacgt gctcgtgtctg tgtgtaccaa taaataagcc | 909 |
| ccgttttgct tcgtccagaa cggtccagtg ctatgtgtac gtggtctgtg ttgtgatttg | 969 |
| cgaattggat tattgtgggt cgtctcgtcg aggtctctcg ggtgtcgggt gggtctgatg | 1029 |
| cgatccatca gcgtcgtgtc cgaataaaag ccacgccgat gcgccggctg acgggcatct | 1089 |
| ggatgtgtga tttctgaaca agatttgctt aatttcactt gcttaaaaaa aaaaaaaaa | 1149 |
| aaaaaaaaaa aaaaaaaaaa a | 1170 |

<210> SEQ ID NO 17
<211> LENGTH: 58
<212> TYPE: PRT
<213> ORGANISM: Zea mays

<400> SEQUENCE: 17

Met Asn Pro Val Arg Thr Leu Gly Pro Ala Val Ala Ala Gly Asn Tyr

```
                    1               5                  10                 15
              Arg Gln Leu Trp Ile Tyr Leu Leu Ala Pro Thr Leu Gly Ala Leu Ala
                              20                  25                  30

Gly Ala Ser Val Tyr Lys Ala Val Lys Leu Arg Asp Glu Asn Gly Glu
                          35                  40                  45

Thr Pro Arg Thr Gln Arg Ser Phe Arg Arg
                      50                  55

<210> SEQ ID NO 18
<211> LENGTH: 1557
<212> TYPE: DNA
<213> ORGANISM: Zea mays
<220> FEATURE:
<221> NAME/KEY: CDS
<222> LOCATION: (1)...(1557)

<400> SEQUENCE: 18 atg gct cgt ggc gac ggc ggg cag ctg gcg gag ctg tcc gcg ggg gtc       48
Met Ala Arg Gly Asp Gly Gly Gln Leu Ala Glu Leu Ser Ala Gly Val
  1               5                  10                  15 cgc ggc gcg gcc gcg gtg gtg gac cac gtg gcc ccg atc agc ctc ggg       96
Arg Gly Ala Ala Ala Val Val Asp His Val Ala Pro Ile Ser Leu Gly
             20                  25                  30 agg ctc atc ctc gcc ggc atg gtc gcc ggc ggc gtg cag tac ggc tgg      144
Arg Leu Ile Leu Ala Gly Met Val Ala Gly Gly Val Gln Tyr Gly Trp
         35                  40                  45 gcg ctg cag ctc tcc ctc ctc acg ccc tac gtg cag act ctg ggg ctt      192
Ala Leu Gln Leu Ser Leu Leu Thr Pro Tyr Val Gln Thr Leu Gly Leu
     50                  55                  60 tca cat gcg ctc act tca ttc atg tgg ctc tgc ggc cct att gcc ggc      240
Ser His Ala Leu Thr Ser Phe Met Trp Leu Cys Gly Pro Ile Ala Gly
 65                  70                  75                  80 tta gtg gtc caa ccg ctg gtt ggc ctg tac agc gac agg tgt aca tcg      288
Leu Val Val Gln Pro Leu Val Gly Leu Tyr Ser Asp Arg Cys Thr Ser
                 85                  90                  95 aga tgg ggg aga cgg agg ccg ttt atc ctg aca ggg tgc atg ctc atc      336
Arg Trp Gly Arg Arg Arg Pro Phe Ile Leu Thr Gly Cys Met Leu Ile
            100                 105                 110 tgc gtt gcc gtc att gtt gtc gga ttc tcg tca gac atc gga gct gct      384
Cys Val Ala Val Ile Val Val Gly Phe Ser Ser Asp Ile Gly Ala Ala
        115                 120                 125 cta ggg gac acg aag gaa cac tgc agc ctc tac cac ggt cct cgt tgg      432
Leu Gly Asp Thr Lys Glu His Cys Ser Leu Tyr His Gly Pro Arg Trp
    130                 135                 140 cac gct gcg atc gtg tac gtt ctg ggg ttt tgg ctc ctt gac ttc tcc      480
His Ala Ala Ile Val Tyr Val Leu Gly Phe Trp Leu Leu Asp Phe Ser
145                 150                 155                 160 aac aac act gtg cag ggt cca gca cgt gct atg atg gct gat cta tgt      528
Asn Asn Thr Val Gln Gly Pro Ala Arg Ala Met Met Ala Asp Leu Cys
                165                 170                 175 gac cat cat ggg cca agt gcg gct aac tcc atc ttc tgt tct tgg atg      576
Asp His His Gly Pro Ser Ala Ala Asn Ser Ile Phe Cys Ser Trp Met
            180                 185                 190 gcg ctg gga aac atc cta ggc tac tcc tct ggc tcc acg aac aat tgg      624
Ala Leu Gly Asn Ile Leu Gly Tyr Ser Ser Gly Ser Thr Asn Asn Trp
        195                 200                 205 cac aag tgg ttt ccc ttc ctt aaa acg agc gcc tgc tgt gag gcc tgt      672
His Lys Trp Phe Pro Phe Leu Lys Thr Ser Ala Cys Cys Glu Ala Cys
    210                 215                 220 gcg aac ctg aaa ggt gca ttt ctg gtg gcc gtg gtg ttc cta gtc ctg      720
Ala Asn Leu Lys Gly Ala Phe Leu Val Ala Val Val Phe Leu Val Leu
```

```
                 225                 230                 235                 240
tgc ctg acg gta acc ctg atc ttc gcc aag gag gtg ccg tac aga gcg      768
Cys Leu Thr Val Thr Leu Ile Phe Ala Lys Glu Val Pro Tyr Arg Ala
                 245                 250                 255 aac gag aac ctc ccg acg acg aag gcc ggc ggc gag gtc gag act gag      816
Asn Glu Asn Leu Pro Thr Thr Lys Ala Gly Gly Glu Val Glu Thr Glu
                 260                 265                 270 cct acc ggg cca ctt gcc gtg ctc aag ggc ttc aag gac ctg cct ccc      864
Pro Thr Gly Pro Leu Ala Val Leu Lys Gly Phe Lys Asp Leu Pro Pro
                 275                 280                 285 ggg atg ccg tcc gtg ctc ctc gtg act gcc atc acc tgg ctt tcg tgg      912
Gly Met Pro Ser Val Leu Leu Val Thr Ala Ile Thr Trp Leu Ser Trp
                 290                 295                 300 ttc ccg ttc atc ctc tac gac acc gac tgg atg ggc cgg gag atc tac      960
Phe Pro Phe Ile Leu Tyr Asp Thr Asp Trp Met Gly Arg Glu Ile Tyr
305                 310                 315                 320 cac ggc gac ccc aag ggg agc aac gcc cag atc tcg gcg ttc aac gaa     1008
His Gly Asp Pro Lys Gly Ser Asn Ala Gln Ile Ser Ala Phe Asn Glu
                 325                 330                 335 ggt gtc cga gtc ggc gcg ttc ggg ctg cta ctc aac tcg gtt att cta     1056
Gly Val Arg Val Gly Ala Phe Gly Leu Leu Leu Asn Ser Val Ile Leu
                 340                 345                 350 ggg ttc agc tcg ttc ctg atc gag ccc atg tgc cgg aag gtc ggg ccg     1104
Gly Phe Ser Ser Phe Leu Ile Glu Pro Met Cys Arg Lys Val Gly Pro
                 355                 360                 365 agg gtg gtg tgg gtg acg agc aac ttc atg gtc tgc gtc gcc atg gcg     1152
Arg Val Val Trp Val Thr Ser Asn Phe Met Val Cys Val Ala Met Ala
                 370                 375                 380 gcc acc gcg ctg atc agc ttc tgg tcg ctc agg gac tac cac ggg tac     1200
Ala Thr Ala Leu Ile Ser Phe Trp Ser Leu Arg Asp Tyr His Gly Tyr
385                 390                 395                 400 gtg cag gac gcc atc acc gcg aac gcc agc atc aag gcc gtc tgc ctc     1248
Val Gln Asp Ala Ile Thr Ala Asn Ala Ser Ile Lys Ala Val Cys Leu
                 405                 410                 415 gtc ctc ttc gcc ttc ctg ggc gtc cct ctc gcc atc ctg tac agc gtc     1296
Val Leu Phe Ala Phe Leu Gly Val Pro Leu Ala Ile Leu Tyr Ser Val
                 420                 425                 430 ccg ttc gcg gtg acg gcg cag ctg gcg gcc acc cgg ggc ggc ggg cag     1344
Pro Phe Ala Val Thr Ala Gln Leu Ala Ala Thr Arg Gly Gly Gly Gln
                 435                 440                 445 ggg ctg tgc acc ggc gtc ctc aac atc tcc atc gtc atc cct cag gtg     1392
Gly Leu Cys Thr Gly Val Leu Asn Ile Ser Ile Val Ile Pro Gln Val
450                 455                 460 atc atc gcg ctg ggc gcc ggc ccg tgg gac gcg ctg ttc ggg aag ggc     1440
Ile Ile Ala Leu Gly Ala Gly Pro Trp Asp Ala Leu Phe Gly Lys Gly
465                 470                 475                 480 aac atc ccg gcg ttc ggc gtc gcg tcg gcc ttc gcc ctc gtc ggc ggc     1488
Asn Ile Pro Ala Phe Gly Val Ala Ser Ala Phe Ala Leu Val Gly Gly
                 485                 490                 495 gtc gtg ggc gtg ttc ctg ctg ccc aag atc tcc aag cgc cag ttc cgg     1536
Val Val Gly Val Phe Leu Leu Pro Lys Ile Ser Lys Arg Gln Phe Arg
                 500                 505                 510 gcc gtc agc gcg ggc ggc cac                                         1557
Ala Val Ser Ala Gly Gly His
                 515
```

<210> SEQ ID NO 19
<211> LENGTH: 519
<212> TYPE: PRT
<213> ORGANISM: Zea mays

<400> SEQUENCE: 19

```
Met Ala Arg Gly Asp Gly Gly Gln Leu Ala Glu Leu Ser Ala Gly Val
 1               5                  10                  15
Arg Gly Ala Ala Ala Val Val Asp His Val Ala Pro Ile Ser Leu Gly
             20                  25                  30
Arg Leu Ile Leu Ala Gly Met Val Ala Gly Val Gln Tyr Gly Trp
         35                  40                  45
Ala Leu Gln Leu Ser Leu Leu Thr Pro Tyr Val Gln Thr Leu Gly Leu
     50                  55                  60
Ser His Ala Leu Thr Ser Phe Met Trp Leu Cys Gly Pro Ile Ala Gly
 65                  70                  75                  80
Leu Val Val Gln Pro Leu Val Gly Leu Tyr Ser Asp Arg Cys Thr Ser
                 85                  90                  95
Arg Trp Gly Arg Arg Pro Phe Ile Leu Thr Gly Cys Met Leu Ile
             100                 105                 110
Cys Val Ala Val Ile Val Val Gly Phe Ser Ser Asp Ile Gly Ala Ala
            115                 120                 125
Leu Gly Asp Thr Lys Glu His Cys Ser Leu Tyr His Gly Pro Arg Trp
    130                 135                 140
His Ala Ala Ile Val Tyr Val Leu Gly Phe Trp Leu Leu Asp Phe Ser
145                 150                 155                 160
Asn Asn Thr Val Gln Gly Pro Ala Arg Ala Met Met Ala Asp Leu Cys
                165                 170                 175
Asp His His Gly Pro Ser Ala Ala Asn Ser Ile Phe Cys Ser Trp Met
            180                 185                 190
Ala Leu Gly Asn Ile Leu Gly Tyr Ser Ser Gly Ser Thr Asn Asn Trp
        195                 200                 205
His Lys Trp Phe Pro Phe Leu Lys Thr Ser Ala Cys Cys Glu Ala Cys
    210                 215                 220
Ala Asn Leu Lys Gly Ala Phe Leu Val Ala Val Val Phe Leu Val Leu
225                 230                 235                 240
Cys Leu Thr Val Thr Leu Ile Phe Ala Lys Glu Val Pro Tyr Arg Ala
                245                 250                 255
Asn Glu Asn Leu Pro Thr Thr Lys Ala Gly Gly Glu Val Glu Thr Glu
            260                 265                 270
Pro Thr Gly Pro Leu Ala Val Leu Lys Gly Phe Lys Asp Leu Pro Pro
        275                 280                 285
Gly Met Pro Ser Val Leu Leu Val Thr Ala Ile Thr Trp Leu Ser Trp
    290                 295                 300
Phe Pro Phe Ile Leu Tyr Asp Thr Asp Trp Met Gly Arg Glu Ile Tyr
305                 310                 315                 320
His Gly Asp Pro Lys Gly Ser Asn Ala Gln Ile Ser Ala Phe Asn Glu
                325                 330                 335
Gly Val Arg Val Gly Ala Phe Gly Leu Leu Leu Asn Ser Val Ile Leu
            340                 345                 350
Gly Phe Ser Ser Phe Leu Ile Glu Pro Met Cys Arg Lys Val Gly Pro
        355                 360                 365
Arg Val Val Trp Val Thr Ser Asn Phe Met Val Cys Val Ala Met Ala
    370                 375                 380
Ala Thr Ala Leu Ile Ser Phe Trp Ser Leu Arg Asp Tyr His Gly Tyr
385                 390                 395                 400
Val Gln Asp Ala Ile Thr Ala Asn Ala Ser Ile Lys Ala Val Cys Leu
                405                 410                 415
```

```
Val Leu Phe Ala Phe Leu Gly Val Pro Leu Ala Ile Leu Tyr Ser Val
            420                 425                 430

Pro Phe Ala Val Thr Ala Gln Leu Ala Thr Arg Gly Gly Gln
        435                 440                 445

Gly Leu Cys Thr Gly Val Leu Asn Ile Ser Val Ile Pro Gln Val
    450                 455                 460

Ile Ile Ala Leu Gly Ala Gly Pro Trp Asp Ala Leu Phe Gly Lys Gly
465                 470                 475                 480

Asn Ile Pro Ala Phe Gly Val Ala Ser Ala Phe Ala Leu Val Gly Gly
                485                 490                 495

Val Val Gly Val Phe Leu Leu Pro Lys Ile Ser Lys Arg Gln Phe Arg
            500                 505                 510

Ala Val Ser Ala Gly Gly His
            515

<210> SEQ ID NO 20
<211> LENGTH: 2022
<212> TYPE: DNA
<213> ORGANISM: Zea mays
<220> FEATURE:
<221> NAME/KEY: CDS
<222> LOCATION: (1)...(2022)

<400> SEQUENCE: 20 atg gag acc cgg gac acg gat gcg acg ccg ctc ccc tac tcg tac acg    48
Met Glu Thr Arg Asp Thr Asp Ala Thr Pro Leu Pro Tyr Ser Tyr Thr
1               5                   10                  15 ccg ctg ccg gcc gcc gac gcc gcg tcg gcc gag gtc tcc ggc acc ggc    96
Pro Leu Pro Ala Ala Asp Ala Ala Ser Ala Glu Val Ser Gly Thr Gly
                20                  25                  30 agg acg cgg agc agg cgg cgg ccc ctc tgc gcg gcg gcg ctc gtg ctc    144
Arg Thr Arg Ser Arg Arg Arg Pro Leu Cys Ala Ala Ala Leu Val Leu
            35                  40                  45 tcc gcc gcg ctg ctc cta gcc gtg gcc gcg ctc gtc ggc gtc ggt agc    192
Ser Ala Ala Leu Leu Leu Ala Val Ala Ala Leu Val Gly Val Gly Ser
    50                  55                  60 cgg ccc ggc gcg gtg ggg atg aca gag tcg gcg gcc tcg tcg ccg acg    240
Arg Pro Gly Ala Val Gly Met Thr Glu Ser Ala Ala Ser Ser Pro Thr
65                  70                  75                  80 ccg agc agg agc agg ggc ccc gag gcc ggc gtg tcc gag aag acg tcc    288
Pro Ser Arg Ser Arg Gly Pro Glu Ala Gly Val Ser Glu Lys Thr Ser
                85                  90                  95 ggc gcg tct gac gac ggc ggc agg ctc cgt gga gcc ggc ggg aac gcc    336
Gly Ala Ser Asp Asp Gly Gly Arg Leu Arg Gly Ala Gly Gly Asn Ala
                100                 105                 110 ttc ccg tgg agc aat gcg atg ctg cag tgg cag cgc acg gga ttc cac    384
Phe Pro Trp Ser Asn Ala Met Leu Gln Trp Gln Arg Thr Gly Phe His
            115                 120                 125 ttc cag ccg cag aag aac tgg atg aac gac ccc aat ggc ccc gtg tac    432
Phe Gln Pro Gln Lys Asn Trp Met Asn Asp Pro Asn Gly Pro Val Tyr
        130                 135                 140 tac aag ggc tgg tac cac ctc ttc tac cag tac aac cct gac ggc gcc    480
Tyr Lys Gly Trp Tyr His Leu Phe Tyr Gln Tyr Asn Pro Asp Gly Ala
145                 150                 155                 160 atc tgg ggc aac aag atc gcg tgg ggc cac gcc gtg tcc cgc gac ctg    528
Ile Trp Gly Asn Lys Ile Ala Trp Gly His Ala Val Ser Arg Asp Leu
                165                 170                 175 atc cgc tgg cgc cgc ctc ccg ctg gcc atg gtg ccc gac cag tgg tac    576
Ile Arg Trp Arg Arg Leu Pro Leu Ala Met Val Pro Asp Gln Trp Tyr
                180                 185                 190
```

```
gac acc aac ggc gtg tgg acg ggg tcc gcc acc acg ctc ccc gac ggc     624
Asp Thr Asn Gly Val Trp Thr Gly Ser Ala Thr Thr Leu Pro Asp Gly
        195                 200                 205 cgc ctc gca atg ctc tac agg ggc tcc acc aac gcc tcc gtc cag gtg     672
Arg Leu Ala Met Leu Tyr Arg Gly Ser Thr Asn Ala Ser Val Gln Val
    210                 215                 220 cag tgc ctg gcc gtg ccc gcc gac gac gcc gac ccg ctg ctc acc aac     720
Gln Cys Leu Ala Val Pro Ala Asp Asp Ala Asp Pro Leu Leu Thr Asn
225                 230                 235                 240 tgg acc aag tac gag ggc aac ccg gtg ctg tac ccg ccc ccg ggc atc     768
Trp Thr Lys Tyr Glu Gly Asn Pro Val Leu Tyr Pro Pro Pro Gly Ile
                245                 250                 255 ggg ccc aag gac ttc cgc gac ccc acc acg gtc tgg atc gac ccc tcg     816
Gly Pro Lys Asp Phe Arg Asp Pro Thr Thr Val Trp Ile Asp Pro Ser
            260                 265                 270 gac ggc gca tgg cgc gtc gtc atc ggc tcc aag gac gac gac ggc cac     864
Asp Gly Ala Trp Arg Val Val Ile Gly Ser Lys Asp Asp Asp Gly His
        275                 280                 285 gcg ggc atc gcc gtc gtc tac cgc acc acg gac ctg gtg cac ttc gag     912
Ala Gly Ile Ala Val Val Tyr Arg Thr Thr Asp Leu Val His Phe Glu
    290                 295                 300 ctc ctc ccg ggc ctg ctg cac cgc gtc gac ggc acc ggc atg tgg gag     960
Leu Leu Pro Gly Leu Leu His Arg Val Asp Gly Thr Gly Met Trp Glu
305                 310                 315                 320 tgc atc gac ttc tac ccc gtc gcc aca cga ggc agg gcg tcg gcc aac    1008
Cys Ile Asp Phe Tyr Pro Val Ala Thr Arg Gly Arg Ala Ser Ala Asn
                325                 330                 335 ggc gtc gac atg tcc gac gcc atc gcc agc aac gga gcc gtc gcc ggg    1056
Gly Val Asp Met Ser Asp Ala Ile Ala Ser Asn Gly Ala Val Ala Gly
            340                 345                 350 gac gtc ctg cac gtc atg aag gcc agc atg gac gac gac cgc cac gac    1104
Asp Val Leu His Val Met Lys Ala Ser Met Asp Asp Asp Arg His Asp
        355                 360                 365 tac tac gcg ctg ggg agg tac gac gcg gcc gcc aac gcc tgg acg ccg    1152
Tyr Tyr Ala Leu Gly Arg Tyr Asp Ala Ala Ala Asn Ala Trp Thr Pro
    370                 375                 380 atc gac gcc ggc agg gac gtc ggc atc ggc ctg cgc tac gac tgg ggc    1200
Ile Asp Ala Gly Arg Asp Val Gly Ile Gly Leu Arg Tyr Asp Trp Gly
385                 390                 395                 400 aag ttc tac gcg tcc aag acg ttc tac gac ccg gcc aag cgc cgc cgc    1248
Lys Phe Tyr Ala Ser Lys Thr Phe Tyr Asp Pro Ala Lys Arg Arg Arg
                405                 410                 415 gtg ctg tgg gga tgg gtc ggc gag aca gac tcg gag cgc gcg gac gtg    1296
Val Leu Trp Gly Trp Val Gly Glu Thr Asp Ser Glu Arg Ala Asp Val
            420                 425                 430 tcc aag gga tgg gcg tcg ctg cag ggt atc ccc cgg acg gtg ctc ctg    1344
Ser Lys Gly Trp Ala Ser Leu Gln Gly Ile Pro Arg Thr Val Leu Leu
        435                 440                 445 gac acc aag acg ggc agc aac ctg ctt cag tgg ccc gtg gag gag gtg    1392
Asp Thr Lys Thr Gly Ser Asn Leu Leu Gln Trp Pro Val Glu Glu Val
    450                 455                 460 gag acg ctg cgc acc aac tcc acc gac ctc agc ggc atc acc atc gac    1440
Glu Thr Leu Arg Thr Asn Ser Thr Asp Leu Ser Gly Ile Thr Ile Asp
465                 470                 475                 480 tac ggc tcc gtg ttc ccg ctc aac ctc cgc cgc gcc acc cag ctg gac    1488
Tyr Gly Ser Val Phe Pro Leu Asn Leu Arg Arg Ala Thr Gln Leu Asp
                485                 490                 495 atc gag gcg gag ttc cag ctg gac cgc cgc gcc gtc atg tcg ctc aac    1536
Ile Glu Ala Glu Phe Gln Leu Asp Arg Arg Ala Val Met Ser Leu Asn
            500                 505                 510
```

```
gag gcg gac gtg ggc tac aac tgc agc acc agc ggg ggc gcc gcc ggc    1584
Glu Ala Asp Val Gly Tyr Asn Cys Ser Thr Ser Gly Gly Ala Ala Gly
    515                 520                 525 cgc ggc gcg ctg ggg ccc ttc ggc ctg ttc gtc ctc gcc gac cgc cgc    1632
Arg Gly Ala Leu Gly Pro Phe Gly Leu Phe Val Leu Ala Asp Arg Arg
530                 535                 540 ctc cgc cgc gag cag acg gcc gtc tac ttc tac gtg gcc aag ggc ctg    1680
Leu Arg Arg Glu Gln Thr Ala Val Tyr Phe Tyr Val Ala Lys Gly Leu
545                 550                 555                 560 gac ggc tcc ctc gcc acg cac ttc tgc cag gac gag tcc cgc tcc tcc    1728
Asp Gly Ser Leu Ala Thr His Phe Cys Gln Asp Glu Ser Arg Ser Ser
                565                 570                 575 agc gcc acc gac atc gtc aag cgc gtc gtc ggc agc gcc gtc ccc gtg    1776
Ser Ala Thr Asp Ile Val Lys Arg Val Val Gly Ser Ala Val Pro Val
            580                 585                 590 ctg gag gac gag gcc acg ctc tcg ctc cgg gtg ctc gtc gac cac tcc    1824
Leu Glu Asp Glu Ala Thr Leu Ser Leu Arg Val Leu Val Asp His Ser
        595                 600                 605 atc gtc gag agc ttc gcg cag ggc ggg agg tcc acc gcc aca tcg cgc    1872
Ile Val Glu Ser Phe Ala Gln Gly Gly Arg Ser Thr Ala Thr Ser Arg
    610                 615                 620 gtc tac ccc acc gag gcc atc tac gcc aac gcc ggc gtc ttc ctc ttc    1920
Val Tyr Pro Thr Glu Ala Ile Tyr Ala Asn Ala Gly Val Phe Leu Phe
625                 630                 635                 640 aac aac gcc acc gcc gcg cgg gtc acg gcc acg aag ctc gtc gtc cac    1968
Asn Asn Ala Thr Ala Ala Arg Val Thr Ala Thr Lys Leu Val Val His
                645                 650                 655 gag atg gac tcg tca tac aac cac gac tac atg gcg ccg gtg gca gac    2016
Glu Met Asp Ser Ser Tyr Asn His Asp Tyr Met Ala Pro Val Ala Asp
            660                 665                 670 atc tga                                                            2022
Ile *

<210> SEQ ID NO 21
<211> LENGTH: 673
<212> TYPE: PRT
<213> ORGANISM: Zea mays

<400> SEQUENCE: 21

Met Glu Thr Arg Asp Thr Asp Ala Thr Pro Leu Pro Tyr Ser Tyr Thr
1               5                   10                  15

Pro Leu Pro Ala Ala Asp Ala Ala Ser Ala Glu Val Ser Gly Thr Gly
            20                  25                  30

Arg Thr Arg Ser Arg Arg Pro Leu Cys Ala Ala Leu Val Leu
        35                  40                  45

Ser Ala Ala Leu Leu Leu Ala Val Ala Ala Leu Val Gly Val Gly Ser
    50                  55                  60

Arg Pro Gly Ala Val Gly Met Thr Glu Ser Ala Ala Ser Ser Pro Thr
65                  70                  75                  80

Pro Ser Arg Ser Arg Gly Pro Glu Ala Gly Val Ser Glu Lys Thr Ser
            85                  90                  95

Gly Ala Ser Asp Asp Gly Gly Arg Leu Arg Gly Ala Gly Gly Asn Ala
                100                 105                 110

Phe Pro Trp Ser Asn Ala Met Leu Gln Trp Gln Arg Thr Gly Phe His
            115                 120                 125

Phe Gln Pro Gln Lys Asn Trp Met Asn Asp Pro Asn Gly Pro Val Tyr
        130                 135                 140

Tyr Lys Gly Trp Tyr His Leu Phe Tyr Gln Tyr Asn Pro Asp Gly Ala
145                 150                 155                 160
```

```
Ile Trp Gly Asn Lys Ile Ala Trp Gly His Ala Val Ser Arg Asp Leu
                165                 170                 175
Ile Arg Trp Arg Arg Leu Pro Leu Ala Met Val Pro Asp Gln Trp Tyr
                180                 185                 190
Asp Thr Asn Gly Val Trp Thr Gly Ser Ala Thr Thr Leu Pro Asp Gly
                195                 200                 205
Arg Leu Ala Met Leu Tyr Arg Gly Ser Thr Asn Ala Ser Val Gln Val
                210                 215                 220
Gln Cys Leu Ala Val Pro Ala Asp Asp Ala Asp Pro Leu Leu Thr Asn
225                 230                 235                 240
Trp Thr Lys Tyr Glu Gly Asn Pro Val Leu Tyr Pro Pro Pro Gly Ile
                245                 250                 255
Gly Pro Lys Asp Phe Arg Asp Pro Thr Thr Val Trp Ile Asp Pro Ser
                260                 265                 270
Asp Gly Ala Trp Arg Val Val Ile Gly Ser Lys Asp Asp Gly His
                275                 280                 285
Ala Gly Ile Ala Val Val Tyr Arg Thr Thr Asp Leu Val His Phe Glu
                290                 295                 300
Leu Leu Pro Gly Leu Leu His Arg Val Asp Gly Thr Gly Met Trp Glu
305                 310                 315                 320
Cys Ile Asp Phe Tyr Pro Val Ala Thr Arg Gly Arg Ala Ser Ala Asn
                325                 330                 335
Gly Val Asp Met Ser Asp Ala Ile Ala Ser Asn Gly Ala Val Ala Gly
                340                 345                 350
Asp Val Leu His Val Met Lys Ala Ser Met Asp Asp Arg His Asp
                355                 360                 365
Tyr Tyr Ala Leu Gly Arg Tyr Asp Ala Ala Ala Asn Ala Trp Thr Pro
                370                 375                 380
Ile Asp Ala Gly Arg Asp Val Gly Ile Gly Leu Arg Tyr Asp Trp Gly
385                 390                 395                 400
Lys Phe Tyr Ala Ser Lys Thr Phe Tyr Asp Pro Ala Lys Arg Arg
                405                 410                 415
Val Leu Trp Gly Trp Val Gly Glu Thr Asp Ser Glu Arg Ala Asp Val
                420                 425                 430
Ser Lys Gly Trp Ala Ser Leu Gln Gly Ile Pro Arg Thr Val Leu Leu
                435                 440                 445
Asp Thr Lys Thr Gly Ser Asn Leu Leu Gln Trp Pro Val Glu Glu Val
                450                 455                 460
Glu Thr Leu Arg Thr Asn Ser Thr Asp Leu Ser Gly Ile Thr Ile Asp
465                 470                 475                 480
Tyr Gly Ser Val Phe Pro Leu Asn Leu Arg Arg Ala Thr Gln Leu Asp
                485                 490                 495
Ile Glu Ala Glu Phe Gln Leu Asp Arg Arg Ala Val Met Ser Leu Asn
                500                 505                 510
Glu Ala Asp Val Gly Tyr Asn Cys Ser Thr Ser Gly Ala Ala Gly
                515                 520                 525
Arg Gly Ala Leu Gly Pro Phe Gly Leu Phe Val Leu Ala Asp Arg Arg
                530                 535                 540
Leu Arg Arg Glu Gln Thr Ala Val Tyr Phe Tyr Val Ala Lys Gly Leu
545                 550                 555                 560
Asp Gly Ser Leu Ala Thr His Phe Cys Gln Asp Glu Ser Arg Ser Ser
                565                 570                 575
Ser Ala Thr Asp Ile Val Lys Arg Val Val Gly Ser Ala Val Pro Val
```

-continued

```
                 580                 585                 590
Leu Glu Asp Glu Ala Thr Leu Ser Leu Arg Val Leu Asp His Ser
            595                 600                 605

Ile Val Glu Ser Phe Ala Gln Gly Gly Arg Ser Thr Ala Thr Ser Arg
        610                 615                 620

Val Tyr Pro Thr Glu Ala Ile Tyr Ala Asn Ala Gly Val Phe Leu Phe
625                 630                 635                 640

Asn Asn Ala Thr Ala Ala Arg Val Thr Ala Thr Lys Leu Val Val His
                645                 650                 655

Glu Met Asp Ser Ser Tyr Asn His Asp Tyr Met Ala Pro Val Ala Asp
            660                 665                 670

Ile

<210> SEQ ID NO 22
<211> LENGTH: 1638
<212> TYPE: DNA
<213> ORGANISM: Zea mays
<220> FEATURE:
<221> NAME/KEY: CDS
<222> LOCATION: (1)...(1638)

<400> SEQUENCE: 22 atg ggc ctg ggt ttg gga gct ctt ctc aaa tcc ggg ggc ctc tcg gtc      48
Met Gly Leu Gly Leu Gly Ala Leu Leu Lys Ser Gly Gly Leu Ser Val
1               5                   10                  15 tcg gat cac gac gcc atc gtc tcg att aac atc ttc atc gcg ctg ctc      96
Ser Asp His Asp Ala Ile Val Ser Ile Asn Ile Phe Ile Ala Leu Leu
                20                  25                  30 tgc agc tgc att gtc atc ggc cac ttg ctg gaa ggg aac cga tgg gtg     144
Cys Ser Cys Ile Val Ile Gly His Leu Leu Glu Gly Asn Arg Trp Val
            35                  40                  45 aac gag tcc atc acc gcg ctt gtc atg ggc ctc atc acc gga ggc gtc     192
Asn Glu Ser Ile Thr Ala Leu Val Met Gly Leu Ile Thr Gly Gly Val
        50                  55                  60 atc ctg ctg gtt act aat ggg aca aac tca cgc att ctt gtg ttc agc     240
Ile Leu Leu Val Thr Asn Gly Thr Asn Ser Arg Ile Leu Val Phe Ser
65                  70                  75                  80 gag gac ctg ttt ttc ata tat tta ctt ccg ccg ata atc ttc aat gcc     288
Glu Asp Leu Phe Phe Ile Tyr Leu Leu Pro Pro Ile Ile Phe Asn Ala
                85                  90                  95 ggg ttt caa gta aag aaa aag caa ttc ttc cgc aac ttt ata acg att     336
Gly Phe Gln Val Lys Lys Lys Gln Phe Phe Arg Asn Phe Ile Thr Ile
            100                 105                 110 att ttg ttt ggt gct att ggg act ctg att tcc ttt gta ata atc tct     384
Ile Leu Phe Gly Ala Ile Gly Thr Leu Ile Ser Phe Val Ile Ile Ser
        115                 120                 125 ctt ggt gct atg ggg ttg ttc aag aaa ctt gat gtt ggt cca ctc gag     432
Leu Gly Ala Met Gly Leu Phe Lys Lys Leu Asp Val Gly Pro Leu Glu
    130                 135                 140 ctt ggg gac tat ctt gca att ggt gct att ttc tcg gca aca gat tct     480
Leu Gly Asp Tyr Leu Ala Ile Gly Ala Ile Phe Ser Ala Thr Asp Ser
145                 150                 155                 160 gtt tgc acc tta cag gtg ctt aac cag gat gaa aca ccc cta ctc tat     528
Val Cys Thr Leu Gln Val Leu Asn Gln Asp Glu Thr Pro Leu Leu Tyr
                165                 170                 175 agt cta gtt ttt ggt gaa ggt gtt gtt aat gat gcc aca tct gtt gtg     576
Ser Leu Val Phe Gly Glu Gly Val Val Asn Asp Ala Thr Ser Val Val
            180                 185                 190 ctc ttc aat gca att gaa aac ctt gat att gat aat ttt gat gct att     624
Leu Phe Asn Ala Ile Glu Asn Leu Asp Ile Asp Asn Phe Asp Ala Ile
```

-continued

```
              195                 200                 205
gtt ctg ttg aat ttc gtc gga aaa ttt ctc tac ttg ttc ttc acc agc    672
Val Leu Leu Asn Phe Val Gly Lys Phe Leu Tyr Leu Phe Phe Thr Ser
    210                 215                 220 acc ata ctt gga gta gct acc ggg ttg ctt agt gca tac att atc aag    720
Thr Ile Leu Gly Val Ala Thr Gly Leu Leu Ser Ala Tyr Ile Ile Lys
225                 230                 235                 240 aag ctc tgt ttt gcc aga cat tca act gat aga gaa gtt tct atc atg    768
Lys Leu Cys Phe Ala Arg His Ser Thr Asp Arg Glu Val Ser Ile Met
                245                 250                 255 ata ctc atg gca tac ctt tca tac atg ata tca atg ctg ttg gac ctg    816
Ile Leu Met Ala Tyr Leu Ser Tyr Met Ile Ser Met Leu Leu Asp Leu
            260                 265                 270 agt gga att ctt act gtc ttc ttc tgt gga ata gta atg tca cat tac    864
Ser Gly Ile Leu Thr Val Phe Phe Cys Gly Ile Val Met Ser His Tyr
        275                 280                 285 act tgg cat aat gtg aca gaa agt tct agg gtt acc acc aag cat act    912
Thr Trp His Asn Val Thr Glu Ser Ser Arg Val Thr Thr Lys His Thr
    290                 295                 300 ttt gca act tta tca ttc att gca gaa att ttc ctc ttc ctc tat gtt    960
Phe Ala Thr Leu Ser Phe Ile Ala Glu Ile Phe Leu Phe Leu Tyr Val
305                 310                 315                 320 ggg atg gat gca ttg gac att gag aag tgg aaa tta gct agt agc agt   1008
Gly Met Asp Ala Leu Asp Ile Glu Lys Trp Lys Leu Ala Ser Ser Ser
                325                 330                 335 cct aag aaa cca att gct tta agt gca att att ttg ggc ttg gtt atg   1056
Pro Lys Lys Pro Ile Ala Leu Ser Ala Ile Ile Leu Gly Leu Val Met
            340                 345                 350 gtt gga aga gcg gca ttt gta ttc cct ttg tcg ttc tta tcc aac cta   1104
Val Gly Arg Ala Ala Phe Val Phe Pro Leu Ser Phe Leu Ser Asn Leu
        355                 360                 365 agc aaa aag gag gcc cgt cca aag atc tcc ttc aag caa caa gta atc   1152
Ser Lys Lys Glu Ala Arg Pro Lys Ile Ser Phe Lys Gln Gln Val Ile
    370                 375                 380 ata tgg tgg gct ggt ctc atg aga gga gca gtg tca att gcg ctt gcc   1200
Ile Trp Trp Ala Gly Leu Met Arg Gly Ala Val Ser Ile Ala Leu Ala
385                 390                 395                 400 tat aac aag ttt aca gca tct ggt cac act gaa gtg cga gtc aat gct   1248
Tyr Asn Lys Phe Thr Ala Ser Gly His Thr Glu Val Arg Val Asn Ala
                405                 410                 415 atc atg atc acc agc aca gtt att gtt gtt cta ttc agc aca atg gtt   1296
Ile Met Ile Thr Ser Thr Val Ile Val Val Leu Phe Ser Thr Met Val
            420                 425                 430 ttc ggc ctg ctg acg aag ccg ctc ctc agt ctc ctc atc cca cca agg   1344
Phe Gly Leu Leu Thr Lys Pro Leu Leu Ser Leu Leu Ile Pro Pro Arg
        435                 440                 445 act gga ctg aac acg tcg tct ctg ctc tca agc cag tct atg ctg gac   1392
Thr Gly Leu Asn Thr Ser Ser Leu Leu Ser Ser Gln Ser Met Leu Asp
    450                 455                 460 cca ctc ctt act agc atg atg ggg tct gac ttt gat gta ggg cag atc   1440
Pro Leu Leu Thr Ser Met Met Gly Ser Asp Phe Asp Val Gly Gln Ile
465                 470                 475                 480 aac tcc cct caa tac aac ctc cag ttc att ctc acc gcg cca gct cgc   1488
Asn Ser Pro Gln Tyr Asn Leu Gln Phe Ile Leu Thr Ala Pro Ala Arg
                485                 490                 495 tcc gtc cat cgc ctt tgg cgc aag ttt gac gat cgg ttc atg cgc ccg   1536
Ser Val His Arg Leu Trp Arg Lys Phe Asp Asp Arg Phe Met Arg Pro
            500                 505                 510 gtg ttc ggg ggg cga ggt ttc gtc ccc ttt gtg cct ggt tcg ccg gtg   1584
Val Phe Gly Gly Arg Gly Phe Val Pro Phe Val Pro Gly Ser Pro Val
```

```
                  515                 520                 525
gag agg agt gtc cct gaa tct cac ctg ggc act gtg acg gag gct gag    1632
Glu Arg Ser Val Pro Glu Ser His Leu Gly Thr Val Thr Glu Ala Glu
    530                 535                 540 ggc agt                                                            1638
Gly Ser
545

<210> SEQ ID NO 23
<211> LENGTH: 546
<212> TYPE: PRT
<213> ORGANISM: Zea mays

<400> SEQUENCE: 23

Met Gly Leu Gly Leu Gly Ala Leu Leu Lys Ser Gly Gly Leu Ser Val
 1               5                  10                  15

Ser Asp His Asp Ala Ile Val Ser Ile Asn Ile Phe Ile Ala Leu Leu
            20                  25                  30

Cys Ser Cys Ile Val Ile Gly His Leu Leu Glu Gly Asn Arg Trp Val
        35                  40                  45

Asn Glu Ser Ile Thr Ala Leu Val Met Gly Leu Ile Thr Gly Gly Val
50                  55                  60

Ile Leu Leu Val Thr Asn Gly Thr Asn Ser Arg Ile Leu Val Phe Ser
65                  70                  75                  80

Glu Asp Leu Phe Phe Ile Tyr Leu Leu Pro Pro Ile Ile Phe Asn Ala
                85                  90                  95

Gly Phe Gln Val Lys Lys Lys Gln Phe Phe Arg Asn Phe Ile Thr Ile
            100                 105                 110

Ile Leu Phe Gly Ala Ile Gly Thr Leu Ile Ser Phe Val Ile Ile Ser
        115                 120                 125

Leu Gly Ala Met Gly Leu Phe Lys Lys Leu Asp Val Gly Pro Leu Glu
    130                 135                 140

Leu Gly Asp Tyr Leu Ala Ile Gly Ala Ile Phe Ser Ala Thr Asp Ser
145                 150                 155                 160

Val Cys Thr Leu Gln Val Leu Asn Gln Asp Glu Thr Pro Leu Leu Tyr
                165                 170                 175

Ser Leu Val Phe Gly Glu Gly Val Val Asn Asp Ala Thr Ser Val Val
            180                 185                 190

Leu Phe Asn Ala Ile Glu Asn Leu Asp Ile Asp Asn Phe Asp Ala Ile
        195                 200                 205

Val Leu Leu Asn Phe Val Gly Lys Phe Leu Tyr Leu Phe Phe Thr Ser
    210                 215                 220

Thr Ile Leu Gly Val Ala Thr Gly Leu Leu Ser Ala Tyr Ile Ile Lys
225                 230                 235                 240

Lys Leu Cys Phe Ala Arg His Ser Thr Asp Arg Glu Val Ser Ile Met
                245                 250                 255

Ile Leu Met Ala Tyr Leu Ser Tyr Met Ile Ser Met Leu Leu Asp Leu
            260                 265                 270

Ser Gly Ile Leu Thr Val Phe Phe Cys Gly Ile Val Met Ser His Tyr
        275                 280                 285

Thr Trp His Asn Val Thr Glu Ser Ser Arg Val Thr Thr Lys His Thr
    290                 295                 300

Phe Ala Thr Leu Ser Phe Ile Ala Glu Ile Phe Leu Phe Leu Tyr Val
305                 310                 315                 320

Gly Met Asp Ala Leu Asp Ile Glu Lys Trp Lys Leu Ala Ser Ser Ser
                325                 330                 335
```

```
Pro Lys Lys Pro Ile Ala Leu Ser Ala Ile Ile Leu Gly Leu Val Met
            340                 345                 350

Val Gly Arg Ala Ala Phe Val Phe Pro Leu Ser Phe Leu Ser Asn Leu
        355                 360                 365

Ser Lys Lys Glu Ala Arg Pro Lys Ile Ser Phe Lys Gln Gln Val Ile
370                 375                 380

Ile Trp Trp Ala Gly Leu Met Arg Gly Ala Val Ser Ile Ala Leu Ala
385                 390                 395                 400

Tyr Asn Lys Phe Thr Ala Ser Gly His Thr Glu Val Arg Val Asn Ala
            405                 410                 415

Ile Met Ile Thr Ser Thr Val Ile Val Val Leu Phe Ser Thr Met Val
            420                 425                 430

Phe Gly Leu Leu Thr Lys Pro Leu Leu Ser Leu Ile Pro Pro Arg
        435                 440                 445

Thr Gly Leu Asn Thr Ser Ser Leu Leu Ser Ser Gln Ser Met Leu Asp
        450                 455                 460

Pro Leu Leu Thr Ser Met Met Gly Ser Asp Phe Asp Val Gly Gln Ile
465                 470                 475                 480

Asn Ser Pro Gln Tyr Asn Leu Gln Phe Ile Leu Thr Ala Pro Ala Arg
            485                 490                 495

Ser Val His Arg Leu Trp Arg Lys Phe Asp Asp Arg Phe Met Arg Pro
        500                 505                 510

Val Phe Gly Gly Arg Gly Phe Val Pro Phe Val Pro Gly Ser Pro Val
        515                 520                 525

Glu Arg Ser Val Pro Glu Ser His Leu Gly Thr Val Thr Glu Ala Glu
        530                 535                 540

Gly Ser
545

<210> SEQ ID NO 24
<211> LENGTH: 2286
<212> TYPE: DNA
<213> ORGANISM: Zea mays
<220> FEATURE:
<221> NAME/KEY: CDS
<222> LOCATION: (1)...(2286)

<400> SEQUENCE: 24 atg gcg atc ctc tcg gcg ctc gcc acc gag gtg ctc atc ccc gtc gcc      48
Met Ala Ile Leu Ser Ala Leu Ala Thr Glu Val Leu Ile Pro Val Ala
1               5                   10                  15 gcc gtc atc ggc atc gcc ttc gcc gtc gtg cag tgg gtg gtc gtg tcg      96
Ala Val Ile Gly Ile Ala Phe Ala Val Val Gln Trp Val Val Val Ser
            20                  25                  30 cgc gtg aag ctc tcc ccg gcc gcg tcc ggc ggc agc ggc ggc aag gcc     144
Arg Val Lys Leu Ser Pro Ala Ala Ser Gly Gly Ser Gly Gly Lys Ala
        35                  40                  45 ggc tac gcc gac tcc ctc atc gag gag gag gag ggg ctc aac gac cac     192
Gly Tyr Ala Asp Ser Leu Ile Glu Glu Glu Glu Gly Leu Asn Asp His
    50                  55                  60 aac gtc gtc gtc aag tgc gcc gag atc cag aac gcc atc tcc gaa gga     240
Asn Val Val Val Lys Cys Ala Glu Ile Gln Asn Ala Ile Ser Glu Gly
65                  70                  75                  80 gca aca tcg ttt ctt ttc acc gag tac caa tat gtt ggt atc ttc atg     288
Ala Thr Ser Phe Leu Phe Thr Glu Tyr Gln Tyr Val Gly Ile Phe Met
                85                  90                  95 gct atc ttc gct gtt gtg atc ttc ctc ttc ctt ggt tcg gtt gag gga     336
Ala Ile Phe Ala Val Val Ile Phe Leu Phe Leu Gly Ser Val Glu Gly
```

|  |  |  |  |  |  |  |  |  |  |  |  |  |  |  |  |
|---|---|---|---|---|---|---|---|---|---|---|---|---|---|---|---|
|  |  |  |  |  | 100 |  |  |  | 105 |  |  |  | 110 |  |  |
| ttc | agc | acg | aag | agc | cag | ccc | tgc | aca | tat | agc | aag | gac | aag | tac | tgc | 384 |
| Phe | Ser | Thr | Lys | Ser | Gln | Pro | Cys | Thr | Tyr | Ser | Lys | Asp | Lys | Tyr | Cys |
|  |  | 115 |  |  |  |  | 120 |  |  |  |  | 125 |  |  |  |
| aag | cct | gcg | ctg | ttc | act | gca | ctc | ttt | agc | act | gtg | tcc | ttc | ttg | ctt | 432 |
| Lys | Pro | Ala | Leu | Phe | Thr | Ala | Leu | Phe | Ser | Thr | Val | Ser | Phe | Leu | Leu |
| 130 |  |  |  |  | 135 |  |  |  |  | 140 |  |  |  |  |  |
| gga | gcc | atc | acc | tct | ctg | gtc | tct | ggt | ttc | ctt | ggc | atg | aag | att | gcc | 480 |
| Gly | Ala | Ile | Thr | Ser | Leu | Val | Ser | Gly | Phe | Leu | Gly | Met | Lys | Ile | Ala |
| 145 |  |  |  |  | 150 |  |  |  |  | 155 |  |  |  |  | 160 |
| aca | tat | gcg | aat | gcc | aga | act | acc | ctg | gaa | gct | agg | aag | ggt | gtt | ggc | 528 |
| Thr | Tyr | Ala | Asn | Ala | Arg | Thr | Thr | Leu | Glu | Ala | Arg | Lys | Gly | Val | Gly |
|  |  |  |  | 165 |  |  |  |  | 170 |  |  |  |  | 175 |  |
| aag | gct | ttt | atc | act | gct | ttc | cgc | tct | ggc | gct | gtt | atg | ggt | ttc | ctg | 576 |
| Lys | Ala | Phe | Ile | Thr | Ala | Phe | Arg | Ser | Gly | Ala | Val | Met | Gly | Phe | Leu |
|  |  |  | 180 |  |  |  |  | 185 |  |  |  |  | 190 |  |  |
| ctt | gca | tca | agt | ggg | ctt | gtg | gtt | ctg | tac | atc | aca | att | aat | gta | ttt | 624 |
| Leu | Ala | Ser | Ser | Gly | Leu | Val | Val | Leu | Tyr | Ile | Thr | Ile | Asn | Val | Phe |
|  |  | 195 |  |  |  |  | 200 |  |  |  |  | 205 |  |  |  |
| aag | ttg | tat | tac | ggt | gat | gac | tgg | gag | ggt | ctt | ttt | gag | tcc | atc | act | 672 |
| Lys | Leu | Tyr | Tyr | Gly | Asp | Asp | Trp | Glu | Gly | Leu | Phe | Glu | Ser | Ile | Thr |
| 210 |  |  |  |  | 215 |  |  |  |  | 220 |  |  |  |  |  |
| ggc | tat | ggt | ctt | ggt | ggg | tcg | tcc | atg | gct | ctc | ttc | gga | aga | gtt | ggt | 720 |
| Gly | Tyr | Gly | Leu | Gly | Gly | Ser | Ser | Met | Ala | Leu | Phe | Gly | Arg | Val | Gly |
| 225 |  |  |  |  | 230 |  |  |  |  | 235 |  |  |  |  | 240 |
| gga | ggt | atc | tac | aca | aag | gct | gct | gat | gtt | ggt | gcc | gat | ctt | gtt | gga | 768 |
| Gly | Gly | Ile | Tyr | Thr | Lys | Ala | Ala | Asp | Val | Gly | Ala | Asp | Leu | Val | Gly |
|  |  |  |  | 245 |  |  |  |  | 250 |  |  |  |  | 255 |  |
| aag | gtc | gag | agg | aac | att | cct | gag | gat | gat | cct | agg | aac | cca | gct | gtg | 816 |
| Lys | Val | Glu | Arg | Asn | Ile | Pro | Glu | Asp | Asp | Pro | Arg | Asn | Pro | Ala | Val |
|  |  |  | 260 |  |  |  |  | 265 |  |  |  |  | 270 |  |  |
| att | gct | gat | aat | gtc | ggt | gac | aat | gtt | ggt | gac | att | gct | gga | atg | gga | 864 |
| Ile | Ala | Asp | Asn | Val | Gly | Asp | Asn | Val | Gly | Asp | Ile | Ala | Gly | Met | Gly |
|  |  | 275 |  |  |  |  | 280 |  |  |  |  | 285 |  |  |  |
| tct | gat | ctc | ttt | ggg | tca | tac | gca | gag | tct | tct | tgt | gct | gcc | ctt | gtt | 912 |
| Ser | Asp | Leu | Phe | Gly | Ser | Tyr | Ala | Glu | Ser | Ser | Cys | Ala | Ala | Leu | Val |
| 290 |  |  |  |  | 295 |  |  |  |  | 300 |  |  |  |  |  |
| gtt | gcg | tct | att | tca | tct | ttc | gga | atc | gac | cat | gat | ttc | act | ggg | atg | 960 |
| Val | Ala | Ser | Ile | Ser | Ser | Phe | Gly | Ile | Asp | His | Asp | Phe | Thr | Gly | Met |
| 305 |  |  |  |  | 310 |  |  |  |  | 315 |  |  |  |  | 320 |
| tgc | tac | cca | ctc | ctt | gtt | agc | tct | gtt | ggt | atc | att | gtc | tgc | ttg | atc | 1008 |
| Cys | Tyr | Pro | Leu | Leu | Val | Ser | Ser | Val | Gly | Ile | Ile | Val | Cys | Leu | Ile |
|  |  |  |  | 325 |  |  |  |  | 330 |  |  |  |  | 335 |  |
| acc | acc | ctt | ttt | gct | act | gat | ttc | ttt | gaa | gtc | aag | gct | gtg | aaa | gaa | 1056 |
| Thr | Thr | Leu | Phe | Ala | Thr | Asp | Phe | Phe | Glu | Val | Lys | Ala | Val | Lys | Glu |
|  |  |  | 340 |  |  |  |  | 345 |  |  |  |  | 350 |  |  |
| att | gag | cct | gca | ctt | aag | aag | cag | ctc | atc | atc | tcc | acc | gtc | ctg | atg | 1104 |
| Ile | Glu | Pro | Ala | Leu | Lys | Lys | Gln | Leu | Ile | Ile | Ser | Thr | Val | Leu | Met |
|  |  | 355 |  |  |  |  | 360 |  |  |  |  | 365 |  |  |  |
| act | ttt | ggt | att | gct | cta | atc | agc | tgg | ttg | gcc | ctt | cca | gct | aag | ttc | 1152 |
| Thr | Phe | Gly | Ile | Ala | Leu | Ile | Ser | Trp | Leu | Ala | Leu | Pro | Ala | Lys | Phe |
| 370 |  |  |  |  | 375 |  |  |  |  | 380 |  |  |  |  |  |
| acc | atc | tac | aac | ttc | ggt | act | cag | aag | gag | gtt | tcc | aac | tgg | ggt | ttg | 1200 |
| Thr | Ile | Tyr | Asn | Phe | Gly | Thr | Gln | Lys | Glu | Val | Ser | Asn | Trp | Gly | Leu |
| 385 |  |  |  |  | 390 |  |  |  |  | 395 |  |  |  |  | 400 |
| ttc | ttc | tgt | gtt | tca | att | ggt | ctg | tgg | gct | ggt | ttg | att | att | ggt | ttt | 1248 |
| Phe | Phe | Cys | Val | Ser | Ile | Gly | Leu | Trp | Ala | Gly | Leu | Ile | Ile | Gly | Phe |
|  |  |  |  | 405 |  |  |  |  | 410 |  |  |  |  | 415 |  |
| gtc | aca | gaa | tac | tac | act | agc | aat | gca | tac | agt | cct | gtg | caa | gat | gtt | 1296 |
| Val | Thr | Glu | Tyr | Tyr | Thr | Ser | Asn | Ala | Tyr | Ser | Pro | Val | Gln | Asp | Val |

```
                     420              425               430
gcg gat tcg tgc aga act ggt gct gcc act aat gtc att ttt ggt ctt    1344
Ala Asp Ser Cys Arg Thr Gly Ala Ala Thr Asn Val Ile Phe Gly Leu
        435               440               445 gct ctt gga tac aag tct gtt atc atc ccg att ttc gct att gct gtt    1392
Ala Leu Gly Tyr Lys Ser Val Ile Ile Pro Ile Phe Ala Ile Ala Val
450               455               460 agc atc tat gtc agt ttc tcc att gct gcg atg tac ggc att gca gtt    1440
Ser Ile Tyr Val Ser Phe Ser Ile Ala Ala Met Tyr Gly Ile Ala Val
465               470               475               480 gcc gct ctt ggt atg ctg agc aca atc gca act ggt ctt gct att gat    1488
Ala Ala Leu Gly Met Leu Ser Thr Ile Ala Thr Gly Leu Ala Ile Asp
        485               490               495 gct tat ggt ccc atc agt gac aat gct ggt ggt att gct gag atg gct    1536
Ala Tyr Gly Pro Ile Ser Asp Asn Ala Gly Gly Ile Ala Glu Met Ala
500               505               510 gga atg agc cac aga atc cgt gag aga act gat gct ctt gat gct gct    1584
Gly Met Ser His Arg Ile Arg Glu Arg Thr Asp Ala Leu Asp Ala Ala
        515               520               525 ggc aac aca act gct gct att gga aag ggg ttt gcc att ggt tca gct    1632
Gly Asn Thr Thr Ala Ala Ile Gly Lys Gly Phe Ala Ile Gly Ser Ala
530               535               540 gct ctt gtg tcc ctg gcg ctt ttt ggt gcc ttt gtc agc aga gct gga    1680
Ala Leu Val Ser Leu Ala Leu Phe Gly Ala Phe Val Ser Arg Ala Gly
545               550               555               560 gtg aag gtc gtc gac gtc ctc tcc ccc aag gtt ttc att ggt ttg att    1728
Val Lys Val Val Asp Val Leu Ser Pro Lys Val Phe Ile Gly Leu Ile
        565               570               575 gtt gga gcc atg ctt ccg tac tgg ttc tct gcc atg acc atg aag agt    1776
Val Gly Ala Met Leu Pro Tyr Trp Phe Ser Ala Met Thr Met Lys Ser
580               585               590 gtt gga agc gct gcc ctg aag atg gtg gag gag gtc cgc agg cag ttc    1824
Val Gly Ser Ala Ala Leu Lys Met Val Glu Glu Val Arg Arg Gln Phe
        595               600               605 aac acc att cct ggg ttg atg gag gga aca gcc aag ccc gac tac gca    1872
Asn Thr Ile Pro Gly Leu Met Glu Gly Thr Ala Lys Pro Asp Tyr Ala
610               615               620 acc tgt gtg aag atc tcc act gat gct tcc atc aag gag atg att cct    1920
Thr Cys Val Lys Ile Ser Thr Asp Ala Ser Ile Lys Glu Met Ile Pro
625               630               635               640 ccg ggc gct ctg gtc atg ctg act ccc ctc atc gtt gga acc ctc ttt    1968
Pro Gly Ala Leu Val Met Leu Thr Pro Leu Ile Val Gly Thr Leu Phe
        645               650               655 ggc gtc gag act ctc tcc ggc gtt ctt gct ggt gcc ctg gtt tct gga    2016
Gly Val Glu Thr Leu Ser Gly Val Leu Ala Gly Ala Leu Val Ser Gly
660               665               670 gtg cag atc gcc atc tct gct tcc aac acc ggc ggt gca tgg gac aat    2064
Val Gln Ile Ala Ile Ser Ala Ser Asn Thr Gly Gly Ala Trp Asp Asn
        675               680               685 gcc aag aag tac atc gag gct ggt gcc agc gag cac gcg agg acc ctc    2112
Ala Lys Lys Tyr Ile Glu Ala Gly Ala Ser Glu His Ala Arg Thr Leu
690               695               700 ggt ccc aag gga tcc gac tgc cac aag gcc gct gtg atc ggt gac acc    2160
Gly Pro Lys Gly Ser Asp Cys His Lys Ala Ala Val Ile Gly Asp Thr
705               710               715               720 att ggt gac ccc ctg aag gac acc tcc ggc ccg tcc ctc aac atc ctc    2208
Ile Gly Asp Pro Leu Lys Asp Thr Ser Gly Pro Ser Leu Asn Ile Leu
        725               730               735 atc aag ctc atg gcc gtg gag tcc ctc gtg ttt gcc ccc ttc ttt gcc    2256
Ile Lys Leu Met Ala Val Glu Ser Leu Val Phe Ala Pro Phe Phe Ala
```

| | | 740 | | | 745 | | | 750 | | | |
|---|---|---|---|---|---|---|---|---|---|---|---|
| acc | cag | ggt | ggc | ctg | ctc | ttc | aag | tac | ctg | | 2286 |
| Thr | Gln | Gly | Gly | Leu | Leu | Phe | Lys | Tyr | Leu | | |
| | 755 | | | | | 760 | | | | | |

<210> SEQ ID NO 25
<211> LENGTH: 762
<212> TYPE: PRT
<213> ORGANISM: Zea mays

<400> SEQUENCE: 25

```
Met Ala Ile Leu Ser Ala Leu Ala Thr Glu Val Leu Ile Pro Val Ala
 1               5                  10                  15

Ala Val Ile Gly Ile Ala Phe Ala Val Val Gln Trp Val Val Ser
             20                  25                  30

Arg Val Lys Leu Ser Pro Ala Ala Ser Gly Gly Ser Gly Gly Lys Ala
             35                  40                  45

Gly Tyr Ala Asp Ser Leu Ile Glu Glu Glu Gly Leu Asn Asp His
     50                  55                  60

Asn Val Val Lys Cys Ala Glu Ile Gln Asn Ala Ile Ser Glu Gly
 65                  70                  75                  80

Ala Thr Ser Phe Leu Phe Thr Glu Tyr Gln Tyr Val Gly Ile Phe Met
                 85                  90                  95

Ala Ile Phe Ala Val Val Ile Phe Leu Phe Leu Gly Ser Val Glu Gly
                100                 105                 110

Phe Ser Thr Lys Ser Gln Pro Cys Thr Tyr Ser Lys Asp Lys Tyr Cys
                115                 120                 125

Lys Pro Ala Leu Phe Thr Ala Leu Phe Ser Thr Val Ser Phe Leu Leu
            130                 135                 140

Gly Ala Ile Thr Ser Leu Val Ser Gly Phe Leu Gly Met Lys Ile Ala
145                 150                 155                 160

Thr Tyr Ala Asn Ala Arg Thr Thr Leu Glu Ala Arg Lys Gly Val Gly
                165                 170                 175

Lys Ala Phe Ile Thr Ala Phe Arg Ser Gly Ala Val Met Gly Phe Leu
            180                 185                 190

Leu Ala Ser Ser Gly Leu Val Val Leu Tyr Ile Thr Ile Asn Val Phe
            195                 200                 205

Lys Leu Tyr Tyr Gly Asp Asp Trp Glu Gly Leu Phe Glu Ser Ile Thr
        210                 215                 220

Gly Tyr Gly Leu Gly Gly Ser Ser Met Ala Leu Phe Gly Arg Val Gly
225                 230                 235                 240

Gly Gly Ile Tyr Thr Lys Ala Ala Asp Val Gly Ala Asp Leu Val Gly
                245                 250                 255

Lys Val Glu Arg Asn Ile Pro Glu Asp Asp Pro Arg Asn Pro Ala Val
            260                 265                 270

Ile Ala Asp Asn Val Gly Asp Asn Val Gly Asp Ile Ala Gly Met Gly
        275                 280                 285

Ser Asp Leu Phe Gly Ser Tyr Ala Glu Ser Ser Cys Ala Ala Leu Val
    290                 295                 300

Val Ala Ser Ile Ser Ser Phe Gly Ile Asp His Asp Phe Thr Gly Met
305                 310                 315                 320

Cys Tyr Pro Leu Leu Val Ser Ser Val Gly Ile Ile Val Cys Leu Ile
                325                 330                 335

Thr Thr Leu Phe Ala Thr Asp Phe Phe Glu Val Lys Ala Val Lys Glu
            340                 345                 350
```

```
Ile Glu Pro Ala Leu Lys Lys Gln Leu Ile Ile Ser Thr Val Leu Met
            355                 360                 365

Thr Phe Gly Ile Ala Leu Ile Ser Trp Leu Ala Leu Pro Ala Lys Phe
    370                 375                 380

Thr Ile Tyr Asn Phe Gly Thr Gln Lys Glu Val Ser Asn Trp Gly Leu
385                 390                 395                 400

Phe Phe Cys Val Ser Ile Gly Leu Trp Ala Gly Leu Ile Ile Gly Phe
                405                 410                 415

Val Thr Glu Tyr Tyr Thr Ser Asn Ala Tyr Ser Pro Val Gln Asp Val
            420                 425                 430

Ala Asp Ser Cys Arg Thr Gly Ala Ala Thr Asn Val Ile Phe Gly Leu
            435                 440                 445

Ala Leu Gly Tyr Lys Ser Val Ile Ile Pro Ile Phe Ala Ile Ala Val
450                 455                 460

Ser Ile Tyr Val Ser Phe Ser Ile Ala Ala Met Tyr Gly Ile Ala Val
465                 470                 475                 480

Ala Ala Leu Gly Met Leu Ser Thr Ile Ala Thr Gly Leu Ala Ile Asp
                485                 490                 495

Ala Tyr Gly Pro Ile Ser Asp Asn Ala Gly Gly Ile Ala Glu Met Ala
            500                 505                 510

Gly Met Ser His Arg Ile Arg Glu Arg Thr Asp Ala Leu Asp Ala Ala
            515                 520                 525

Gly Asn Thr Thr Ala Ala Ile Gly Lys Gly Phe Ala Ile Gly Ser Ala
            530                 535                 540

Ala Leu Val Ser Leu Ala Leu Phe Gly Ala Phe Val Ser Arg Ala Gly
545                 550                 555                 560

Val Lys Val Val Asp Val Leu Ser Pro Lys Val Phe Ile Gly Leu Ile
                565                 570                 575

Val Gly Ala Met Leu Pro Tyr Trp Phe Ser Ala Met Thr Met Lys Ser
            580                 585                 590

Val Gly Ser Ala Ala Leu Lys Met Val Glu Glu Val Arg Arg Gln Phe
            595                 600                 605

Asn Thr Ile Pro Gly Leu Met Glu Gly Thr Ala Lys Pro Asp Tyr Ala
            610                 615                 620

Thr Cys Val Lys Ile Ser Thr Asp Ala Ser Ile Lys Glu Met Ile Pro
625                 630                 635                 640

Pro Gly Ala Leu Val Met Leu Thr Pro Leu Ile Val Gly Thr Leu Phe
                645                 650                 655

Gly Val Glu Thr Leu Ser Gly Val Leu Ala Gly Ala Leu Val Ser Gly
            660                 665                 670

Val Gln Ile Ala Ile Ser Ala Ser Asn Thr Gly Gly Ala Trp Asp Asn
            675                 680                 685

Ala Lys Lys Tyr Ile Glu Ala Gly Ala Ser Glu His Ala Arg Thr Leu
            690                 695                 700

Gly Pro Lys Gly Ser Asp Cys His Lys Ala Ala Val Ile Gly Asp Thr
705                 710                 715                 720

Ile Gly Asp Pro Leu Lys Asp Thr Ser Gly Pro Ser Leu Asn Ile Leu
                725                 730                 735

Ile Lys Leu Met Ala Val Glu Ser Leu Val Phe Ala Pro Phe Phe Ala
            740                 745                 750

Thr Gln Gly Gly Leu Leu Phe Lys Tyr Leu
            755                 760

<210> SEQ ID NO 26
```

```
<211> LENGTH: 1774
<212> TYPE: DNA
<213> ORGANISM: Zea mays

<400> SEQUENCE: 26
acctggtcag ttgtatattc ccctcttttt tattagtgaa taaagatatc caaaaaactt      60
gaaatgcact acctctattt tattatttgg tttttatgat gaaaactttt tttttacttt     120
tctggtttta ttgtgactgt agtataagac agcatgggac ctctcaaata ttgtctctgc     180
ggatgacgct attgtcagtt ataaatattg gcggcatatt aggaaacaaa ttatccctat     240
ttgagttgcg cacacatatc atgttattat tgtgaatttg tgagatattg aggttgatga     300
tatatatgtt gttcattttc atgtgatcgt tatgcactaa cagttatcga ataatttata     360
cgcgtcgcaa cgcacgggca catacatagt tacaatttaa gtggccagat tacactttct     420
tcttcggggt gatttttaac taaacatcta acaatgcgtg gagacgatgt tgctcatgct     480
gaaatagtac taccagcttc tgtcgtagca atctgtgatg agacacctcc agccctccag     540
tcaccacttc ttcagtcctt gtaataggaa ccacttcatc agtatgctct tgtattagga     600
accacttcat cagtatgtta ctgtcatata gctcgaagct ctttaggaac cacttcatca     660
gtagttaccc gtgaactatc tcgtgtacat gcaacctata gagcataatg gaattaaata     720
gttgtgaccc caccacataa gaatctaact aggtatatgc tcatgtgttg ctatgataaa     780
atacattaat atacaaaaaa tattgtgttt tataatatta actccgtagc aacgcacgag     840
catatacata taacacacac acatgtacat aagttatcgt gttattatac ggtttcgttg     900
caacgcacgg gcacttacct agtatagtat gagggaagca cattcgtgtg ttgcagaatg     960
cagactacca gctgtccagc cctccctcat tcaagacgtg tggggtttgc tcctccgatc    1020
gagtggcacg cacccgtttt ttcaggccta attatggtgc agtgcagtgc agccgctctc    1080
ctgcctgtcc tccccgtggt tcgttccctc gccggaccac cgtggggccg gtagccgctg    1140
cctgcttgct actagatccg atccagcctc gcatcgcatg cccatgccgc catgcggatg    1200
gataataact gtacagtgcc tctttgatag ggtctggcgg ccaggaacta gcgacccgac    1260
caatcgttta tgctcttgca ctgtccgtct acaccgtgtc ccgatcgatt ccactgcctg    1320
tgcgtacgag tagggctggg ccagtaggga tctttctcgc caatcagccc gcatatatgg    1380
acccagtcag taattggctc gcaagtcaca acagatctcg atcggtctgt tgtaccaatc    1440
tacgtactag caacatgtac acgcacgtac cgaagcgggc gtaaaacgtt gtcacgatac    1500
aaactttcgg cggcaagagc atgcggcgcg ctgagcgcag cgcagcgcag tcgtccggtc    1560
gtcccatcgc ggccgttttc ggcgtacgta cggcggtacg ggctacggag cactgactga    1620
ctcgtcggcc gtccaactgt gtagtccgcc gataccgcct gggccaatag cggaatagcc    1680
caaggcgcga gacggcggcg tcacacatcg gcgcagttgg ttgggtcgag ctcccaacca    1740
actcgctccc gcgccagcca agccagccac gacc                                1774
```